(12) United States Patent
Xu et al.

(10) Patent No.: US 11,839,661 B2
(45) Date of Patent: Dec. 12, 2023

(54) RAPID FORMATION OF SUPRAMOLECULAR HYDROGELS BY SHORT PEPTIDE AND BIOACTIVE SMALL MOLECULES

(71) Applicant: BRANDEIS UNIVERSITY, Waltham, MA (US)

(72) Inventors: Bing Xu, Newton, MA (US); Huaimin Wang, Waltham, MA (US)

(73) Assignee: BRANDEIS UNIVERSITY, Waltham, MA (US)

( * ) Notice: Subject to any disclaimer, the term of this patent is extended or adjusted under 35 U.S.C. 154(b) by 337 days.

(21) Appl. No.: 16/639,467

(22) PCT Filed: Aug. 15, 2018

(86) PCT No.: PCT/US2018/000197
§ 371 (c)(1),
(2) Date: Feb. 14, 2020

(87) PCT Pub. No.: WO2019/035928
PCT Pub. Date: Feb. 21, 2019

(65) Prior Publication Data
US 2021/0128745 A1    May 6, 2021

Related U.S. Application Data

(60) Provisional application No. 62/545,755, filed on Aug. 15, 2017.

(51) Int. Cl.
| | | |
|---|---|---|
| *A61K 47/69* | (2017.01) | |
| *A61P 35/00* | (2006.01) | |
| *A61K 9/00* | (2006.01) | |
| *A61K 31/573* | (2006.01) | |
| *A61K 31/704* | (2006.01) | |
| *A61K 39/39* | (2006.01) | |
| *A61K 45/06* | (2006.01) | |
| *C07K 7/06* | (2006.01) | |
| *C07K 7/08* | (2006.01) | |
| *A61K 39/00* | (2006.01) | |

(52) U.S. Cl.
CPC ........ *A61K 47/6903* (2017.08); *A61K 9/0014* (2013.01); *A61K 31/573* (2013.01); *A61K 31/704* (2013.01); *A61K 39/39* (2013.01); *A61K 45/06* (2013.01); *A61P 35/00* (2018.01); *C07K 7/06* (2013.01); *C07K 7/08* (2013.01); *A61K 2039/6031* (2013.01)

(58) Field of Classification Search
None
See application file for complete search history.

(56) References Cited

U.S. PATENT DOCUMENTS

| | | | |
|---|---|---|---|
| 4,804,650 A * | 2/1989 | Lewicki | ................. C07K 14/58 |
| | | | 930/DIG. 530 |
| 8,658,600 B2 | 2/2014 | Gao et al. | |
| 9,408,921 B2 | 8/2016 | Gao et al. | |
| 10,093,674 B2 | 10/2018 | Xu et al. | |
| 10,232,037 B2 | 3/2019 | Zhao et al. | |
| 10,308,682 B2 | 6/2019 | Xu et al. | |
| 2012/0142616 A1 | 6/2012 | Gao et al. | |
| 2014/0148410 A1 | 5/2014 | Xu | |
| 2014/0235550 A1 | 8/2014 | Gao et al. | |
| 2014/0349933 A1 | 11/2014 | Hauser et al. | |
| 2015/0306232 A1* | 10/2015 | Xu | ....................... C07K 5/1016 |
| | | | 428/221 |
| 2016/0016994 A1 | 1/2016 | Xu et al. | |
| 2017/0007696 A1 | 1/2017 | Zhao et al. | |
| 2017/0037082 A1 | 2/2017 | Xu et al. | |
| 2017/0119910 A1 | 5/2017 | Du et al. | |
| 2018/0037605 A1 | 2/2018 | Du et al. | |
| 2019/0224330 A1 | 7/2019 | Wang et al. | |
| 2020/0023065 A1 | 1/2020 | Xu | |

FOREIGN PATENT DOCUMENTS

| | | | |
|---|---|---|---|
| WO | 2008085691 A2 | 7/2008 | |
| WO | 2010/151644 A2 | 12/2010 | |
| WO | 2012/166705 A2 | 12/2012 | |
| WO | 2012/166706 A2 | 12/2012 | |
| WO | 2014/074789 A1 | 5/2014 | |
| WO | 2014/138367 A1 | 9/2014 | |
| WO | 2015/116242 A1 | 8/2015 | |
| WO | 2015/157530 A2 | 10/2015 | |
| WO | 2015/157535 A2 | 10/2015 | |
| WO | 2015188064 A1 | 12/2015 | |
| WO | 2016138433 A1 | 9/2016 | |
| WO | WO-2016138433 A1 * | 9/2016 | ............. A61K 47/54 |

(Continued)

OTHER PUBLICATIONS

Wang, Angewandte Chemie, 56, May 26, 2017 (Year: 2017).*
Zhang, Angew Chem Int ed, 51, 2012 (Year: 2012).*
Oligomerization, Compendium of Chemical Terminology, IUPAC, 1996 (Year: 1996).*

(Continued)

*Primary Examiner* — Robert A Wax
*Assistant Examiner* — William Craigo
(74) *Attorney, Agent, or Firm* — Troutman Pepper Hamilton Sanders LLP (Rochester)

(57) ABSTRACT

Disclosed are a peptide capable of induced self-assembly by a bioactive molecule comprising a (i) hydrogelation-promoting amino acid sequence and (ii) an oligomerization sequence; compositions containing the peptide and, optionally, bioactive molecule; hydrogels formed thereby; and various methods of using the same.

27 Claims, 25 Drawing Sheets

Specification includes a Sequence Listing.

(56) References Cited

FOREIGN PATENT DOCUMENTS

WO    2017/189996 A1    11/2017
WO    2018/129171 A1    7/2018

OTHER PUBLICATIONS

International Search Report and Written Opinion for corresponding International Application No. PCT/US2018/000197 (dated Nov. 16, 2018).
Boyle et al., "Rational Design of Peptide-Based Biosupramolecular Systems," Supramolecular Chemistry: From Molecules to Nanomaterials, 1-26 (2012).
Wang et al., "Instant Hydrogelation Inspired by Inflammasomes," Angew Chem Int Ed Engl., 56(26): 7579-7583 (2017).
Zhang et al., "Versatile Small Molecular Motifs for Self-assembly in Water and Formation of Biofunctional Supramolecular Hydrogels," Langmuir, 27(2):529-537 (2011).
Wang, et al., "Instant Hydrogelation Inspired by Inflammasomes," MIT Polymer Day Symposium (Mar. 19, 2017).
Lu et al., "Unified Polymerization Mechanism for the Assembly of ASC-Dependent Inflammasomes," Cell 156:1193-1206 (2014).
Lu and Wu, "Structural Mechanisms of Inflammasome Assembly," FEBS Journal 282:435-444 (2014).
Wang et al., "Nucleopeptide Assemblies Selectively Sequester ATP in Cancer Cells to Increase the Efficacy of Doxorubicin," Angew. Chem. Int. Ed. 57:4931-4935 (2018).

\* cited by examiner

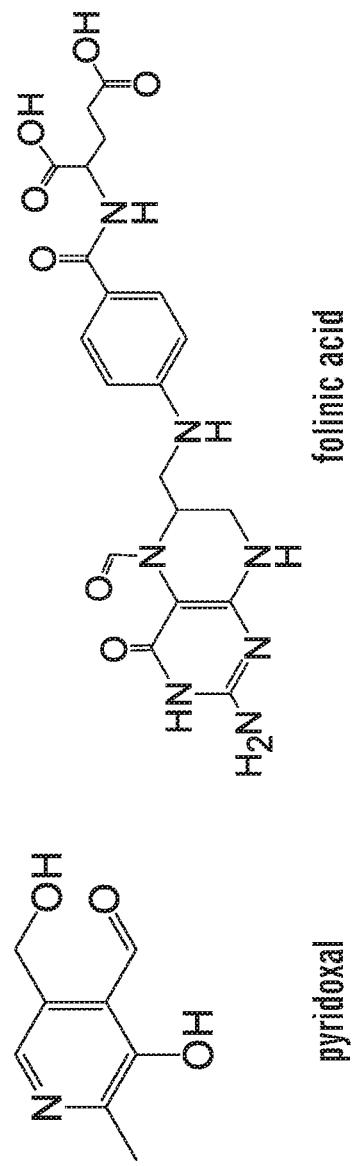
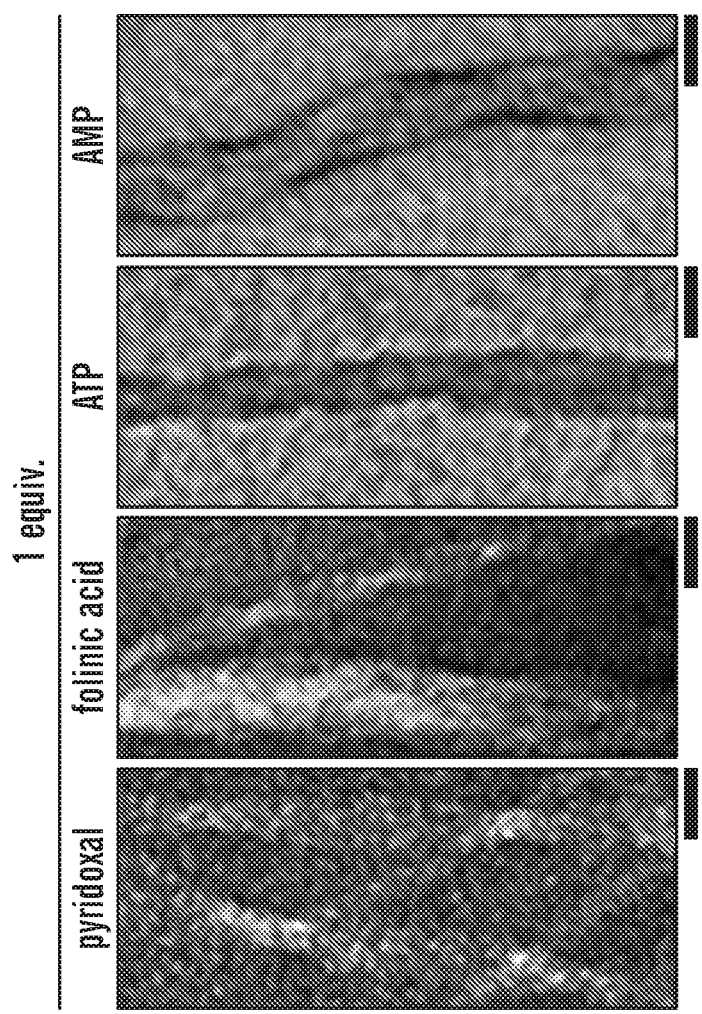
FIG. 4A

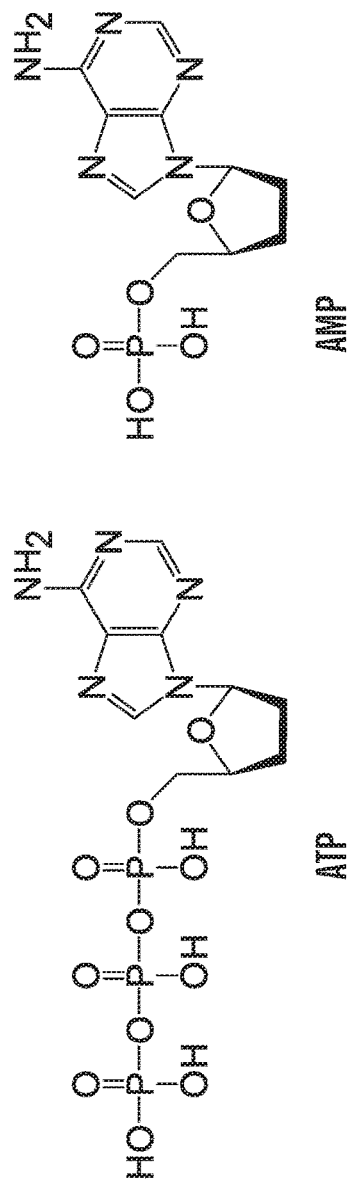
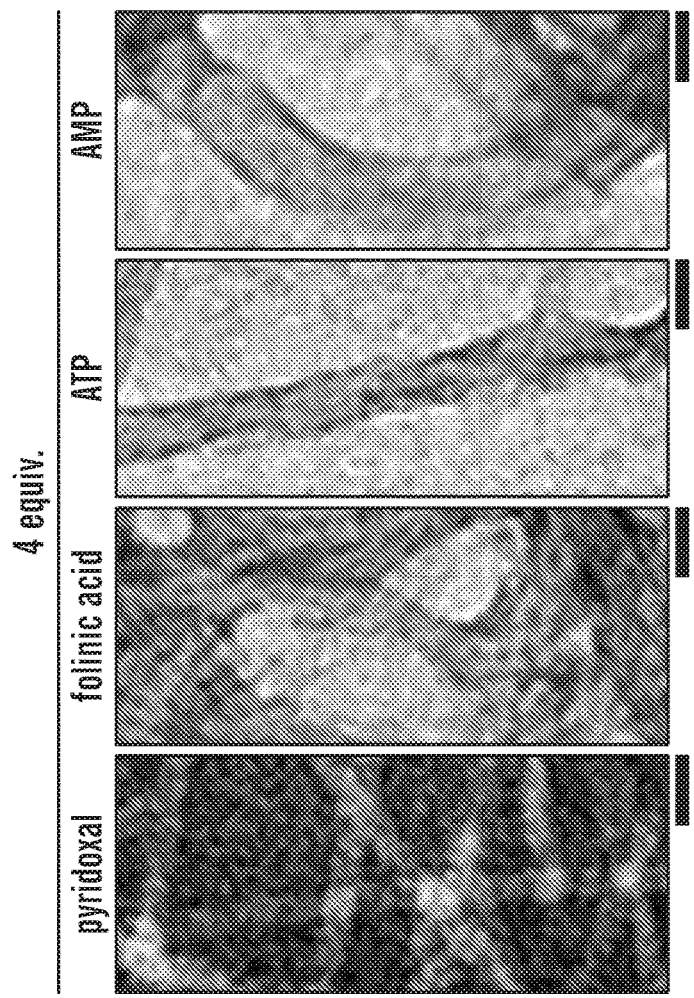
FIG. 4A (cont.)

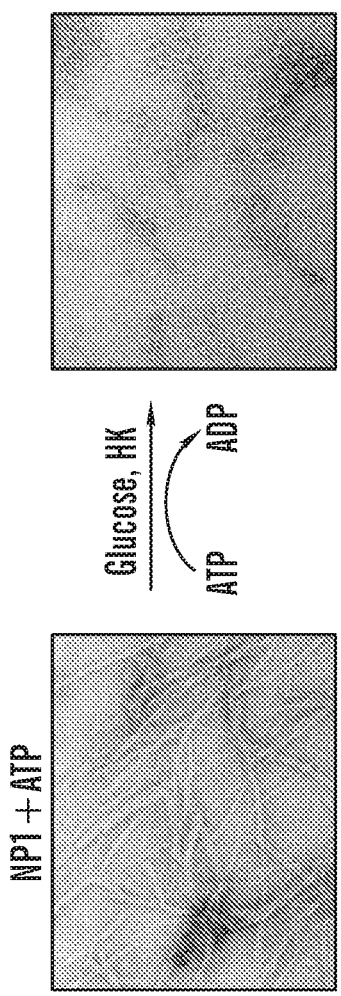
FIG. 12A NP1 + ATP
FIG. 12B Glucose, HK; ATP → ADP
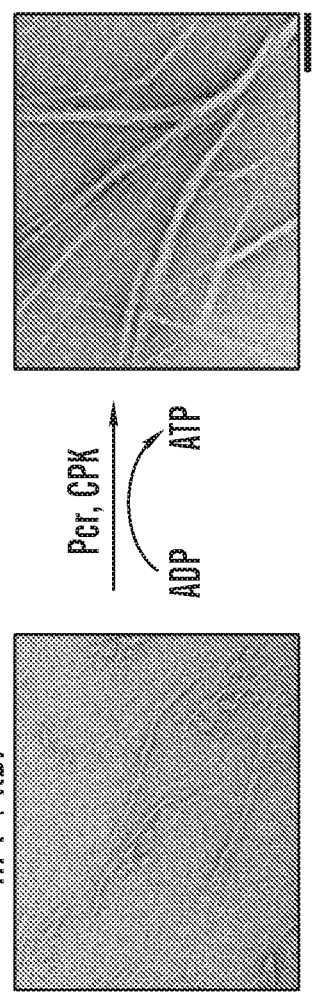
FIG. 12C NP1 + ADP
FIG. 12D PCr, CPK; ADP → ATP

SEQUENCE LISTING

<160> NUMBER OF SEQ ID NOS: 101

<210> SEQ ID NO 1
<211> LENGTH: 9
<212> TYPE: PRT
<213> ORGANISM: Artificial Sequence

```
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-napthylacetyl-
      phenylalanine

<400> SEQUENCE: 1

Xaa Phe Lys Lys Phe Lys Leu Lys Leu
1               5

<210> SEQ ID NO 2
<211> LENGTH: 7
<212> TYPE: PRT
<213> ORGANISM: Artificial Sequence
<220> FEATURE:
<223> OTHER INFORMATION: Oligomerization sequence

<400> SEQUENCE: 2

Lys Lys Phe Lys Leu Lys Leu
1               5

<210> SEQ ID NO 3
<211> LENGTH: 8
<212> TYPE: PRT
<213> ORGANISM: Artificial Sequence
<220> FEATURE:
<223> OTHER INFORMATION: Oligomerization sequence

<400> SEQUENCE: 3

Leu Lys Lys Phe Lys Leu Lys Leu
1               5

<210> SEQ ID NO 4
<211> LENGTH: 7
<212> TYPE: PRT
<213> ORGANISM: Artificial Sequence
<220> FEATURE:
<223> OTHER INFORMATION: Oligomerization sequence

<400> SEQUENCE: 4

Lys Lys Phe Lys Met Lys Leu
1               5

<210> SEQ ID NO 5
<211> LENGTH: 8
<212> TYPE: PRT
<213> ORGANISM: Artificial Sequence
<220> FEATURE:
<223> OTHER INFORMATION: Oligomerization sequence

<400> SEQUENCE: 5

Leu Lys Lys Phe Lys Met Lys Leu
1               5

<210> SEQ ID NO 6
<211> LENGTH: 7
<212> TYPE: PRT
<213> ORGANISM: Artificial Sequence
<220> FEATURE:
<223> OTHER INFORMATION: Oligomerization sequence

<400> SEQUENCE: 6

Arg Lys Phe Lys Ser Lys Leu
1               5
```

```
<210> SEQ ID NO 7
<211> LENGTH: 8
<212> TYPE: PRT
<213> ORGANISM: Artificial Sequence
<220> FEATURE:
<223> OTHER INFORMATION: Oligomerization sequence

<400> SEQUENCE: 7

Leu Arg Lys Phe Lys Ser Lys Leu
1               5

<210> SEQ ID NO 8
<211> LENGTH: 7
<212> TYPE: PRT
<213> ORGANISM: Artificial Sequence
<220> FEATURE:
<223> OTHER INFORMATION: Oligomerization sequence

<400> SEQUENCE: 8

Lys Lys Phe Lys Gly Lys Leu
1               5

<210> SEQ ID NO 9
<211> LENGTH: 8
<212> TYPE: PRT
<213> ORGANISM: Artificial Sequence
<220> FEATURE:
<223> OTHER INFORMATION: Oligomerization sequence

<400> SEQUENCE: 9

Phe Lys Lys Phe Lys Gly Lys Leu
1               5

<210> SEQ ID NO 10
<211> LENGTH: 7
<212> TYPE: PRT
<213> ORGANISM: Artificial Sequence
<220> FEATURE:
<223> OTHER INFORMATION: Oligomerization sequence

<400> SEQUENCE: 10

Glu Lys Phe Lys Phe Lys Leu
1               5

<210> SEQ ID NO 11
<211> LENGTH: 8
<212> TYPE: PRT
<213> ORGANISM: Artificial Sequence
<220> FEATURE:
<223> OTHER INFORMATION: Oligomerization sequence

<400> SEQUENCE: 11

Phe Glu Lys Phe Lys Phe Lys Leu
1               5

<210> SEQ ID NO 12
<211> LENGTH: 7
<212> TYPE: PRT
<213> ORGANISM: Artificial Sequence
<220> FEATURE:
<223> OTHER INFORMATION: Oligomerization sequence

<400> SEQUENCE: 12

Lys Lys Leu Lys Phe Tyr Leu
1               5

<210> SEQ ID NO 13
```

```
<211> LENGTH: 8
<212> TYPE: PRT
<213> ORGANISM: Artificial Sequence
<220> FEATURE:
<223> OTHER INFORMATION: Oligomerization sequence

<400> SEQUENCE: 13

Phe Lys Lys Leu Lys Phe Tyr Leu
1               5

<210> SEQ ID NO 14
<211> LENGTH: 7
<212> TYPE: PRT
<213> ORGANISM: Artificial Sequence
<220> FEATURE:
<223> OTHER INFORMATION: Oligomerization sequence

<400> SEQUENCE: 14

Lys Thr Leu Lys Phe His Leu
1               5

<210> SEQ ID NO 15
<211> LENGTH: 8
<212> TYPE: PRT
<213> ORGANISM: Artificial Sequence
<220> FEATURE:
<223> OTHER INFORMATION: Oligomerization sequence

<400> SEQUENCE: 15

Phe Lys Thr Leu Lys Phe His Leu
1               5

<210> SEQ ID NO 16
<211> LENGTH: 7
<212> TYPE: PRT
<213> ORGANISM: Artificial Sequence
<220> FEATURE:
<223> OTHER INFORMATION: Oligomerization sequence

<400> SEQUENCE: 16

Lys Arg Phe Arg His Lys Leu
1               5

<210> SEQ ID NO 17
<211> LENGTH: 8
<212> TYPE: PRT
<213> ORGANISM: Artificial Sequence
<220> FEATURE:
<223> OTHER INFORMATION: Oligomerization sequence

<400> SEQUENCE: 17

Leu Lys Arg Phe Arg His Lys Leu
1               5

<210> SEQ ID NO 18
<211> LENGTH: 7
<212> TYPE: PRT
<213> ORGANISM: Artificial Sequence
<220> FEATURE:
<223> OTHER INFORMATION: Oligomerization sequence

<400> SEQUENCE: 18

Lys Lys Phe Gln Trp His Leu
1               5

<210> SEQ ID NO 19
<211> LENGTH: 8
```

```
<212> TYPE: PRT
<213> ORGANISM: Artificial Sequence
<220> FEATURE:
<223> OTHER INFORMATION: Oligomerization sequence

<400> SEQUENCE: 19

Leu Lys Lys Phe Gln Trp His Leu
1               5

<210> SEQ ID NO 20
<211> LENGTH: 29
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is phenylalanine having an
      N-linked capping moiety

<400> SEQUENCE: 20

Xaa Ala Pro Phe Phe Cys Ala Pro Phe Phe Lys Cys Ala Pro Phe Phe
1               5                   10                  15

Cys Ala Pro Phe Phe Lys Cys Ala Pro Phe Phe Lys Phe
            20                  25

<210> SEQ ID NO 21
<211> LENGTH: 10
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-napthylacetyl-
      phenylalanine

<400> SEQUENCE: 21

Xaa Phe Leu Lys Lys Phe Lys Leu Lys Leu
1               5                   10

<210> SEQ ID NO 22
<211> LENGTH: 9
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-napthylacetyl-
      phenylalanine

<400> SEQUENCE: 22

Xaa Phe Lys Lys Phe Lys Met Lys Leu
1               5

<210> SEQ ID NO 23
<211> LENGTH: 10
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-napthylacetyl-
      phenylalanine
```

<400> SEQUENCE: 23

Xaa Phe Leu Lys Lys Phe Lys Met Lys Leu
1               5                   10

<210> SEQ ID NO 24
<211> LENGTH: 9
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-napthylacetyl-
      phenylalanine

<400> SEQUENCE: 24

Xaa Phe Arg Lys Phe Lys Ser Lys Leu
1               5

<210> SEQ ID NO 25
<211> LENGTH: 10
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-napthylacetyl-
      phenylalanine

<400> SEQUENCE: 25

Xaa Phe Leu Arg Lys Phe Lys Ser Lys Leu
1               5                   10

<210> SEQ ID NO 26
<211> LENGTH: 9
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-napthylacetyl-
      phenylalanine

<400> SEQUENCE: 26

Xaa Phe Lys Lys Phe Lys Gly Lys Leu
1               5

<210> SEQ ID NO 27
<211> LENGTH: 10
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-napthylacetyl-
      phenylalanine

<400> SEQUENCE: 27

Xaa Phe Phe Lys Lys Phe Lys Gly Lys Leu
1               5                   10

```
<210> SEQ ID NO 28
<211> LENGTH: 9
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-napthylacetyl-
      phenylalanine

<400> SEQUENCE: 28

Xaa Phe Glu Lys Phe Lys Phe Lys Leu
1               5

<210> SEQ ID NO 29
<211> LENGTH: 10
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-napthylacetyl-
      phenylalanine

<400> SEQUENCE: 29

Xaa Phe Phe Glu Lys Phe Lys Phe Lys Leu
1               5                   10

<210> SEQ ID NO 30
<211> LENGTH: 9
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-napthylacetyl-
      phenylalanine

<400> SEQUENCE: 30

Xaa Phe Lys Lys Leu Lys Phe Tyr Leu
1               5

<210> SEQ ID NO 31
<211> LENGTH: 10
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-napthylacetyl-
      phenylalanine

<400> SEQUENCE: 31

Xaa Phe Phe Lys Lys Leu Lys Phe Tyr Leu
1               5                   10

<210> SEQ ID NO 32
<211> LENGTH: 9
<212> TYPE: PRT
<213> ORGANISM: Artificial Sequence
<220> FEATURE:
<223> OTHER INFORMATION: hydrogelator
<220> FEATURE:
```

```
<221> NAME/KEY: MOD_RES
<222> LOCATION: (1)..(1)
<223> OTHER INFORMATION: Xaa at position 1 is N-napthylacetyl-
      phenylalanine

<400> SEQUENCE: 32

Xaa Phe Lys Thr Leu Lys Phe His Leu
1               5

<210> SEQ ID NO 33
<211> LENGTH: 10
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-napthylacetyl-
      phenylalanine

<400> SEQUENCE: 33

Xaa Phe Phe Lys Thr Leu Lys Phe His Leu
1               5                   10

<210> SEQ ID NO 34
<211> LENGTH: 9
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-napthylacetyl-
      phenylalanine

<400> SEQUENCE: 34

Xaa Phe Lys Arg Phe Arg His Lys Leu
1               5

<210> SEQ ID NO 35
<211> LENGTH: 10
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-napthylacetyl-
      phenylalanine

<400> SEQUENCE: 35

Xaa Phe Leu Lys Arg Phe Arg His Lys Leu
1               5                   10

<210> SEQ ID NO 36
<211> LENGTH: 9
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-napthylacetyl-
      phenylalanine

<400> SEQUENCE: 36
```

```
Xaa Phe Lys Lys Phe Gln Trp His Leu
1               5
```

<210> SEQ ID NO 37
<211> LENGTH: 10
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-napthylacetyl-
      phenylalanine

<400> SEQUENCE: 37

```
Xaa Phe Leu Lys Lys Phe Gln Trp His Leu
1               5                   10
```

<210> SEQ ID NO 38
<211> LENGTH: 10
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-napthylacetyl-
      phenylalanine

<400> SEQUENCE: 38

```
Xaa Phe Lys Lys Lys Phe Lys Leu Lys Leu
1               5                   10
```

<210> SEQ ID NO 39
<211> LENGTH: 11
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-napthylacetyl-
      phenylalanine

<400> SEQUENCE: 39

```
Xaa Phe Lys Leu Lys Lys Phe Lys Leu Lys Leu
1               5                   10
```

<210> SEQ ID NO 40
<211> LENGTH: 10
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-napthylacetyl-
      phenylalanine

<400> SEQUENCE: 40

```
Xaa Phe Lys Lys Lys Phe Lys Met Lys Leu
1               5                   10
```

<210> SEQ ID NO 41
<211> LENGTH: 11
<212> TYPE: PRT

<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-napthylacetyl-
      phenylalanine

<400> SEQUENCE: 41

Xaa Phe Lys Leu Lys Lys Phe Lys Met Lys Leu
1               5                   10

<210> SEQ ID NO 42
<211> LENGTH: 10
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-napthylacetyl-
      phenylalanine

<400> SEQUENCE: 42

Xaa Phe Lys Arg Lys Phe Lys Ser Lys Leu
1               5                   10

<210> SEQ ID NO 43
<211> LENGTH: 11
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-napthylacetyl-
      phenylalanine

<400> SEQUENCE: 43

Xaa Phe Lys Leu Arg Lys Phe Lys Ser Lys Leu
1               5                   10

<210> SEQ ID NO 44
<211> LENGTH: 10
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-napthylacetyl-
      phenylalanine

<400> SEQUENCE: 44

Xaa Phe Lys Lys Lys Phe Lys Gly Lys Leu
1               5                   10

<210> SEQ ID NO 45
<211> LENGTH: 11
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-napthylacetyl-

```
                phenylalanine

<400> SEQUENCE: 45

Xaa Phe Lys Phe Lys Lys Phe Lys Gly Lys Leu
1               5                   10

<210> SEQ ID NO 46
<211> LENGTH: 10
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-napthylacetyl-
      phenylalanine

<400> SEQUENCE: 46

Xaa Phe Lys Glu Lys Phe Lys Phe Lys Leu
1               5                   10

<210> SEQ ID NO 47
<211> LENGTH: 11
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-napthylacetyl-
      phenylalanine

<400> SEQUENCE: 47

Xaa Phe Lys Phe Glu Lys Phe Lys Phe Lys Leu
1               5                   10

<210> SEQ ID NO 48
<211> LENGTH: 10
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-napthylacetyl-
      phenylalanine

<400> SEQUENCE: 48

Xaa Phe Lys Lys Lys Leu Lys Phe Tyr Leu
1               5                   10

<210> SEQ ID NO 49
<211> LENGTH: 11
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-napthylacetyl-
      phenylalanine

<400> SEQUENCE: 49

Xaa Phe Lys Phe Lys Lys Leu Lys Phe Tyr Leu
1               5                   10
```

<210> SEQ ID NO 50
<211> LENGTH: 10
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-napthylacetyl-
      phenylalanine

<400> SEQUENCE: 50

Xaa Phe Lys Lys Thr Leu Lys Phe His Leu
1               5                   10

<210> SEQ ID NO 51
<211> LENGTH: 11
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-napthylacetyl-
      phenylalanine

<400> SEQUENCE: 51

Xaa Phe Lys Phe Lys Thr Leu Lys Phe His Leu
1               5                   10

<210> SEQ ID NO 52
<211> LENGTH: 10
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-napthylacetyl-
      phenylalanine

<400> SEQUENCE: 52

Xaa Phe Lys Lys Arg Phe Arg His Lys Leu
1               5                   10

<210> SEQ ID NO 53
<211> LENGTH: 11
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-napthylacetyl-
      phenylalanine

<400> SEQUENCE: 53

Xaa Phe Lys Leu Lys Arg Phe Arg His Lys Leu
1               5                   10

<210> SEQ ID NO 54
<211> LENGTH: 10
<212> TYPE: PRT
<213> ORGANISM: Artificial Sequence
<220> FEATURE:
<223> OTHER INFORMATION: hydrogelator -continued

```
<220> FEATURE:
<221> NAME/KEY: MOD_RES
<222> LOCATION: (1)..(1)
<223> OTHER INFORMATION: Xaa at position 1 is N-napthylacetyl-
      phenylalanine

<400> SEQUENCE: 54

Xaa Phe Lys Lys Lys Phe Gln Trp His Leu
1               5                   10

<210> SEQ ID NO 55
<211> LENGTH: 11
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-napthylacetyl-
      phenylalanine

<400> SEQUENCE: 55

Xaa Phe Lys Leu Lys Lys Phe Gln Trp His Leu
1               5                   10

<210> SEQ ID NO 56
<211> LENGTH: 11
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-napthylacetyl-
      phenylalanine

<400> SEQUENCE: 56

Xaa Phe Lys Phe Lys Lys Phe Lys Leu Lys Leu
1               5                   10

<210> SEQ ID NO 57
<211> LENGTH: 12
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-napthylacetyl-
      phenylalanine

<400> SEQUENCE: 57

Xaa Phe Lys Phe Leu Lys Lys Phe Lys Leu Lys Leu
1               5                   10

<210> SEQ ID NO 58
<211> LENGTH: 11
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-napthylacetyl-
      phenylalanine

<400> SEQUENCE: 58
```

```
Xaa Phe Lys Phe Lys Lys Phe Lys Met Lys Leu
1               5                   10
```

<210> SEQ ID NO 59
<211> LENGTH: 12
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-napthylacetyl-
      phenylalanine

<400> SEQUENCE: 59

```
Xaa Phe Lys Phe Leu Lys Lys Phe Lys Met Lys Leu
1               5                   10
```

<210> SEQ ID NO 60
<211> LENGTH: 11
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-napthylacetyl-
      phenylalanine

<400> SEQUENCE: 60

```
Xaa Phe Lys Phe Arg Lys Phe Lys Ser Lys Leu
1               5                   10
```

<210> SEQ ID NO 61
<211> LENGTH: 12
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-napthylacetyl-
      phenylalanine

<400> SEQUENCE: 61

```
Xaa Phe Lys Phe Leu Arg Lys Phe Lys Ser Lys Leu
1               5                   10
```

<210> SEQ ID NO 62
<211> LENGTH: 11
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-napthylacetyl-
      phenylalanine

<400> SEQUENCE: 62

```
Xaa Phe Lys Phe Lys Lys Phe Lys Gly Lys Leu
1               5                   10
```

<210> SEQ ID NO 63
<211> LENGTH: 12

```
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-napthylacetyl-
      phenylalanine

<400> SEQUENCE: 63

Xaa Phe Lys Phe Phe Lys Lys Phe Lys Gly Lys Leu
1               5                   10

<210> SEQ ID NO 64
<211> LENGTH: 11
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-napthylacetyl-
      phenylalanine

<400> SEQUENCE: 64

Xaa Phe Lys Phe Glu Lys Phe Lys Phe Lys Leu
1               5                   10

<210> SEQ ID NO 65
<211> LENGTH: 12
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-napthylacetyl-
      phenylalanine

<400> SEQUENCE: 65

Xaa Phe Lys Phe Phe Glu Lys Phe Lys Phe Lys Leu
1               5                   10

<210> SEQ ID NO 66
<211> LENGTH: 11
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (1)..(1)
<223> OTHER INFORMATION: Xaa at position 1 is N-napthylacetyl-
      phenylalanine

<400> SEQUENCE: 66

Xaa Phe Lys Phe Lys Lys Leu Lys Phe Tyr Leu
1               5                   10

<210> SEQ ID NO 67
<211> LENGTH: 12
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
```

<223> OTHER INFORMATION: Xaa at position 1 is N-napthylacetyl-
          phenylalanine

<400> SEQUENCE: 67

Xaa Phe Lys Phe Phe Lys Lys Leu Lys Phe Tyr Leu
1               5                   10

<210> SEQ ID NO 68
<211> LENGTH: 11
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-napthylacetyl-
      phenylalanine

<400> SEQUENCE: 68

Xaa Phe Lys Phe Lys Thr Leu Lys Phe His Leu
1               5                   10

<210> SEQ ID NO 69
<211> LENGTH: 12
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-napthylacetyl-
      phenylalanine

<400> SEQUENCE: 69

Xaa Phe Lys Phe Phe Lys Thr Leu Lys Phe His Leu
1               5                   10

<210> SEQ ID NO 70
<211> LENGTH: 11
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-napthylacetyl-
      phenylalanine

<400> SEQUENCE: 70

Xaa Phe Lys Phe Lys Arg Phe Arg His Lys Leu
1               5                   10

<210> SEQ ID NO 71
<211> LENGTH: 12
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-napthylacetyl-
      phenylalanine

<400> SEQUENCE: 71

Xaa Phe Lys Phe Leu Lys Arg Phe Arg His Lys Leu
1               5                   10

```
<210> SEQ ID NO 72
<211> LENGTH: 11
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-napthylacetyl-
      phenylalanine

<400> SEQUENCE: 72

Xaa Phe Lys Phe Lys Lys Phe Gln Trp His Leu
1               5                   10

<210> SEQ ID NO 73
<211> LENGTH: 12
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-napthylacetyl-
      phenylalanine

<400> SEQUENCE: 73

Xaa Phe Lys Phe Leu Lys Lys Phe Gln Trp His Leu
1               5                   10

<210> SEQ ID NO 74
<211> LENGTH: 9
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-thyminylacetyl-
      phenylalanine

<400> SEQUENCE: 74

Xaa Phe Lys Lys Phe Lys Leu Lys Leu
1               5

<210> SEQ ID NO 75
<211> LENGTH: 7
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-thyminylacetyl-
      phenylalanine

<400> SEQUENCE: 75

Xaa Phe Lys Lys Phe Lys Leu
1               5

<210> SEQ ID NO 76
<211> LENGTH: 5
<212> TYPE: PRT
<213> ORGANISM: Artificial Sequence
<220> FEATURE:
```

```
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-thyminylacetyl-
      phenylalanine

<400> SEQUENCE: 76

Xaa Phe Lys Lys Phe
1               5

<210> SEQ ID NO 77
<211> LENGTH: 8
<212> TYPE: PRT
<213> ORGANISM: Artificial Sequence
<220> FEATURE:
<223> OTHER INFORMATION: NP1 analog
<220> FEATURE:
<221> NAME/KEY: MOD_RES
<222> LOCATION: (1)..(1)
<223> OTHER INFORMATION: Xaa at position 1 is N-thyminylacetyl-
      phenylalanine

<400> SEQUENCE: 77

Xaa Phe Lys Lys Phe Lys Leu Lys
1               5

<210> SEQ ID NO 78
<211> LENGTH: 6
<212> TYPE: PRT
<213> ORGANISM: Artificial Sequence
<220> FEATURE:
<223> OTHER INFORMATION: NP1 analog
<220> FEATURE:
<221> NAME/KEY: MOD_RES
<222> LOCATION: (1)..(1)
<223> OTHER INFORMATION: Xaa at position 1 is N-thyminylacetyl-
      phenylalanine

<400> SEQUENCE: 78

Xaa Phe Lys Lys Phe Lys
1               5

<210> SEQ ID NO 79
<211> LENGTH: 4
<212> TYPE: PRT
<213> ORGANISM: Artificial Sequence
<220> FEATURE:
<223> OTHER INFORMATION: NP1 analog
<220> FEATURE:
<221> NAME/KEY: MOD_RES
<222> LOCATION: (1)..(1)
<223> OTHER INFORMATION: Xaa at position 1 is N-thyminylacetyl-
      phenylalanine

<400> SEQUENCE: 79

Xaa Phe Lys Lys
1

<210> SEQ ID NO 80
<211> LENGTH: 7
<212> TYPE: PRT
<213> ORGANISM: Artificial Sequence
<220> FEATURE:
<223> OTHER INFORMATION: NP1 analog
<220> FEATURE:
<221> NAME/KEY: MOD_RES
<222> LOCATION: (1)..(1)
<223> OTHER INFORMATION: Xaa at position 1 is N-thyminylacetyl-lysine

<400> SEQUENCE: 80
```

Xaa Lys Phe Lys Leu Lys Leu
1               5

<210> SEQ ID NO 81
<211> LENGTH: 9
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-thyminylacetyl-
      phenylalanine

<400> SEQUENCE: 81

Xaa Phe Arg Arg Phe Arg Leu Arg Leu
1               5

<210> SEQ ID NO 82
<211> LENGTH: 9
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-uracilylacetyl-
      phenylalanine

<400> SEQUENCE: 82

Xaa Phe Lys Lys Phe Lys Leu Lys Leu
1               5

<210> SEQ ID NO 83
<211> LENGTH: 7
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-uracilylacetyl-
      phenylalanine

<400> SEQUENCE: 83

Xaa Phe Lys Lys Phe Lys Leu
1               5

<210> SEQ ID NO 84
<211> LENGTH: 5
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-uracilylacetyl-
      phenylalanine

<400> SEQUENCE: 84

Xaa Phe Lys Lys Phe
1               5

<210> SEQ ID NO 85
<211> LENGTH: 9

```
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-uracilylacetyl-
      phenylalanine

<400> SEQUENCE: 85

Xaa Phe Arg Arg Phe Arg Leu Arg Leu
1               5

<210> SEQ ID NO 86
<211> LENGTH: 9
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N- cytosinylacetyl-
      phenylalanine

<400> SEQUENCE: 86

Xaa Phe Lys Lys Phe Lys Leu Lys Leu
1               5

<210> SEQ ID NO 87
<211> LENGTH: 7
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N- cytosinylacetyl-
      phenylalanine

<400> SEQUENCE: 87

Xaa Phe Lys Lys Phe Lys Leu
1               5

<210> SEQ ID NO 88
<211> LENGTH: 5
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N- cytosinylacetyl-
      phenylalanine

<400> SEQUENCE: 88

Xaa Phe Lys Lys Phe
1               5

<210> SEQ ID NO 89
<211> LENGTH: 9
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
```

<223> OTHER INFORMATION: Xaa at position 1 is N- cytosinylacetyl-
      phenylalanine

<400> SEQUENCE: 89

Xaa Phe Arg Arg Phe Arg Leu Arg Leu
1               5

<210> SEQ ID NO 90
<211> LENGTH: 9
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-adeninylacetyl-
      phenylalanine

<400> SEQUENCE: 90

Xaa Phe Lys Lys Phe Lys Leu Lys Leu
1               5

<210> SEQ ID NO 91
<211> LENGTH: 7
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-adeninylacetyl-
      phenylalanine

<400> SEQUENCE: 91

Xaa Phe Lys Lys Phe Lys Leu
1               5

<210> SEQ ID NO 92
<211> LENGTH: 5
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-adeninylacetyl-
      phenylalanine

<400> SEQUENCE: 92

Xaa Phe Lys Lys Phe
1               5

<210> SEQ ID NO 93
<211> LENGTH: 9
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-adeninylacetyl-
      phenylalanine

<400> SEQUENCE: 93

Xaa Phe Arg Arg Phe Arg Leu Arg Leu
1               5

```
<210> SEQ ID NO 94
<211> LENGTH: 9
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-guaninylacetyl-
      phenylalanine

<400> SEQUENCE: 94

Xaa Phe Lys Lys Phe Lys Leu Lys Leu
1               5

<210> SEQ ID NO 95
<211> LENGTH: 7
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-guaninylacetyl-
      phenylalanine

<400> SEQUENCE: 95

Xaa Phe Lys Lys Phe Lys Leu
1               5

<210> SEQ ID NO 96
<211> LENGTH: 5
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-guaninylacetyl-
      phenylalanine

<400> SEQUENCE: 96

Xaa Phe Lys Lys Phe
1               5

<210> SEQ ID NO 97
<211> LENGTH: 9
<212> TYPE: PRT
<213> ORGANISM: Artificial Sequence
<220> FEATURE:
<223> OTHER INFORMATION: hydrogelator
<220> FEATURE:
<221> NAME/KEY: MOD_RES
<222> LOCATION: (1)..(1)
<223> OTHER INFORMATION: Xaa at position 1 is N-guaninylacetyl-
      phenylalanine

<400> SEQUENCE: 97

Xaa Phe Arg Arg Phe Arg Leu Arg Leu
1               5

<210> SEQ ID NO 98
<211> LENGTH: 7
<212> TYPE: PRT
<213> ORGANISM: Artificial Sequence
<220> FEATURE:
```

```
<223> OTHER INFORMATION: consensus oligomerization sequence
<220> FEATURE:
<221> NAME/KEY: MISC_FEATURE
<222> LOCATION: (1)..(1)
<223> OTHER INFORMATION: Xaa at position 1 is lysine, glutamic acid, or
      arginine
<220> FEATURE:
<221> NAME/KEY: MISC_FEATURE
<222> LOCATION: (2)..(2)
<223> OTHER INFORMATION: Xaa at position 2 is lysine, threonine, or
      arginine
<220> FEATURE:
<221> NAME/KEY: MISC_FEATURE
<222> LOCATION: (3)..(3)
<223> OTHER INFORMATION: Xaa at position 3 phenylalanine or leucine
<220> FEATURE:
<221> NAME/KEY: MISC_FEATURE
<222> LOCATION: (4)..(4)
<223> OTHER INFORMATION: Xaa at position 4 is lysine, glutamine, or
      arginine
<220> FEATURE:
<221> NAME/KEY: MISC_FEATURE
<222> LOCATION: (5)..(5)
<223> OTHER INFORMATION: Xaa at position 5 is any amino acid, preferably
      tryptophan, leucine, glycine, serine, methionine, phenylalanine,
      histidine
<220> FEATURE:
<221> NAME/KEY: MISC_FEATURE
<222> LOCATION: (6)..(6)
<223> OTHER INFORMATION: Xaa at position 6 is lysine, histidine, or
      tyrosine

<400> SEQUENCE: 98

Xaa Xaa Xaa Xaa Xaa Xaa Leu
1               5

<210> SEQ ID NO 99
<211> LENGTH: 7
<212> TYPE: PRT
<213> ORGANISM: Artificial Sequence
<220> FEATURE:
<223> OTHER INFORMATION: consensus oligomerization sequence
<220> FEATURE:
<221> NAME/KEY: MISC_FEATURE
<222> LOCATION: (1)..(1)
<223> OTHER INFORMATION: Xaa at position 1 is lysine, glutamic acid,
      arginine, or a lysine residue with its sidechain conjugated to a
      therapeutic agent
<220> FEATURE:
<221> NAME/KEY: MISC_FEATURE
<222> LOCATION: (2)..(2)
<223> OTHER INFORMATION: Xaa at position 2 is lysine, threonine,
      arginine, or a lysine residue with its sidechain conjugated to a
      therapeutic agent
<220> FEATURE:
<221> NAME/KEY: MISC_FEATURE
<222> LOCATION: (3)..(3)
<223> OTHER INFORMATION: Xaa at position 3 phenylalanine or leucine
<220> FEATURE:
<221> NAME/KEY: MISC_FEATURE
<222> LOCATION: (4)..(4)
<223> OTHER INFORMATION: Xaa at position 4 is lysine, glutamine,
      arginine, or a lysine residue with its sidechain conjugated to a
      therapeutic agent
<220> FEATURE:
<221> NAME/KEY: MISC_FEATURE
<222> LOCATION: (5)..(5)
<223> OTHER INFORMATION: Xaa at position 5 is any amino acid, preferably
      tryptophan, leucine, glycine, serine, methionine, phenylalanine,
      histidine
<220> FEATURE:
<221> NAME/KEY: MISC_FEATURE
<222> LOCATION: (6)..(6)
<223> OTHER INFORMATION: Xaa at position 6 is lysine, histidine,
      tyrosine, or a lysine residue with its sidechain conjugated to a
      therapeutic agent
```

<400> SEQUENCE: 99

Xaa Xaa Xaa Xaa Xaa Xaa Leu
1               5

<210> SEQ ID NO 100
<211> LENGTH: 8
<212> TYPE: PRT
<213> ORGANISM: Artificial Sequence
<220> FEATURE:
<223> OTHER INFORMATION: consensus oligomerization sequence
<220> FEATURE:
<221> NAME/KEY: MISC_FEATURE
<222> LOCATION: (1)..(1)
<223> OTHER INFORMATION: Xaa at position 1 is leucine or phenylalanine
<220> FEATURE:
<221> NAME/KEY: MISC_FEATURE
<222> LOCATION: (2)..(2)
<223> OTHER INFORMATION: Xaa at position 2 is lysine, glutamic acid, or
      arginine
<220> FEATURE:
<221> NAME/KEY: MISC_FEATURE
<222> LOCATION: (3)..(3)
<223> OTHER INFORMATION: Xaa at position 3 is lysine, threonine, or
      arginine
<220> FEATURE:
<221> NAME/KEY: MISC_FEATURE
<222> LOCATION: (4)..(4)
<223> OTHER INFORMATION: Xaa at position 4 phenylalanine or leucine
<220> FEATURE:
<221> NAME/KEY: MISC_FEATURE
<222> LOCATION: (5)..(5)
<223> OTHER INFORMATION: Xaa at position 5 is lysine, glutamine, or
      arginine
<220> FEATURE:
<221> NAME/KEY: MISC_FEATURE
<222> LOCATION: (6)..(6)
<223> OTHER INFORMATION: Xaa at position 6 is any amino acid, preferably
      tryptophan, leucine, glycine, serine, methionine, phenylalanine,
      histidine
<220> FEATURE:
<221> NAME/KEY: MISC_FEATURE
<222> LOCATION: (7)..(7)
<223> OTHER INFORMATION: Xaa at position 7 is lysine, histidine, or
      tyrosine

<400> SEQUENCE: 100

Xaa Xaa Xaa Xaa Xaa Xaa Xaa Leu
1               5

<210> SEQ ID NO 101
<211> LENGTH: 8
<212> TYPE: PRT
<213> ORGANISM: Artificial Sequence
<220> FEATURE:
<223> OTHER INFORMATION: consensus oligomerization sequence
<220> FEATURE:
<221> NAME/KEY: MISC_FEATURE
<222> LOCATION: (1)..(1)
<223> OTHER INFORMATION: Xaa at position 1 is leucine or phenylalanine
<220> FEATURE:
<221> NAME/KEY: MISC_FEATURE
<222> LOCATION: (2)..(2)
<223> OTHER INFORMATION: Xaa at position 2 is lysine, glutamic acid,
      arginine, or a lysine residue with its sidechain conjugated to a
      therapeutic agent
<220> FEATURE:
<221> NAME/KEY: MISC_FEATURE
<222> LOCATION: (3)..(3)
<223> OTHER INFORMATION: Xaa at position 3 is lysine, threonine,
      arginine, or a lysine residue with its sidechain conjugated to a
      therapeutic agent
<220> FEATURE:
<221> NAME/KEY: MISC_FEATURE
<222> LOCATION: (4)..(4)
<223> OTHER INFORMATION: Xaa at position 4 phenylalanine or leucine

```
<220> FEATURE:
<221> NAME/KEY: MISC_FEATURE
<222> LOCATION: (5)..(5)
<223> OTHER INFORMATION: Xaa at position 5 is lysine, glutamine,
      arginine, or a lysine residue with its sidechain conjugated to a
      therapeutic agent
<220> FEATURE:
<221> NAME/KEY: MISC_FEATURE
<222> LOCATION: (6)..(6)
<223> OTHER INFORMATION: Xaa at position 6 is any amino acid, preferably
      tryptophan, leucine, glycine, serine, methionine, phenylalanine,
      histidine
<220> FEATURE:
<221> NAME/KEY: MISC_FEATURE
<222> LOCATION: (7)..(7)
<223> OTHER INFORMATION: Xaa at position 7 is lysine, histidine,
      tyrosine, or a lysine residue with its sidechain conjugated to a
      therapeutic agent

<400> SEQUENCE: 101

Xaa Xaa Xaa Xaa Xaa Xaa Xaa Leu
1               5
```

RAPID FORMATION OF SUPRAMOLECULAR HYDROGELS BY SHORT PEPTIDE AND BIOACTIVE SMALL MOLECULES This application is a national stage application under 35 U.S.C. § 371 of PCT Application No. PCT/US2018/000197, filed Aug. 15, 2018, which claims the benefit of U.S. Provisional Patent Application Ser. No. 62/545,755, filed Aug. 15, 2017, which is hereby incorporated by reference in its entirety.

This invention was made with government support under CA142746 awarded by the National Institutes of Health and DMR-1420382 awarded by the National Science Foundation. The government has certain rights in the invention.

FIELD OF THE INVENTION

The present invention relates to peptides capable of induced self-assembly by a bioactive molecule, the oligomerized products of such peptides, pharmaceutical compositions containing the same, and to their use to promote wound healing and immune response in an individual.

BACKGROUND OF THE INVENTION

Bioinspiration, as a research strategy to develop materials or technology for mimicking biological functions, has attracted considerable attention and made significant progress (Whitesides G. M., *Interface Focus* 5(4):20150031 (2015); and Versluis et al., *J. Am. Chem. Soc.* 138(28): 8670-3 (2016)). For example, the study and the mimic of mussel adhesives (Waite et al., *Science* 212(4498):1038-40 (1981); and Yu et al., *Nat. Chem. Biol.* 7(9):588-90 (2011)) has led to the development of versatile surface coatings (Lee et al., *Science* 318(5849):426-30 (2007); Lee et al., *Nature* 448(7151):338-41 (2007); and Heo et al., *J. Am. Chem. Soc.* 134(49):20139-45 (2012)) and surgical glues (Brubaker et al., *Biomaterials* 31(3):420-7 (2010) and Lee et al., *Annu. Rev. Mater. Res.* 41:99-132 (2011)). Mimicry of the movement of squids has generated soft robots able to perform certain simple tasks (Morin et al., *Science* 337(6096):828-32 (2012); Bartlett et al., *Science* 349(6244):161-5 (2015); and Floreano et al., *Nature* 521(7553):460-6 (2015)), mimicry of blood clot formation has provided a general method for detecting protease activity (Bremmer et al., *Chem. Commun.* 48(44):5482-4 (2012)), and mimicry of biological enzymatic crosslinking has created polymeric hydrogels as potential surgical adhesives (Hu et al., *J. Am. Chem. Soc.* 125(47): 14298-9 (2003)). These studies mainly focus on the functions outside cells. By mimicking the apoptotic signaling in cells (Hengartner, *Nature* 407(6805):770-6 (2000); Ashkenazi et al., *Curr. Opin. Cell Biol.* 11(2):255-60 (1999); and Riedl et al., *Nat. Rev. Mol. Cell Biol.* 8(5):405-13 (2007)), applicants have developed enzyme-instructed self-assembly ("EISA")(Yang et al., *Acc. Chem. Res.* 41(2):315-26 (2008)) for imaging the activity of enzymes (Zhou et al., "Chem. 1:246-63 (2016)) or controlling the fate of cells, including selectively kill cancer cells (Kuang et al., *Angew. Chem., Int. Ed.* 53:8104-7 (2014); Zhou et al., *J. Am. Chem. Soc.* 138:3813-23 (2016); and Wang et al., *J. Am. Chem. Soc.* 138(34):10758-61 (2016)).

One of the most common consequences of EISA is the formation of supramolecular hydrogels (Estroff et al., *Chem. Rev.* 104(3):1201-18 (2004)). Although EISA, usually involving bond cleavage, can result in hydrogels much faster than the hydrogelation caused by bond formation (Hu et al., *J. Am. Chem. Soc.* 125(47):14298-9 (2003); Williams et al., "*Nat. Nanotechnol.* 4(1):19-24 (2009); and Toledano et al., *J. Am. Chem. Soc.* 128(4):1070-1 (2006)), it still takes several minutes and involves considerable amounts of enzymes, and thus, is less than ideal for applications requiring instant hydrogelation.

The present invention is directed to overcoming these and other deficiencies in the art.

SUMMARY OF THE INVENTION

A first aspect of the invention relates to a peptide capable of induced self-assembly by a bioactive molecule comprising a (i) hydrogelation-promoting amino acid sequence and (ii) an oligomerization sequence.

A second aspect of the invention relates to a product formed by exposing the peptide according to the first aspect of the invention to a bioactive molecule that induces oligomerization and hydrogelation.

A third aspect of the invention relates to an oligomerized product comprising two or more peptides according to the first aspect of the invention in activated form.

A fourth aspect of the invention relates to a supramolecular hydrogel formed upon self-assembly of the product according to the second or third aspect of the invention in an aqueous medium.

A fifth aspect of the invention relates to a pharmaceutical composition comprising a pharmaceutically acceptable carrier and a peptide according to the first, second, or third aspects of the invention.

In any of the preceding aspects, the peptide can be conjugated to a therapeutic agent, or a therapeutic agent in non-conjugated form can be present in the products, hydrogels, or pharmaceutical compositions of the invention, such that the therapeutic agent is captured or retained in any hydrogel product formed thereby.

A sixth aspect of the invention relates to a method of delivering a therapeutic agent to an individual that includes: administering a product according to the second, third or fourth aspects of the invention, whereby the therapeutic agent is released from the product to the body of the individual after said administering.

A seventh aspect of the invention relates to a method of delivering a therapeutic agent to an individual that includes: administering a pharmaceutical composition according to the fifth aspect to the individual; and administering a bioactive activator to the site where the pharmaceutical composition is administered to induce in situ oligomerization and hydrogelation of the peptide, whereby the therapeutic agent is subsequently released from the in situ formed hydrogel to the body of the individual.

An eighth aspect of the invention relates to a method of promoting would healing. This method involves administering to a wound of a subject a therapeutically effective amount of the peptide according to the first aspect of the invention or a pharmaceutical composition according to the fifth aspect of the invention, where the administering is effective to activate the peptide and induce oligomerization of the activated peptide.

A ninth aspect of the invention relates to a method of promoting would healing. This method involves administering to a wound of a subject a therapeutically effective amount of a product according to the second, third, or fourth aspects of the invention.

A tenth aspect of the invention relates to a method of promoting an immune response to an individual that includes: administering to an individual a therapeutically effective amount of the pharmaceutical composition according to the fifth aspect of the invention, where the administering is effective to activate the peptide and induce oligomerization of the activated peptide and to induce an immune response against the antigen in the pharmaceutical composition.

An eleventh aspect of the invention relates to a method of promoting an immune response to an individual that includes: administering to an individual a therapeutically effective amount of a product according to the second, third, or fourth aspects of the invention, wherein said administering is effective to induce an immune response against the antigen in the product or oligomerized product.

A twelfth eighth aspect of the invention relates to a method of causing oligomerization and/or hydrogelation of a peptide. The method involves contacting a peptide according to the first aspect of the invention with a bioactive activator sufficient to induce oligomerization and hydrogelation.

A thirteenth aspect of the invention relates to a method of selectively sequestering ATP. The method involves contacting ATP, in an aqueous environment, with a peptide according to the first aspect of the invention or a product according to the second, third, or fourth aspects of the invention, whereby said contacting is effective to cause ATP binding to the peptide, product, or oligomerized product.

A fourteenth aspect of the invention relates to method of inhibiting cancer cell efflux of an antineoplastic agent, anticancer drug, or chemotherapeutic drug. The method involves contacting a cancer cell with (i) a solution comprising a peptide according to the first aspect of the invention and any one of an antineoplastic agent, an anticancer drug, or a chemotherapeutic drug; or (ii) a product according to the second, third, or fourth aspects of the invention that comprises any one of an antineoplastic agent, an anticancer drug, or a chemotherapeutic drug. The contacting of the cancer cell allows the cancer cell to take up the peptide or the product, and the antineoplastic agent, anticancer drug, or chemotherapeutic drug, and the peptide or product inhibits efflux of the antineoplastic agent, anticancer drug, or chemotherapeutic drug from the contacted cancer cell.

A fifteenth aspect of the invention relates to a method of treating a patient having cancer. The method involves administering to the patient an antineoplastic agent, an anticancer drug, or a chemotherapeutic drug; and administering to the patient a solution comprising a peptide according to the first aspect of the invention. The administering steps allows cancer cells to take up the peptide, or an oligomerization product formed by said peptide, and the antineoplastic agent, anticancer drug, or chemotherapeutic drug, and wherein the peptide or oligomerization product inhibits efflux of the antineoplastic agent, anticancer drug, or chemotherapeutic drug from cancer cells.

A sixteenth aspect of the invention relates to a method of treating a patient having cancer. The method includes administering to the patient a product according to the second, third, or fourth aspects of the invention that comprises any one of an antineoplastic agent, an anticancer drug, or a chemotherapeutic drug, wherein said administering allows cancer cells to take up the product, and the antineoplastic agent, anticancer drug, or chemotherapeutic drug, and wherein the product inhibits efflux of the antineoplastic agent, anticancer drug, or chemotherapeutic drug from cancer cells.

A seventeenth aspect of the invention relates to a method of treating an inflammatory eye condition. This method involves administering to the eye of an individual having an inflammatory eye condition a hydrogel product according to the fourth aspect of the invention in which a corticosteroid, preferably dexamethasone, is dispersed.

The accompanying Examples demonstrate that P5P modulates the oligomerization of a short nonapeptide derivative of a protein-protein interaction domain of ASC ("ASC$^{PYD}$") (i.e., Nap-FFKKFKLKL (SEQ ID NO:1), 1) (see Lu et al., "Unified Polymerization Mechanism for the Assembly of ASC-Dependent Inflammasomes," *Cell* 156 (6):1193-206 (2014); Moriya et al., "Role of Charged and Hydrophobic Residues in the Oligomerization of the PYRIN Domain of ASC," *Biochemistry* 44(2):575-83 (2005); and Lu et al., "Crystal Structure of the F27G AIM2 PYD Mutant and Similarities of its Self-Association to DED/DED Interactions," *J. Mol. Biol.* 426(7):1420-7 (2014), which are hereby incorporated by reference in their entirety). The Nap-FFKKFKLKL (SEQ ID NO:1) peptide identified in the accompanying examples self-assembles in aqueous solution to form helical nanofibrils. The addition of P5P to a solution of Nap-FFKKFKLKL (SEQ ID NO:1) results in the rapid hydrogelation of the peptide. Such sol-gel transition result from the formation of Schiff-bases and non-covalent interactions between the protonated ε-amine groups on the lysine residues and the phosphate group of P5P. The accompanying Examples further demonstrate that the use of other small bioactive molecules which bear either an aldehyde or a phosphate as the functional group (i.e., pyridoxal, folinic acid, ATP, and AMP) also results in rapid hydrogelation.

The Examples further demonstrate the generation and use of peptides bearing a nucleobase at the N-terminal of the peptide for selectively sequestering ATP. The data show that the assemblies (rather than monomers) of nucleopeptide (NP1), thyminyl-ffkkfklkl (containing D-amino acids), selectively sequester ATP over ADP in complex physiological conditions as evidenced by phase transition. Hexokinase (HK) and creatine phosphokinase (CPK) are able to control the cycle of ATP/ADP, thus modulating phase transition (from precipitate to solution and vice versa) and reversibly changing the morphologies of assemblies of NP1 and the nucleotides in PBS. Most importantly, NP1 exhibits selectivity towards ATP under physiological conditions, including in serum and in cells. Being incubated with multiple drug resistance cancer cells, NP1 slows down the efflux of an anticancer drug (e.g., doxorubicin, or Dox), resulting in long cellular retention of Dox and, thus, boosting the anti-cancer activity of Dox against Dox-resistance cancer cells. Five additional nucleopeptide analogs of NP1 were also demonstrated to differentiate ATP and ADP via either precipitation or gelation. As the first use of assemblies of small molecules for selectively sequestering ATP, this work opens up a new approach for rational design of supramolecular assemblies for sequestering (or recognizing) small biological molecules in complex physiological conditions to mimic the functions of proteins and to control cell behavior.

BRIEF DESCRIPTION OF THE DRAWINGS

FIG. 1 also illustrates a hydrogel formed by mixing 1 and P5P to provide covalent and non-covalent interactions.

FIG. 2A is a TEM image of a sample obtained by co-incubating co-MBP-ASC$^{PYD}$ with P5P (scale bar is 500 nm). FIG. 2B is a TEM image of a solution of 1 (scale bar is 20 nm). FIG. 2C is a TEM image of a hydrogel sample obtained by incubating the peptide 1 and 1 equivalent P5P (molar ratio) (scale bar is 20 nm).

FIG. 4A illustrates the molecular structures of bioactive molecules used to initiate gelation of 1, and TEM images of 1 (0.4 wt %) with addition of 1 or 4 equivalents (molar ratio) pyridoxal, folinic acid, ATP, or AMP in aqueous solution (pH=7.4). Scale bar is 20 nm for all TEM images.

FIG. 10A is a structure of a nucleopeptide (NP1) for selective ATP sequestration. FIG. 10B shows the interaction of assemblies of NP1 with ATP or ADP and the reversible phase transition of the assemblies controlled by a pair of counteracting enzymes. FIG. 10C shows a plausible mechanism of ATP sequestration by assemblies of NP1 in a multidrug resistance cell, thus slowing down drug efflux and boosting drug efficacy.

FIGS. 11A-C show TEM images of NP1 (0.4 wt %) in PBS buffer (pH 7.4) without (FIG. 11A) or with 1 equivalent of ATP (FIG. 11B) and ADP (FIG. 11C). Scale bar=50 nm. FIGS. 12D-E show the CD spectra of NP1 at 0.4 wt % (FIG. 11D) and 0.05 wt % (FIG. 11E) with or without ATP or ADP (equimolar with NP1).

FIGS. 12A-D show NP1 assemblies. FIGS. 12A-B show NP1 assemblies with ATP in the presence of glucose without or with addition of HK, respectively. FIGS. 12C-D show NP1 assemblies with ADP in the presence of Pcr without or with the addition of CPK, respectively. The concentration of NP1 is 0.4 wt %, equimolar ATP or ADP is added. All experiments are performed in 100 mm PBS buffer, pH 7.4 for 24 hours. Scale bar=100 nm.

FIG. 13A is a CSM image showing the inhibition of Dox efflux by NP1 in MES-SA/dx5 cells at 0 hours (changing to fresh medium without Dox after washing three times) and 5 h (further incubation after changing medium). Scale bar=20 mm. FIG. 13B shows MES-SA/dx5 cell viability after treatment with Dox, NP1 or the mixture of NP1 and Dox (5 mm) for 48 hours (n=3; ***, p<0.001). Bars shown are mean:SEM.

FIG. 14A shows TEM images of cell components collected from live cells without (control) or with the incubation of NP1 for 5 hours. Scale bar=100 nm. FIG. 14B shows ATP concentrations in the live cells incubated with NP1 (500 mm), NP1 plus Dox (10 mm), Dox (10 mm), and culture medium (n=3, the asterisks indicate the difference between 1 hour with 3 or 5 hours. ns, non-significant; *, p<0.05; **, p<0.01). Bars are mean: SEM. FIG. 14C shows CLSM images of MES-SA/dx5 cells incubated with Alexa-ATP and NP1-NBD (50 mm). Scale bar=5 mm.

DETAILED DESCRIPTION OF THE INVENTION

Figure 1:
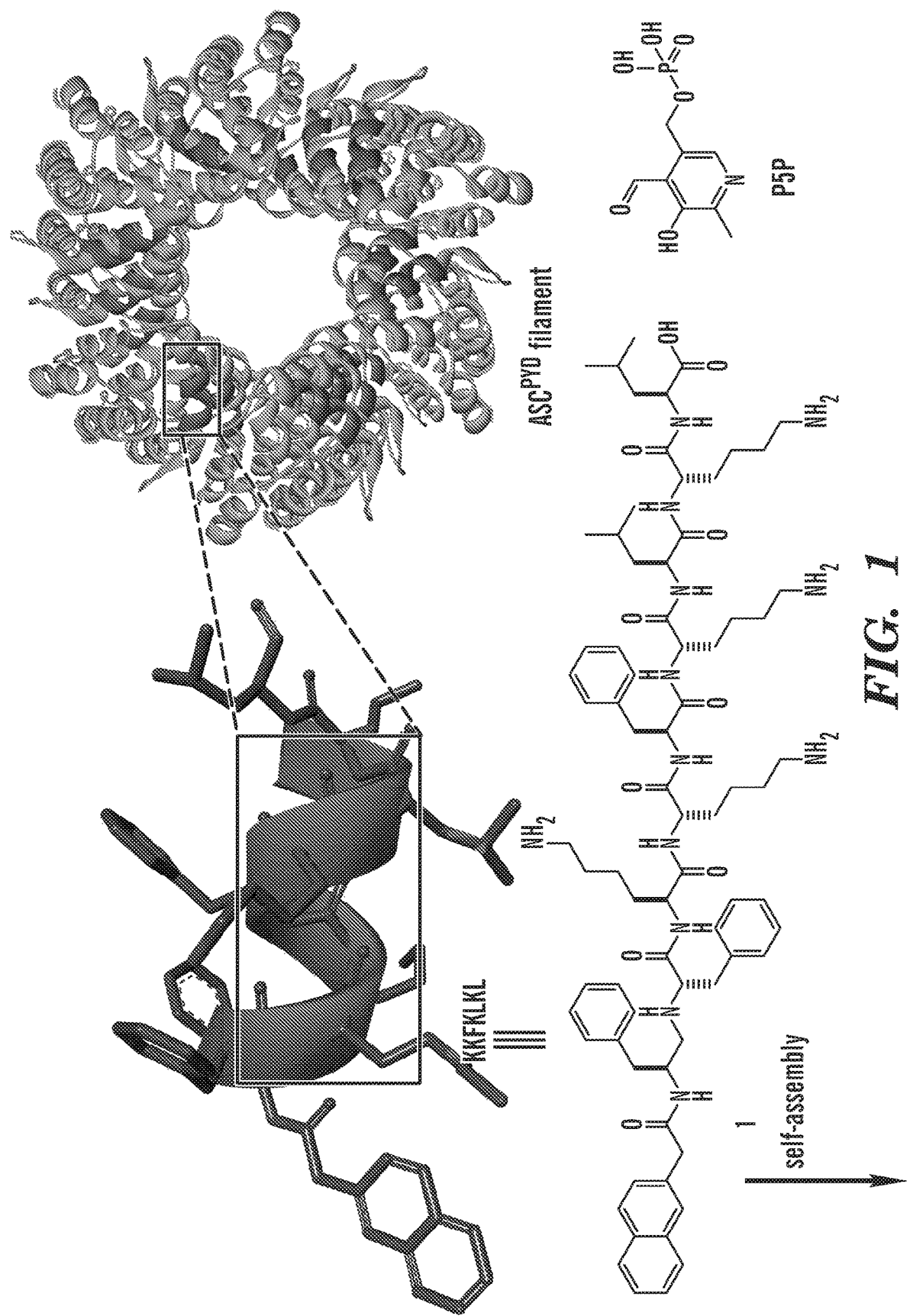
FIG. 1 is a schematic illustration of the molecular structure of 1, which contains the epitope KKFKLKL (SEQ ID NO: 2) from the cryo-EM structure of apoptosis-associated speck-like ("ASC") protein (Lu et al., "Unified Polymerization Mechanism for the Assembly of ASC-Dependent Inflammasomes," *Cell* 156(6):1193-206 (2014), which is hereby incorporated by reference in its entirety).
Figure 1:
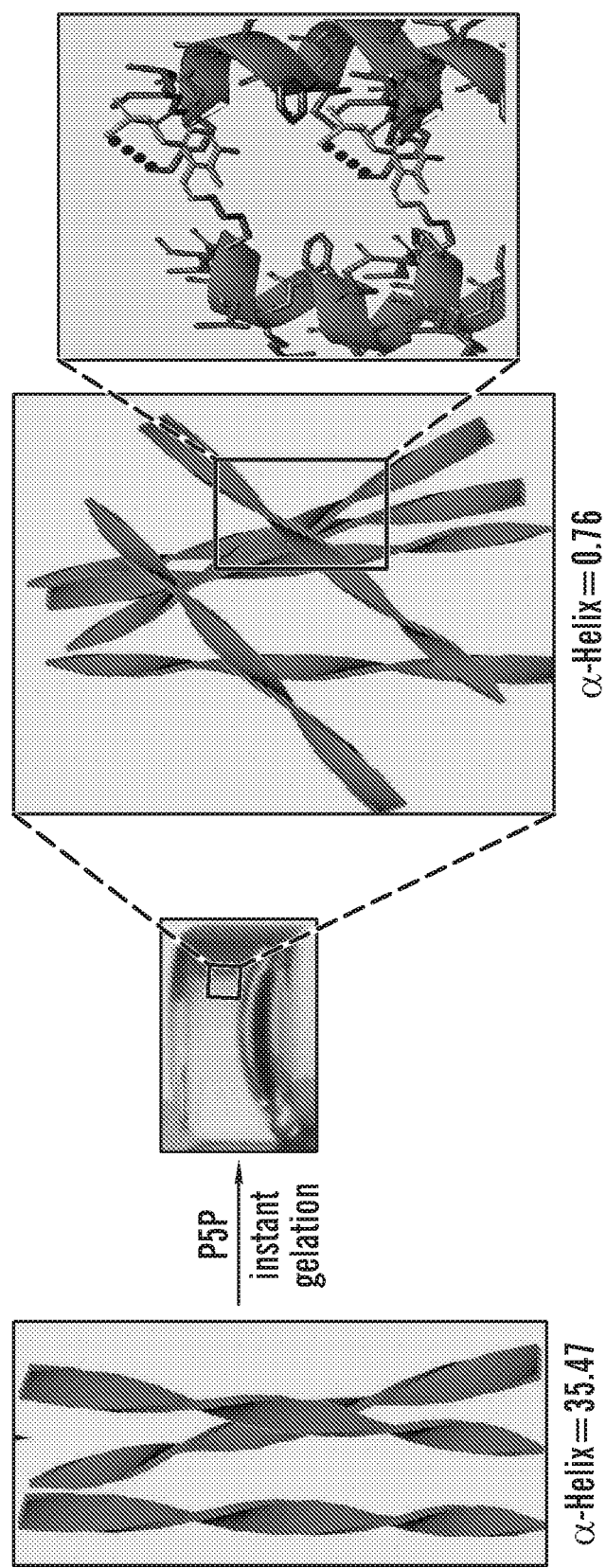

A first aspect of the invention relates to a peptide capable of induced self-assembly by a bioactive molecule comprising a (i) hydrogelation-promoting amino acid sequence and (ii) an oligomerization sequence.

The peptides of the present invention, upon exposure to a bioactive molecule, self-assemble into nanofibrils. As used herein, the term "nanofibril" is defined as a fiber of material having any shape wherein at least one dimension, e.g. the diameter, width, thickness, and the like, is about 100 nm or less. Nanofibril diameters may be about 50 nm or less, about 40 nm or less, about 30 nm or less, about 20 nm or less, about 10 nm or less, about 5 nm or less, about 4 nm or less, about 3 nm or less, about 2 nm or less, or about 1 nm or less in diameter. Although the peptides of the present invention, upon self-assembly, as described herein, form nanofibrils, persons of skill in the art should appreciate that such peptides may also form microfibrils that are larger than 100 nm thick.

As used herein, the term "bioactive molecule" refers to a molecule that exhibits biological activity. In some embodiments, the bioactive molecule is capable of forming a Schiff base and/or non-covalent interactions with the peptides of the present invention. Bioactive molecules include, without limitation, drugs, prodrugs, vitamins, and cofactors. Contacting the peptide with the bioactive molecule can be carried out in vitro or in vivo (e.g., in situ).

According to some embodiments, the bioactive molecule bears either an aldehyde or a phosphate as a functional group. Exemplary bioactive molecules include, without limitation, pyridoxal, pyridoxal-5-phosphate ("P5P"), folinic acid, nucleoside mono-, di-, and triphosphates such as adenosine monophosphate ("AMP"), diphosphate ("ADP"), and triphosphate ("ATP"), guanosine monophosphate ("GMP"), diphosphate ("GDP"), and triphosphate ("GTP"), cytidine monophosphate ("CTP"), diphosphate ("CDP"), and triphosphate ("CTP"), thymidine monophosphate ("TMP"), diphosphate ("TDP"), and triphosphate ("TTP"), uridine monophosphate ("UMP"), diphosphate ("UDP"), and triphosphate ("UTP"), phosphorylated amino acids such as tyrosine, serine, and threonine, phosphorylated drugs such as triamcinolone acetonide sodium phosphate and dexamethasone sodium phosphate, as well as any combinations thereof.

In one embodiment, the hydrogelation-promoting amino acid sequence is fused N-terminally to an oligomerization sequence. The oligomerization sequence may comprise: (i) (K/E/R)-(K/T/R)-(F/L)-(K/Q/R)-X-(K/H/Y)-L (SEQ ID NO: 98), where X is any amino acid, but preferably W/L/G/S/M/F/H; or (ii) (Z/E/R)-(Z/T/R)-(F/L)-(Z/Q/R)-X-(Z/H/Y)-L (SEQ ID NO: 99), where X is any amino acid, but preferably W/L/G/S/M/F/H, and Z is either K or a lysine residue whose sidechain is conjugated to a therapeutic agent. The oligomerization sequence may also comprise: (i) (L/F)-(K/E/R)-(K/T/R)-(F/L)-(K/Q/R)-X-(K/H/Y)-L (SEQ ID NO: 100), where X is any amino acid, but preferably W/L/G/S/M/F/H; or (ii) (L/F)-(Z/E/R)-(Z/T/R)-(F/L)-(Z/Q/R)-X-(Z/H/Y)-L (SEQ ID NO: 101), where X is any amino acid, but preferably W/L/G/S/M/F/H, and Z is either K or a lysine residue whose sidechain is conjugated to a therapeutic agent.

In some embodiments, the oligomerization sequence comprises at least two lysine residues. Alternatively, the oligomerization sequence is selected from the group consisting of: KKFKLKL (SEQ ID NO: 2) (human ASC, chain A), LKKFKLKL (SEQ ID NO: 3) (human ASC, chain A), KKFKMKL (SEQ ID NO: 4) (human ASC, chain Q), LKKFKMKL (SEQ ID NO: 5) (human ASC, chain Q), RKFKSKL (SEQ ID NO: 6) (zebrafish, ASC-like protein), LRKFKSKL (SEQ ID NO: 7) (zebrafish, ASC-like protein), KKFKGKL (SEQ ID NO: 8) (*Xenopus*, ASC-like protein), FKKFKGKL (SEQ ID NO: 9) (*Xenopus*, ASC-like protein), EKFKFKL (SEQ ID NO: 10) (Human Pyrin iso1), FEKFKFKL (SEQ ID NO: 11) (Human Pyrin iso1), KKLKFYL (SEQ ID NO: 12) (human Nalp10), FKKLKFYL (SEQ ID NO: 13) (human Nalp10), KTLKFHL (SEQ ID NO: 14) (mouse Nalp10), FKTLKFHL (SEQ ID NO: 15) (mouse Nalp10), KRFRHKL (SEQ ID NO: 16) (human Nlrp6), LKRFRHKL (SEQ ID NO: 17) (human Nlrp6), KKFQWHL (SEQ ID NO: 18) (zebrafish Nlrc3-like protein), and LKKFQWHL (SEQ ID NO: 19) (zebrafish Nlrc3-like protein).

As used herein, the term "amino acid" is intended to embrace all compounds, whether natural or synthetic, which include both an amino functionality and an acid functionality, including amino acid analogues and derivatives. In certain embodiments, the amino acids contemplated in the present invention are those naturally occurring amino acids found in proteins, or the naturally occurring anabolic or catabolic products of such amino acids, which contain amino and carboxyl groups. Amino acids, as used herein, may include both non-naturally and naturally occurring amino acids.

In some embodiments, the peptide comprises up to about 35 amino acids, including a plurality of aromatic amino acid residues. Aromatic amino acids used in the present invention include, without limitation, phenylalanine, phenylalanine derivatives, napthylalanine, napthylalanine derivative, tyrosine, tyrosine derivatives, tryptophan, and tryptophan derivatives.

The peptides can include all D-amino acids, all L-amino acids, or a mixture of L-amino acids and D-amino acids. As a consequence of utilizing entirely D-amino acids or a high proportion of D-amino acids, it is possible to render the peptide component protease resistant. In one embodiment, the peptide is resistant to a protease. In some embodiments, the protease is proteinase K.

In certain embodiments, the N-terminal amino acid may be covalently bound to a capping moiety. In one embodiment, the capping moiety comprises an acyl group. In another embodiment, the capping moiety further comprises an alkyl, aryl, or heteroaryl group. In some embodiments, the alkylacyl is acetyl or proprionyl, the arylacyl is 2-naphthalacetyl, phenylacetyl, fluorenyl-9-methoxycarbonyl, or pyrenylbutanoyl, cinnamoyl, and the heteroarylacyl is 3-((7-nitrobenzo(c)-1,2,5-oxadiazol-4-yl)amino)proprionyl or an acylated nucleobase. In accordance with this embodiment, the nucleobase may be selected from thyminyl, uracilyl, cytosinyl, adeninyl, and guaninyl. Such capping moieties can protect against enzymatic degradation of the peptide, as well as promote self-assembly in the case where aromatic groups are present in the capping moiety.

In some embodiments, where the capping moiety comprises an acyl group, the capping moiety may be selected from the group comprising a fluorophore, a chemotherapeutic agent, an antiangiogenic agent, a thermoablative nanoparticle, an immunomodulating agent, or an antigen.

Alternatively, the hydrogelation-promoting amino acid sequence includes an amino acid to which a therapeutic agent is conjugated. Introduction of functional groups or therapeutic agents to the peptide can also be achieved by coupling via side chains of amino acids, including the amino group of lysine, the guanidine group of arginine, the thiol group of cysteine, or the carboxylic acid group of glutamic acid or aspartic acid.

In general, amino groups present in lysine side chains, as well as the N-terminal amino group, can be reacted with reagents possessing amine-reactive functional groups using known reaction schemes. Exemplary amine-reactive functional groups include, without limitation, activated esters, isothiocyanates, and carboxylic acids. Therapeutic agents to be conjugated include those listed above. Examples of conjugating a chemotherapeutic agent (e.g., doxorubicin, daunorubicin, taxol) to a Lys sidechain are described in DeFeo-Jones et al., *Nature Med.* 6(11):1248-52 (2000), Schreier et al., *PlosOne* 9(4):e94041 (2014), Gao et al., *J Am Chem Soc.* 131:13576 (2009), each of which is hereby incorporated by reference in its entirety.

In general, guanidine groups present in arginine can be reacted with reagents possessing guanidine-reactive groups using known reaction schemes. Exemplary guanidine-reactive functional groups include, without limitation, NHS esters using gas phase synthesis (McGee et al., *J. Am. Chem. Soc.*, 134 (28):11412-11414 (2012), which is hereby incorporated by reference in its entirety).

In general, thiol groups present in cysteine (or cysteine derivative) side chains can be reacted with reagents possessing thiol-reactive functional groups using known reaction schemes. Exemplary thiol-reactive functional groups include, without limitation, iodoacetamides, maleimides, and alkyl halides. Reagents to be conjugated include those listed above.

In general, carboxyl groups present in glutamic or aspartic acid side chains, or at the C-terminal amino acid residue, can be reacted with reagents possessing carboxyl-reactive functional groups using known reaction schemes. Exemplary carboxyl-reactive functional groups include, without limitation, amino groups, amines, bifunctional amino linkers. Reagents to be conjugated include those listed above.

In each of the types of modifications described above, it should be appreciated that the conjugate can be directly linked via the functional groups of the peptide and the reagent to be conjugated, or via a bifunctional linker that reacts with both the peptide functional groups and the functional groups on the reagent to be conjugated.

According to one embodiment, the peptide is conjugated with a therapeutic agent of the type described hereinafter, particularly a chemotherapeutic agent, an antiangiogenic agent, an immunomodulating agent, or an antigen.

In some embodiments of the present invention, the hydrogelation-promoting amino acid sequence comprises CAP-F-F, CAP-F-F-K, CAP-f-f, CAP-f-f-k, CAP-F-F-K-F (SEQ ID NO: 20), or CAP-f-f-k-f, where CAP is a capping moiety that promotes self-assembly and gelation, e.g., naphthylacetyl, fluorenylmethyloxycarbonyl, pyrenylacetyl, thyminylacetyl, uracilylacetyl, cytosinylacetyl, adeninylacetyl, and guaninylacetyl, or similar structures.

The peptides of the present invention can have any length that is sufficient to allow for self-assembly by a bioactive molecule. This includes peptides up to about 35 amino acids, up to about 30 amino acids, up to about 25 amino acids, up to about 20 amino acids, up to about 15 amino acids, or up to about 10 amino acids. In certain embodiments, the peptides contain between 9 to 15 amino acids, 9 to 14 amino acids, 9 to 13 amino acids, 9 to 12 amino acids, or 9 to 11 amino acids.

Exemplary peptides of the present invention include, without limitation:

```
                              (SEQ ID NO: 1)
napthylacetyl-FFKKFKLKL, (SEQ ID NO: 21)
napthylacetyl-FFLKKFKLKL, (SEQ ID NO: 22)
napthylacetyl-FFKKFKMKL, (SEQ ID NO: 23)
napthylacetyl-FFLKKFKMKL, (SEQ ID NO: 24)
napthylacetyl-FFRKFKSKL, (SEQ ID NO: 25)
napthylacetyl-FFLRKFKSKL, (SEQ ID NO: 26)
napthylacetyl-FFKKFKGKL, (SEQ ID NO: 27)
napthylacetyl-FFFKKFKGKL, (SEQ ID NO: 28)
napthylacetyl-FFEKFKFKL, (SEQ ID NO: 29)
napthylacetyl-FFFEKFKFKL, (SEQ ID NO: 30)
napthylacetyl-FFKKLKFYL, (SEQ ID NO: 31)
napthylacetyl-FFFKKLKFYL, (SEQ ID NO: 32)
napthylacetyl-FFKTLKFHL, (SEQ ID NO: 33)
napthylacetyl-FFFKTLKFHL, (SEQ ID NO: 34)
napthylacetyl-FFKRFRHKL, (SEQ ID NO: 35)
napthylacetyl-FFLKRFRHKL, (SEQ ID NO: 36)
napthylacetyl-FFKKFQWHL, (SEQ ID NO: 37)
napthylacetyl-FFLKKFQWHL, (SEQ ID NO: 38)
napthylacetyl-FFKKKFKLKL, (SEQ ID NO: 39)
napthylacetyl-FFKLKKFKLKL, (SEQ ID NO: 40)
napthylacetyl-FFKKKFKMKL, (SEQ ID NO: 41)
napthylacetyl-FFKLKKFKMKL, (SEQ ID NO: 42)
napthylacetyl-FFKRKFKSKL, (SEQ ID NO: 43)
napthylacetyl-FFKLRKFKSKL, (SEQ ID NO: 44)
napthylacetyl-FFKKKFKGKL, (SEQ ID NO: 45)
napthylacetyl-FFKFKKFKGKL, (SEQ ID NO: 46)
napthylacetyl-FFKEKFKFKL, (SEQ ID NO: 47)
napthylacetyl-FFKFEKFKFKL, (SEQ ID NO: 48)
napthylacetyl-FFKKKLKFYL, (SEQ ID NO: 49)
napthylacetyl-FFKFKKLKFYL, (SEQ ID NO: 50)
napthylacetyl-FFKKTLKFHL,
``` napthylacetyl-FFKFKTLKFHL, (SEQ ID NO: 51)

napthylacetyl-FFKKRFRHKL, (SEQ ID NO: 52)

napthylacetyl-FFKLKRFRHKL, (SEQ ID NO: 53)

napthylacetyl-FFKKKFQWHL, (SEQ ID NO: 54)

napthylacetyl-FFKLKKFQWHL, (SEQ ID NO: 55)

napthylacetyl-FFKFKKFKLKL, (SEQ ID NO: 56)

napthylacetyl-FFKFLKKFKLKL, (SEQ ID NO: 57)

napthylacetyl-FFKFKKFKMKL, (SEQ ID NO: 58)

napthylacetyl-FFKFLKKFKMKL, (SEQ ID NO: 59)

napthylacetyl-FFKFRKFKSKL, (SEQ ID NO: 60)

napthylacetyl-FFKFLRKFKSKL, (SEQ ID NO: 61)

napthylacetyl-FFKFKKFKGKL, (SEQ ID NO: 62)

napthylacetyl-FFKFFKKFKGKL, (SEQ ID NO: 63)

napthylacetyl-FFKFEKFKFKL, (SEQ ID NO: 64)

napthylacetyl-FFKFFEKFKFKL, (SEQ ID NO: 65)

napthylacetyl-FFKFKKLKFYL, (SEQ ID NO: 66)

napthylacetyl-FFKFFKKLKFYL, (SEQ ID NO: 67)

napthylacetyl-FFKFKTLKFHL, (SEQ ID NO: 68)

napthylacetyl-FFKFFKTLKFHL, (SEQ ID NO: 69)

napthylacetyl-FFKFKRFRHKL, (SEQ ID NO: 70)

napthylacetyl-FFKFLKRFRHKL, (SEQ ID NO: 71)

napthylacetyl-FFKFKKFQWHL, (SEQ ID NO: 72)

napthylacetyl-FFKFLKKFQWHL, (SEQ ID NO: 73)

napthylacetyl-ffKKFKLKL, napthylacetyl-ffLKKFKLKL, napthylacetyl-ffKKFKMKL, napthylacetyl-ffLKKFKMKL, napthylacetyl-ffRKFKSKL, napthylacetyl-ffLRKFKSKL, napthylacetyl-ffKKFKGKL, napthylacetyl-ffFKKFKGKL, napthylacetyl-ffEKFKFKL, napthylacetyl-ffFEKFKFKL, napthylacetyl-ffKKLKFYL, napthylacetyl-ffFKKLKFYL, napthylacetyl-ffKTLKFHL, napthylacetyl-ffFKTLKFHL, napthylacetyl-ffKRFRHKL, napthylacetyl-ffLKRFRHKL, napthylacetyl-ffKKFQWHL, napthylacetyl-ffLKKFQWHL, napthylacetyl-ffKKKFKLKL, napthylacetyl-ffkLKKFKLKL, napthylacetyl-ffKKKFKMKL, napthylacetyl-ffkLKKFKMKL, napthylacetyl-ffRKFKSKL, napthylacetyl-ffkLRKFKSKL, napthylacetyl-ffKKKFKGKL, napthylacetyl-ffkFKKFKGKL, napthylacetyl-ffkEKFKFKL, napthylacetyl-ffkFEKFKFKL, napthylacetyl-ffKKKLKFYL, napthylacetyl-ffkFKKLKFYL, napthylacetyl-ffkKTLKFHL, napthylacetyl-ffkFKTLKFHL, napthylacetyl-ffkKRFRHKL, napthylacetyl-ffkLKRFRHKL, napthylacetyl-ffkKKFQWHL, napthylacetyl-ffkLKKFQWHL, napthylacetyl-ffkKKFKLKL, napthylacetyl-ffkLKKFKLKL, napthylacetyl-ffkKKFKMKL, napthylacetyl-ffkfLKKFKNIKL, napthylacetyl-ffkfRKFKSKL, napthylacetyl-ffkfLRKFKSKL, napthylacetyl-ffkfKKFKGKL, napthylacetyl-ffkfFKKFKGKL, napthylacetyl-ffkfEKFKFKL, napthylacetyl-ffkfFEKFKFKL, napthylacetyl-ffkfKKLKFYL,

```
napthylacetyl-ffkfFKKLKFYL,
napthylacetyl-ffkfKTLKFHL,
napthylacetyl-ffkfFKTLKFHL,
napthylacetyl-ffkfKRFRHKL,
napthylacetyl-ffkfLKRFREKL,
napthylacetyl-ffkfKKFQWHL,
napthylacetyl-ffkfLKKFQWHL,
thyminylacetyl-ffkkfklkl (NP1),
                                   (NP2, SEQ ID NO: 74)
thyminylacetyl-FFKKFKLKL,
thyminylacetyl-ffkkfkl (NP3),
                                   (NP4, SEQ ID NO: 75)
thyminylacetyl-FFKKFKL,
thyminylacetyl-ffkkf (NP5),
                                   (NP6, SEQ ID NO: 76)
thyminylacetyl-FFKKF,
thyminylacetyl-ffrrfrlrl (NP1/r),
                                   (SEQ ID NO: 81)
thyminylacetyl-FFRRFRLRL,
uracilylacetyl-ffkkfklkl,
                                   (SEQ ID NO: 82)
uracilylacetyl-FFKKFKLKL,
uracilylacetyl-ffkkfkl,
                                   (SEQ ID NO: 83)
uracilylacetyl-FFKKFKL,
uracilylacetyl-ffkkf,
                                   (SEQ ID NO: 84)
uracilylacetyl-FFKKF,
uracilylacetyl-ffrrfrlrl,
                                   (SEQ ID NO: 85)
uracilylacetyl-FFRRFRLRL,
cytosinylacetyl-ffkkfklkl,
                                   (SEQ ID NO: 86)
cytosinylacetyl-FFKKFKLKL,
cytosinylacetyl-ffkkfkl,
                                   (SEQ ID NO: 87)
cytosinylacetyl-FFKKFKL,
cytosinylacetyl-ffkkf,
                                   (SEQ ID NO: 88)
cytosinylacetyl-FFKKF,
cytosinylacetyl-ffrrfrlrl,
                                   (SEQ ID NO: 89)
cytosinylacetyl-FFRRFRLRL,
adeninylacetyl-ffkkfklkl,
                                   (SEQ ID NO: 90)
adeninylacetyl-FFKKFKLKL,
adeninylacetyl-ffkkfkl,
                                   (SEQ ID NO: 91)
adeninylacetyl-FFKKFKL,
adeninylacetyl-ffkkf,
                                   (SEQ ID NO: 92)
adeninylacetyl-FFKKF,
adeninylacetyl-ffrrfrlrl,
                                   (SEQ ID NO: 93)
adeninylacetyl-FFRRFRLRL,
guaninylacetyl-ffkkfklkl,
                                   (SEQ ID NO: 94)
guaninylacetyl-FFKKFKLKL,
guaninylacetyl-ffkkfld,
                                   (SEQ ID NO: 95)
guaninylacetyl-FFKKFKL,
guaninylacetyl-ffkkf,
                                   (SEQ ID NO: 96)
guaninylacetyl-FFKKF,
guaninylacetyl-ffrrfrlrl,
and
                                   (SEQ ID NO: 97)
guaninylacetyl-FFRRFRLRL.
```

To the extent that specific embodiments are not otherwise listed above, it is explicitly contemplated that each of the peptides listed above as containing L-amino acids can also be prepared in the form of its D-amino acid enantiomer. For each peptide listed above as containing a mixture of L- and D-amino acids, it is also explicitly contemplated that each of those peptides can be prepared in the form containing only L-amino acids or only D-amino acids.

A further aspect of the invention relates to a product formed by exposing the peptide according to the first aspect of the invention to a bioactive molecule that induces oligomerization and hydrogelation. Exemplary bioactive molecules are described above. According to one embodiment, the peptide has an alpha-helix structure prior to the exposing step, and a random structure after the exposing step.

In certain embodiments, the self-assembled product is in the form of an oligomerized product that includes two or more peptides of the invention in activated form. The activated peptides co-assemble during oligomerization and hydrogelation. Preferably, each of the two or more peptides have an alpha-helix structure prior to activation, and a random structure when activated.

In certain embodiments, the oligomerization and hydrogelation occurs in an aqueous environment, in which case the resulting product takes the form of a supramolecular hydrogel formed upon self-assembly of the activated peptide(s) of the invention in an aqueous medium. As described herein, the term "supramolecular hydrogel" refers to a network of nanofibers formed by the self-assembly of small molecules (i.e., hydrogelators) as the solid phase to encapsulate water (Du et al., *Chem. Asian J.* 9(6):1446-1472 (2014), which is hereby incorporated by reference in its entirety).

In certain embodiments, the supramolecular hydrogel may also comprise one or more therapeutically effective compounds. Therapeutically effective compounds include proteins, glycosaminoglycans, glycoproteins, carbohydrates, nucleic acids, inorganic and organic biologically active compounds.

Exemplary therapeutically effective compounds include, without limitation, antigens, enzymes, antibiotics or antimicrobials (antibacterial, antifungal, antiviral, antiprotozoan), antineoplastic agents, local anesthetics, hormones, angiogenic agents, anti-angiogenic agents, growth factors, antibodies, neurotransmitters, psychoactive drugs, anticancer drugs, chemotherapeutic drugs, drugs affecting reproductive organs, genes, anti-inflammatory drugs, analgesics, antiproliferatives, anti-fibrotics, and oligonucleotides.

A further aspect of the invention relates to a pharmaceutical composition comprising a pharmaceutically acceptable carrier and a peptide or activated/oligomerized product of the invention.

According to one embodiment, two or more of the peptides are present.

In some embodiments, the carrier is an aqueous medium. In one embodiment, the aqueous medium is a sterile isotonic aqueous buffer, which is typically well tolerated for administration to an individual. Additional exemplary aqueous media include, without limitation, normal saline (about 0.9% NaCl), phosphate buffered saline ("PBS"), sterile water/distilled autoclaved water ("DAW"), as well as cell growth medium (e.g., MEM, with or without serum), aqueous solutions of dimethyl sulfoxide ("DMSO"), polyethylene glycol ("PEG"), and/or dextran (less than 6% per by weight.)

To improve patient tolerance to administration, the pharmaceutical composition may have a pH of about 5 to about 8. In one embodiment, the pharmaceutical composition has a pH of about 6.5 to about 7.4. In some embodiments, the sodium hydroxide or hydrochloric is added to the pharmaceutical composition to adjust the pH.

In other embodiments, the pharmaceutical composition includes a weak acid or salt as a buffering agent to maintain pH. Citric acid has the ability to chelate divalent cations and can thus also prevent oxidation, thereby serving two functions as both a buffering agent and an antioxidant stabilizing agent. Citric acid is typically used in the form of a sodium salt, typically 10-500 mM. Other weak acids or their salts can also be used.

The pharmaceutical composition may also include solubilizing agents, preservatives, stabilizers, emulsifiers, and the like. A local anesthetic (e.g., lidocaine, benzocaine, etc.) may also be included in the compositions, particularly for injectable forms, to ease pain at the site of the injection.

In some embodiments, the peptide or peptides may each be present at a concentration of about 1 µM to about 10 mM, about 10 µM to about 5 mM, about 50 µM to about 2 mM, or about 100 µM to about 1 mM. The volume of the composition administered, and thus, dosage of the peptide administered can be adjusted by one of skill in the art to achieve optimized results. In one embodiment, between 100 and about 800 µg can be administered per day, repeated daily or periodically (e.g., once every other day, once every third day, once weekly). This can be adjusted lower to identify the minimal effective dose, or tailored higher or lower according to the nature of the treatment being effected.

The compositions of the present invention may further comprise a therapeutically effective compound of the type described above.

Additional aspects of the invention relate to administering one or more peptides or compositions or hydrogels of the invention to a subject to promote a desired effect. In these various embodiments, administering may be carried out topically, intraperitoneally, intralesionally, ocularly, intraocularly, intranasally, orally, rectally, transmucosally, intranasally, intradermally, intestinally, parenterally, intramuscularly, subcutaneously, intravenously, intraarterially, intramedullary by implantation, by intracavitary or intravesical instillation, intrathecally, as well as direct intraventricular, intraperitoneal, intrasynovially, by intraocular injection, or by introduction into one or more lymph nodes. Administration can be repeated periodically during the course of a treatment regimen, for example, one or more times per week, daily, or even one or more times per day.

In certain embodiments, a bioactive activator of the type described above can be co-administered to induce peptide activation in situ. The bioactive activator may comprise one or more of the bioactive molecules described previously.

In some embodiments, the subject is a mammal. Suitable mammals include, without limitation, rodents, rabbits, canines, felines, ruminants, and primates such as monkeys, apes, and humans. In one embodiment, the subject is a human.

The products and compositions of the present invention afford a number of uses.

In one aspect, the invention relates to a drug delivery vehicle suitable for delivering a therapeutic agent to an individual in need thereof.

According to one embodiment, the method of delivering a therapeutic agent to an individual includes administering to the individual a product or oligomerized product (or hydrogel) of the invention, which contained a therapeutic agent, whereby the therapeutic agent is released from the product to the body of the individual after administration thereof.

According to another embodiment, the method of delivering a therapeutic agent to an individual includes administering to the individual a pharmaceutical composition of the invention, which contains the therapeutic agent, and administering a bioactive activator to the site where the pharmaceutical composition is administered to induce in situ oligomerization and hydrogelation of the peptide, whereby the therapeutic agent is subsequently released from the in situ formed hydrogel to the body of the individual. Administration of the bioactive activator can be carried out prior to administration of the pharmaceutical composition, after administration of the pharmaceutical composition, or substantially at the same time.

In another aspect, the invention relates to a method of promoting would healing.

According to one embodiment, this involves administering to a wound of a subject a therapeutically effective amount of a peptide or pharmaceutical composition of the invention, where the administering is effective to activate the peptide and induce oligomerization of the activated peptide to form a hydrogel at the wound site. The bioactive activator is preferably administered to the wound site prior to administration of the peptide or pharmaceutical composition, after administration of the peptide or pharmaceutical composition, or substantially at the same time.

According to another embodiment, this involves administering to the individual a product or oligomerized product (or hydrogel) of the invention, whereby the presence of the product at the wound site promotes healing of the wound.

The wound may be a topical wound or a burn wound. Alternatively, the wound is an internal wound. In one embodiment, the wound is an ocular wound.

The wound may also be one that is closed with one or more of an adhesive, a suture, a staple, or a tape. Alternatively, the wound is an open wound. The hydrogel can also be administered in the form of a wound dressing, which may or may not be a shaped wound dressing.

According to one embodiment, the peptide is conjugated with a therapeutic agent selected from the group consisting of an antimicrobial agent, antibacterial agent, antifungal agent, antiviral agent, immunomodulating agent, or an antigen.

According to another embodiment, the pharmaceutical composition is administered or co-administered with a therapeutic agent selected from the group consisting of an antimicrobial agent, antibacterial agent, antifungal agent, antiviral agent, immunomodulating agent, or an antigen.

According to a further embodiment, the hydrogel is loaded with an effective amount of a therapeutic agent selected from the group consisting of an antimicrobial agent, antibacterial agent, antifungal agent, antiviral agent, immunomodulating agent, or an antigen.

In another aspect, the invention relates to a method of promoting an immune response in an individual.

According to one embodiment, the method of inducing an immune response involves administering to an individual a therapeutically effective amount of a pharmaceutical composition of the invention that contains an antigen of interest, where the administering is effective to activate the peptide and induce oligomerization of the activated peptide at the site of administration, and to induce an immune response against the antigen released from the activated/oligomerized product. Administration of the bioactive activator can be carried out prior to administration of the pharmaceutical composition, after administration of the pharmaceutical composition, or substantially at the same time.

According to another embodiment, this involves administering to the individual a product or oligomerized product (or hydrogel) of the invention, which is loaded with the antigen of interest, where the administration of the antigen by the product/hydrogel is effective to induce an immune response against the antigen.

Optionally, the pharmaceutical composition or product/hydrogel of the invention is pre-loaded with an effective amount of an immunomodulating agent such as an adjuvant. Numerous adjuvants are known in the art, and persons of skill in the art can select appropriate adjuvants depending on the antigen of interest and the type of immune response to be generated, e.g., a T-cell mediated or B-cell mediated immune response. In one embodiment, the peptide is conjugated with a therapeutic agent selected from the group consisting of an immunomodulating agent or an antigen. Numerous examples of each of these categories are well known in the art.

According to another aspect, the invention relates to a method of treating a patient for cancer or inhibiting cancer cell efflux of an antineoplastic agent, anticancer drug, or chemotherapeutic drug.

The cancer cells to be treated in accordance with these aspects can be present in a solid tumor, present as a metastatic cell, or present in a heterogenous population of cells that includes both cancerous and noncancerous cells. Exemplary cancer conditions include, without limitation, cancers or neoplastic disorders of the brain and CNS (glioma, malignant glioma, glioblastoma, astrocytoma, multiforme astrocytic gliomas, medulloblastoma, craniopharyngioma, ependymoma, pinealoma, hemangioblastoma, acoustic neuroma, oligodendroglioma, meningioma), pituitary gland, breast (Infiltrating, Pre-invasive, inflammatory cancers, Paget's Disease, Metastatic and Recurrent Breast Cancer), blood (Hodgkin's Disease, Leukemia, Multiple Myeloma, Lymphoma), lymph node cancer, lung (Adenocarcinoma, Oat Cell, Non-small Cell, Small Cell, Squamous Cell, Mesothelioma), skin (melanoma, basal cell, squamous cell, Kapsosi's Sarcoma), bone cancer (Ewing's Sarcoma, Osteosarcoma, Chondrosarcoma), head and neck (laryngeal, pharyngeal, and esophageal cancers), oral (jaw, salivary gland, throat, thyroid, tongue, and tonsil cancers), eye, gynecological (Cervical, Endrometrial, Fallopian, Ovarian, Uterine, Vaginal, and Vulvar), genitourinary (Adrenal, bladder, kidney, penile, prostate, testicular, and urinary cancers), and gastrointestinal (appendix, bile duct (extrahepatic bile duct), colon, gallbladder, gastric, intestinal, liver, pancreatic, rectal, and stomach cancers).

While any class of antineoplastic agent, anticancer drug, or chemotherapeutic drug is contemplated for use in connection with the present invention, exemplary agents within these classes include alkylating agents, platinum drugs, antimetabolites, anthracycline and non-anthracycline antitumor antibiotics, topoisomerase inhibitors, and mitotic inhibitors, corticosteroids and targeted cancer therapies (such as imatinib, Gleeve®; gefitinib, Iressa®; sunitinib, Sutent®; and bortezomib, Velcade®).

According to one embodiment, the method of treating cancer includes administering to the patient an antineoplastic agent, an anticancer drug, or a chemotherapeutic drug; and administering to the patient a solution comprising a peptide of the invention. These steps of administering the agents/drugs and peptide allows cancer cells to take up the peptide, or an oligomerization product formed by the peptide, and the administered agents/drugs. In certain embodiments, this method also includes co-administering a bioactive activator to a site of peptide administration to induce peptide activation and oligomerization. Administration can be carried out in the manner described above.

As a consequence of administering the agents/drugs and peptide, and optionally the bioactive activator, the peptide or oligomerization product inhibits efflux of the antineoplastic agent, anticancer drug, or chemotherapeutic drug from cancer cells.

According to another embodiment, the method of treating cancer includes administering to the patient a product (formed by exposing a peptide of the invention to a bioactive molecule) or oligomerized product that comprises, and is formed in the presence of, any one of an antineoplastic agent, an anticancer drug, or a chemotherapeutic drug. Thus, these materials are pre-formed outside the body, and introduced in the formed of, e.g., a hydrogel in which the agents/drugs are retained. As a result of administering the product or oligomerized product, cancer cells take up the product or oligomerization product, and the agents/drugs contained therein, and the product or oligomerization product inhibits efflux of agents/drugs from cancer cells. Administration can be carried out in the manner described above, particularly by intraperitoneal or intratumoral administration.

Based on the foregoing description, and as evidenced by the Examples, a further aspect of the invention relates to a method of inhibiting cancer cell efflux of an antineoplastic agent, anticancer drug, or chemotherapeutic drug. These methods include contacting a cancer cell with either (i) a solution comprising a peptide of the invention (and optionally a bioactive agent, if not otherwise present in the cancer cells) and any one of an antineoplastic agent, an anticancer drug, or a chemotherapeutic drug; or (ii) a product or oligomerized product of the invention that comprises any one of an antineoplastic agent, an anticancer drug, or a chemotherapeutic drug. As a result of such contacting, the cancer cell are allowed to take up the peptide or the product or oligomerized product, and the antineoplastic agent, anticancer drug, or chemotherapeutic drug, and the peptide inhibits efflux of the antineoplastic agent, anticancer drug, or chemotherapeutic drug from the contacting cancer cell.

The mechanism of action for this method involves contacting and binding (or sequestering) of ATP by the bioactivated peptide (i.e., the product or oligomerized product of the invention). The contacting of the ATP may occur in a cell, including a cancer cell of the type described above, that is located ex vivo or in vivo.

This same method of action can be carried out in a cell free assay format, where ATP is sequestered in vitro in a cell-free solution, or in a cell-based assay format, where cells are located ex vivo.

EXAMPLES

The examples below are intended to exemplify the practice of embodiments of the disclosure but are by no means intended to limit the scope thereof.

Materials & Methods for Examples 1-12

Hydrogel Preparation: Compound 1 (5.0 mg) was dissolved in 1 mL of aqueous buffer (sodium hydroxide was used to adjust the final pH to 7.4), and the hydrogels were formed after the addition of different equivalents of small molecules (initial concentration is 100 mM), the final concentration of 1 is 0.4 wt % in all hydrogels. The gelation time of 1 with different bioactive small molecules was determined by vial inverse method.

TEM Sample Preparation: The hydrogel was placed on glow discharge thin carbon-coated copper grids (400 meshes, Pacific Grid-Tech) and incubated for 30 s at room temperature. 30 seconds later, a large drop of the ddH$_2$O was placed on parafilm and the grid was allowed to touch the water drop with the sample-loaded surface facing the parafilm. The grid was tilted and allowed to gently absorb water from the edge of the grid using a filter paper sliver (repeated 3 times). Immediately after rinsing, staining was performed by placing a large drop of the UA (uranyl acetate, 2% v/v) stain solution on parafilm and allowing the grid to touch the stain solution drop with the sample-loaded surface facing the parafilm. The grid was tilted and allowed to gently absorb the stain solution from the edge of the grid using a filter paper sliver. The grid was air dried and then examined as soon as possible.

Statistical Analysis of the Fibril Diameters: Using ImageJ Software and obtained TEM images, fiber diameters were measured from each image. Mean and SD of the fibers was obtained from multiple fiber measurements (80) on each TEM image.

Rheology Experiments: The rheological tests were performed on TA ARES-G2 rheometer, parallel-plate geometry with an upper plate diameter of 25 mm and a gap of 0.4 mm. During the measurement, the stage temperature was maintained at 25° C. by Peltier heating/cooling system. The hydrogel was loaded into stage by spatula. For the rheology testing in Examples 1-7, a time sweep was performed at the frequency of 6.28 rad/s and the strain for 1.0%, and a frequency sweep was performed at the range of 0.1 to 200 rad/s and strain is 1.0%. For the rheology testing in Examples 8-12, a strain sweep (0.1% to 100%) was performed at the frequency of 6.28 rad/s, and a frequency sweep was performed at the range of 0.1 to 200 rad/s and strain is 1.0%.

Circular Dichroism Measurement: For Examples 1-7, CD spectra were recorded (185-300 nm) using a JASCO 810 spectrometer under a nitrogen atmosphere. The hydrogel (0.4 wt %, 200 μL) was placed evenly on the 1 mm thick quartz cuvette and scanned with 0.1 nm interval for three times. For Examples 8-12, CD spectra were recorded (185-230 nm) using a JASCO 810 spectrometer under a nitrogen atmosphere. The nucleopeptide (200 μL, different concentrations) without or with ATP was placed evenly on the 1 mm thick quartz cuvette and scanned with 0.1 nm interval for three times. The percentage of secondary structures in different samples was calculated by the programs provided in DichroWeb.

Fluorescent Spectrum: The emission spectra were recorded on Shimadzu RF-5301-PC fluorescence spectrophotometer. The hydrogel (0.4 wt %, 1 mL) was introduced into 10*10 mm quartz cuvette and the excitation wavelength was set to 272 nm, and emissions from 290 nm to 500 nm were scanned three times with 1 nm interval.

Fourier Transform Infrared (FTIR) Spectroscopy: FTIR Spectra were recorded on a Nicolet IR200 spectrometer (Thermo Scientific). The samples were spread directly on the surface of the trough plate. Spectra were acquired in the 4000-600 cm-1 range with a resolution of 2 cm-1 over 64 scans. The same aqueous solution spectrum was used as background and subtracted from all spectra.

Sample Preparation and Process for Sequestering ATP by Nucleopeptide: Typically, nucleopeptide (5.0 mg) was dissolved in 1 mL of PBS buffer. A minimal amount of sodium hydroxide was used to adjust the final pH to 7.4 to form 5.0 wt % solution of the nucleopeptide. ATP or ADP was dissolved in PBS buffer at the concentration of 100 mM with the final pH of 7.4. To test sequestration ability of nucleopeptide, we mixed the solution of 5.0 wt % of nucleopeptide with ATP (ADP) in different molar ratio and stirred the mixture with pipettor gently. The mixture was kept at room temperature and used for different characterizations. The sequestration of ATP (or ADP) results in phase transition, from the solution to precipitates or hydrogel, which is observable by naked eyes. Such phase transitions were further characterized by TEM, CD, SLS and rheology according to the same procedure for sample preparation.

Static Light Scattering: Static light scattering was performed on an ALV (Langen, Germany) goniometer and correlator system with a 22 mW HeNe (λ=633 nm) laser and an avalanche photodiode detector. Before each test, we used detergent to clean the tubes for SLS testing. NP1 was prepared at the concentration range from 0.025 wt % to 0.4 wt % in PBS buffer (pH=7.4) without or with addition of 1 molar ratio of ATP or ADP. To examine the effects of different molar ratio of ATP (ADP) on assemblies of NP1, the concentration of NP1 was maintained at 0.4 wt %, and a different molar ratio of ATP (or ADP) was added. The static light scattering was tested at 30 degree with 1.5 mL sample in the tube. The resulting intensity ratios are proportional to the amount of aggregates in the samples.

ATP/ADP Cycle in the Presence of NP1: To set up the ATP/ADP cycle in the presence of NP1, two pathways were selected to fulfill this cycle. The first pathway starts from the mixture of NP1 and ATP. After the formation of precipitate by NP1 (0.4 wt %) and ATP (1 molar ratio of NP1, in PBS buffer contains 60 mM Glucose), 20 U/mL of hexokinase was added for 24 h and the precipitate can be seen to transfer to solution. Next, 100 μL of 50 mM of phosphocreatine and 60 U/mL of phosphokinase was added to the above solution for 24 h, and the solution changed back to precipitate. The second pathway starts from the mixture of NP1 and ADP. Addition of 1 molar ratio of ADP to the solution of NP1 (final concentration is 0.4 wt %, PBS buffer contains 50 mM of phosphocreatine) for 24 h, and then creatine phosphokinase (18 U/mL) was added to the above solution for 24 h. Formation of precipitate from the solution was observed.

Next, 100 µL of 60 mM glucose and 50 U/mL of hexokinase were added to the above solution for 24 h, and the precipitate can be seen to transfer to solution.

Cell culture and MTT assay: Cell culture was carried out with MES-SA/dx5 cells purchased from Sigma-Aldrich Corporation. These cells were cultured in Macyo's 5A medium supplemented with 10% v/v fetal bovine serum, 100 U/mL penicillin and 100 µg/mL streptomycin. The condition for cell culture was 37° C. in a humidified atmosphere of 5% $CO_2$. The MTT assay was carried out using MES-SA/dx5 cells seeded in a 96-well plate with a density of $1*10^4$ cells per-well (total medium volume of 100 µL). 24 hours post seeding, after the removal of the medium, solutions with serial of concentrations (5 concentrations) of different nucleopeptides were added to each well. Cells without the treatment of the precursors were used as the control. At designated time (24/48/72 hours), 10 µL MTT solution (5 mg/mL) was added to each well and incubated at 37° C. for another 4 h, and then 100 µL of SDS-HCl solution was added to stop the reduction reaction and dissolve the purple formazan. The absorbance of each well at 595 nm was measured by a multimode microplate reader. The cytotoxicity assay was performed three times and the average value of the three measurements was taken. All the statistical analysis used mean±SEM. The range of SEM is from 0.04 to 2.21.

Confocal Laser Scanning Microscopy (CLSM) Images of the Inhibition of Efflux Pump: To determine the potential drug efflux inhibitory effect by nucleopeptides, the drug efflux of free DOX was evaluated without or with incubation with nucleopeptide in efflux pumps overexpressing MES-SA/dx5 cells. After seeding $1.5 \times 10^5$ cells into 3.5 cm confocal dish and incubating at 37° C. for 24 h, the cells were incubated either with 10 µM free Dox or Dox with different concentration of nucleopeptide for 4 h. Then the medium was removed and the cells were washed three times with culture medium, and subsequently incubated with fresh complete medium for different time intervals (0, 2 or 5 h). At the end of incubation time, the cells were washed twice by live cell imaging buffer and stained nucleus by Hoechst 33342 for 10 minutes. After washed twice by live cell imaging, the cells were imaged immediately by Zeiss 880 microscope at the lens of 60×.

Luminescent ATP Detection Assay: Luminescent ATP detection assay kit was obtained from Abcam (Ab113849, U.S.A) and carried out according to the supplied instructions. Briefly, MES-SA/dx5 cells at the density of $1.0 \times 10^4$ were seeded onto 96-well plate in 100 µL medium. After the growth of MES-SA/dx5 cells in cell incubator for 24 h, the culture medium was removed and doxorubicin was added at the designed concentration without or with NP1 in medium. Untreated cells and blank well (without cells) with cell culture medium as positive control and background luminescence level. At desired times, 50 µL of detergent was added to the wells containing 100 µL of cultured cell medium. Shaking the plate for 5 minutes was carried out in an orbital shaker at 600-700 rpm to lyse the cells and stabilize the ATP. Thereafter, 50 µL of reconstituted substrate solution was added to each of the wells and shaking continued for 5 minutes in the orbital shaker at 600-700 rpm. The plate was covered for 10 minutes, and then read using a luminometer.

Example 1—P5P Modulates the Oligomerization of MBP-$ASC^{PYD}$

Figure 2A:
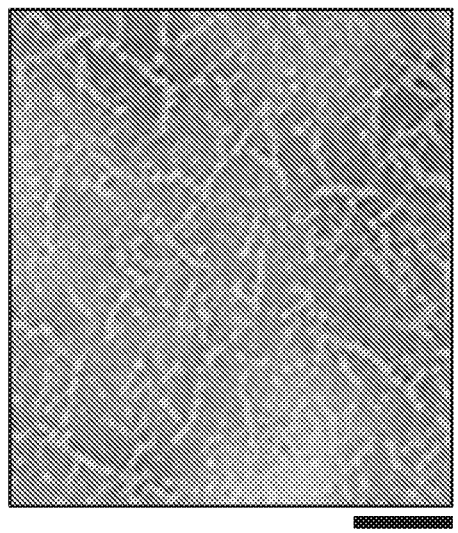
FIGS. 2A-2C are TEM images of several samples.

Transmission electronic microscopy (TEM) was used to examine whether P5P modulates the oligomerization of ASC in vitro. TEM (FIG. 2A) indicates that the co-incubation of MBP-$ASC^{PYD}$ with P5P (100 µM) produces a fibrous network, which consists of fibrils with diameter of 20±2 nm, while the solution of the protein of MBP-$ASC^{PYD}$ (1 mg/mL, ~18 µM), itself, exhibits almost no nanostructures except some serendipitously sparse and relatively large fibrous aggregates after 24 h incubation. This result indicates that P5P, indeed, modulates the oligomerization of MBP-$ASC^{PYD}$.

Example 2—P5P Serves as a Trigger for the Self-Assembly of Short Peptides

Whether P5P could serve as a trigger for the self-assembly of short peptides was next investigated. Peptide 1 was rationally designed based on previous studies that investigated the polymerization mechanism for the assembly of ASC-dependent inflammasomes and the crystal structures of $ASC^{PYD}$ (Lu et al., "Cell 156(6):1193-206 (2014), which is hereby incorporated by reference in its entirety) and for the following reasons: (i) the KKFKLKL (SEQ ID NO: 2) epitope is a conserved surface of residues that play critical roles to interact with negative charged domain for oligomerization of the hASC PYD (Moriya et al., *Biochemistry* 44(2):575-83 (2005), which is hereby incorporated by reference in its entirety); (ii) lysine, the most employed amino acid in proteins, not only serves as an active site for the formation of a Schiff-base (e.g., linkage of P5P and aminotransferase enzyme in a biological system), but also introduces positive charge to the peptides for interacting with the phosphate on P5P (Alexander et al., *Eur. J. Biochem.* 219 (3):953-60 (1994), which is hereby incorporated by reference in its entirety); and (iii) Nap-FF is a well-established building block for promoting self-assembly both in aqueous solution and in biological milieu (Zhang et al., *Langmuir* 27(2):529-37 (2010), which is hereby incorporated by reference in its entirety).

Solid phase peptide synthesis ("SPPS") and purification (by HPLC) were used to obtain the hydrogelator peptide 1 (Fields et al., "Solid Phase Peptide Synthesis Utilizing 9-Fluorenylmethoxycarbonyl Amino Acids," *Int. J. Pept. Protein Res.* 35(3):161-214 (1990), which is hereby incorporated by reference in its entirety). Purification was carried out using a Water Delta600 HPLC system equipped with an XTerra C18 RP column to purify the resulted powder after SPPS. Acetonitrile (from fisher, HPLC grade) plus 0.1% trifluoroacetic acid (TFA) and water (from fisher, HPLC grade) plus 0.1% TFA was used as eluent. The gradient eluted program for purifying peptides was: time=0 min (90% $H_2O$/10% Acetonitrile); 15 min (50% $H_2O$/50% Acetonitrile); 16 min (0% $H_2O$/100% Acetonitrile); 18 min (0% $H_2O$/100% Acetonitrile); 20 min (90% $H_2O$/10% Acetonitrile); and 23 min (90% $H_2O$/10% Acetonitrile).

Figure 2B:
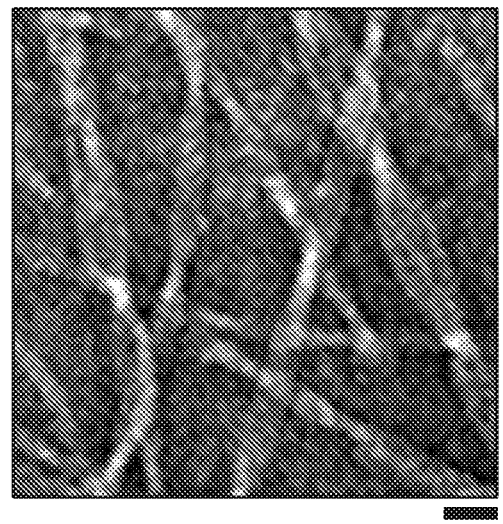

Next, the self-assembly of 1 in aqueous solution was tested by examining its tendency for hydrogelation. Being dissolved in aqueous solution, 1 only forms a transparent viscous solution at the concentration of 0.4 wt % and pH of 7.4. TEM images (FIG. 2B) reveal that the solution of 1 contains uniform nanofibrils with diameter of 7±2 nm, which form twisted nanofibers (Terech et al., *Chem. Rev.* 97:3133-3160 (1997); Estroff et al., *Chem. Rev.* 104:1201-1218 (2004); Ostuni et al., *Angew. Chem., Int. Ed.* 35:1324-1326 (1996); Shen et al. *Angew. Chem., Int. Ed.* 53:13424-13428 (2014), each of which is hereby incorporated by reference in its entirety) with the pitch of about 50±2 nm.

The biocompatibility of peptide 1 with HS-5 (Human Bone Marrow Stromal) cell lines was investigated over 3 days. The results indicate that 1 is cell-compatible at the concentration range of 20-500 µM (Yuan et al., *Angew. Chem., Int. Ed.* 54:5705-5708 (2015), which is hereby incorporated by reference in its entirety). It is expected, therefore, that peptide 1 is also compatible with other types of physiologically normal cells.

Example 3—Hydrogelation of Peptide 1 in the Presence of P5P

Figure 2C:
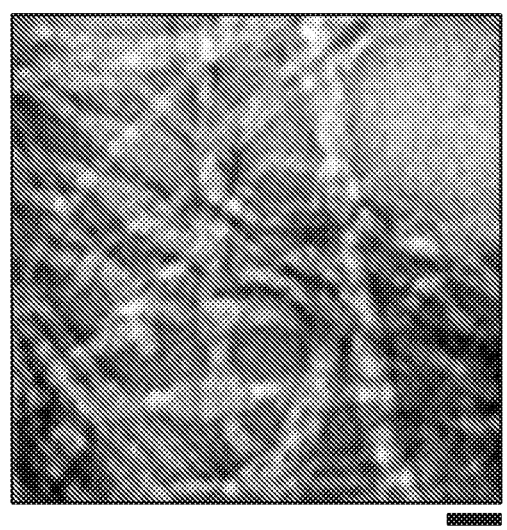
Figure 5:
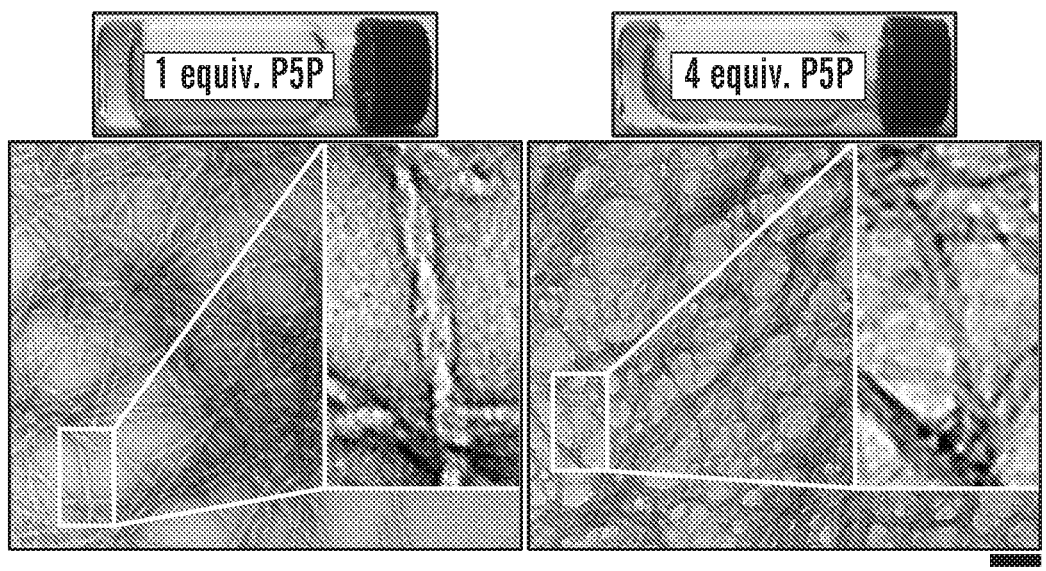
FIG. 5 illustrates optical and TEM images of 1 at the concentration of 0.4 wt % in in the presence of 1 or 4 equivalents P5P in aqueous solution (pH=7.4). Scale bar for the two TEM images is the same: 100 nm.

After the addition of equal molar P5P to the solution of 1, the solution becomes a light yellow hydrogel within 10 seconds by the inverse vial method (Terech et al., *Chem. Rev.* 97:3133-3160 (1997); Estroff et al., *Chem. Rev.* 104: 1201-1218 (2004); Ostuni et al., *Angew. Chem., Int. Ed.* 35:1324-1326 (1996); Shen et al. *Angew. Chem., Int. Ed.* 53:13424-13428 (2014), each of which is hereby incorporated by reference in its entirety) (FIG. 5). TEM images (FIGS. 2C and 5) show that the hydrogel consists of entangled twisted nanofibrils with diameter of 11±2 nm, which is wider than the diameters (7±2 nm) of the nanofibrils formed by 1 itself, suggesting that P5P serves as a cross-linker to enhance the interaction between the fibers formed by 1 (Zhang et al., *Angewandte Chemie* 124:4464-4468 (2012), which is hereby incorporated by reference in its entirety).

Figure 2D:
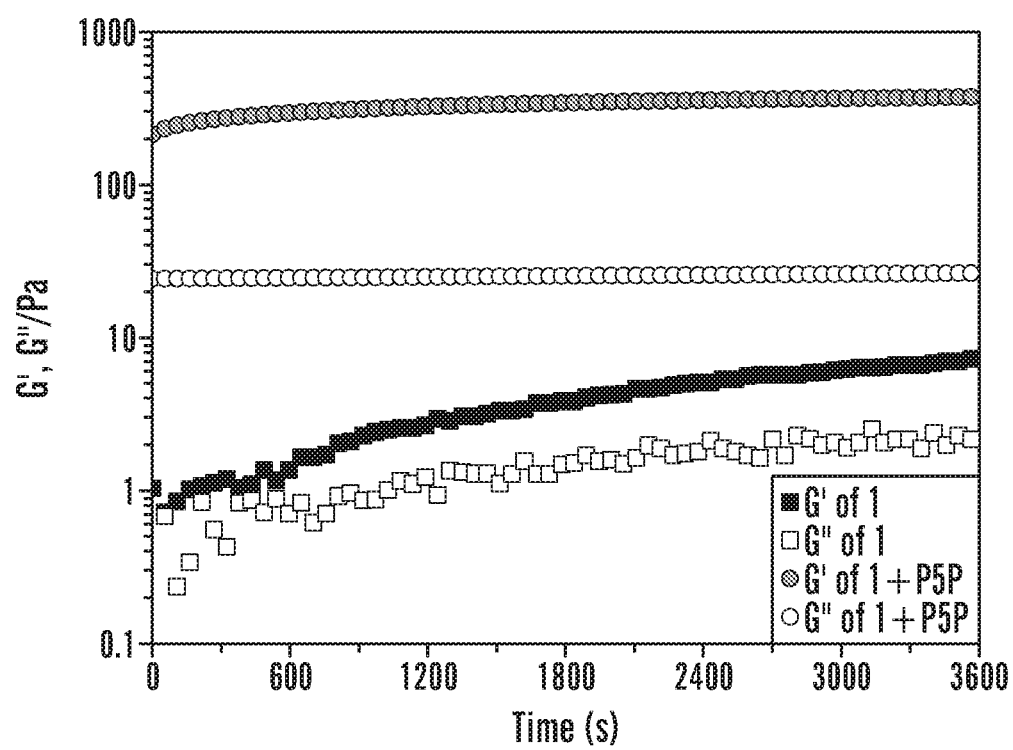
FIG. 2D is a graph illustrating time dependence of the dynamic storage moduli (G') and the loss moduli (G") of 1 without or with the addition of 1 equivalent P5P. All the data are taken in aqueous solution (pH 7.4) of 1 at 0.4 wt %.

A rheometer was used to test the time dependent storage (G') and the loss moduli (G") of 1 in the presence or absence of P5P. As shown in FIG. 2D, the G' of peptide 1 itself is slightly greater than G" (around 6 pa after 1 h incubation), indicating that 1 itself forms viscous solution (not a self-support hydrogel) at the concentration of 0.4 wt %. On the contrast, the G' increases to 40 Pa, which is 8 times higher than the G' of 1 itself, after the addition of one equivalent of P5P. The domination of G' over G" indicates the formation of a stable hydrogel after the addition of P5P. In addition, the immediate increase of G' from 6 Pa to 40 Pa confirms that the gelation occurs almost instantly in the presence of P5P.

Figure 3A:
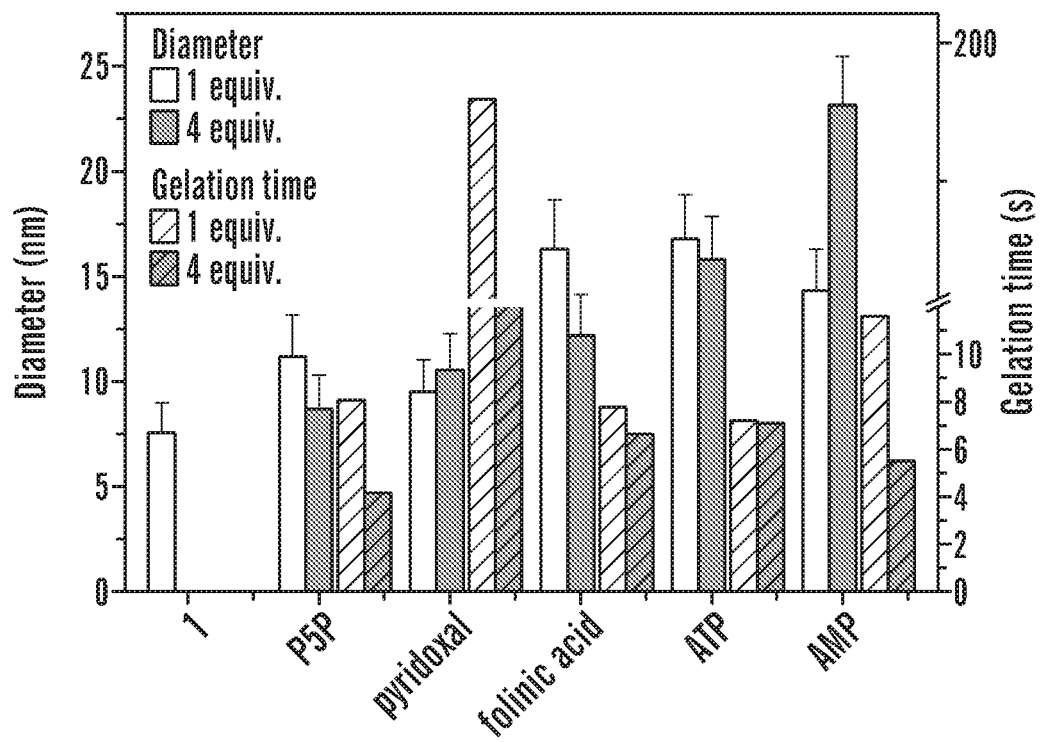
FIGS. 3A-B are graphs illustrating the mean diameter of the nanofibrils or gelation time (FIG. 3A) and rheological characterization of 1 without or with the addition of 1 or 4 equivalents (molar ratio) P5P, pyridoxal, folinic acid, ATP, or AMP (FIG. 3B). For FIG. 3A, the diameter distribution and average diameter of the fibers were measured using ImageJ software from 80 fibers in the TEM images.

Considering that there are four lysine residues on 1, it was next investigated whether the addition of greater than one molar equivalent of P5P to a solution of 1 would increase the speed of hydrogel formation. The addition of two to four molar equivalents of P5P to an aqueous solution of 1 resulted in much faster hydrogelation kinetics, forming a hydrogel within 10 seconds. Notably, four molar equivalents of P5P triggered the hydrogelation of a solution of 1 in 4 seconds (FIG. 3A). Rheology testing indicated a similarly rapid gelation process.

Discussion of Examples 1-3

Two major driving forces contribute to the almost instant hydrogelation (FIG. 1). First, the interactions between positive charges of nanofibers formed by 1 and the negative charges of P5Ps. Second, Schiff-base formation of ε-amino groups of lysines of 1 with aldehyde groups of P5Ps. This observation is consistent with two recently reports: the use of the interaction between lysine and phosphate group to construct asymmetric peptide bilayer membranes (Li et al., *J. Am. Chem. Soc.* 138(10):3579-86 (2016), which is hereby incorporated by reference in its entirety) and Schiff-base formation to fulfill hybrid polymerizations (Yu et al., *Science* 351(6272):497-502 (2016), which is hereby incorporated by reference in its entirety).

The results of Examples 1-3 imply that similar small bioactive molecules with the functional group of aldehyde or phosphate may also trigger hydrogelation of 1. This was further explored in Examples 4-6 below.

Example 4—Hydrogelation of Peptide 1 in the Presence of Pyridoxal

Figure 6:
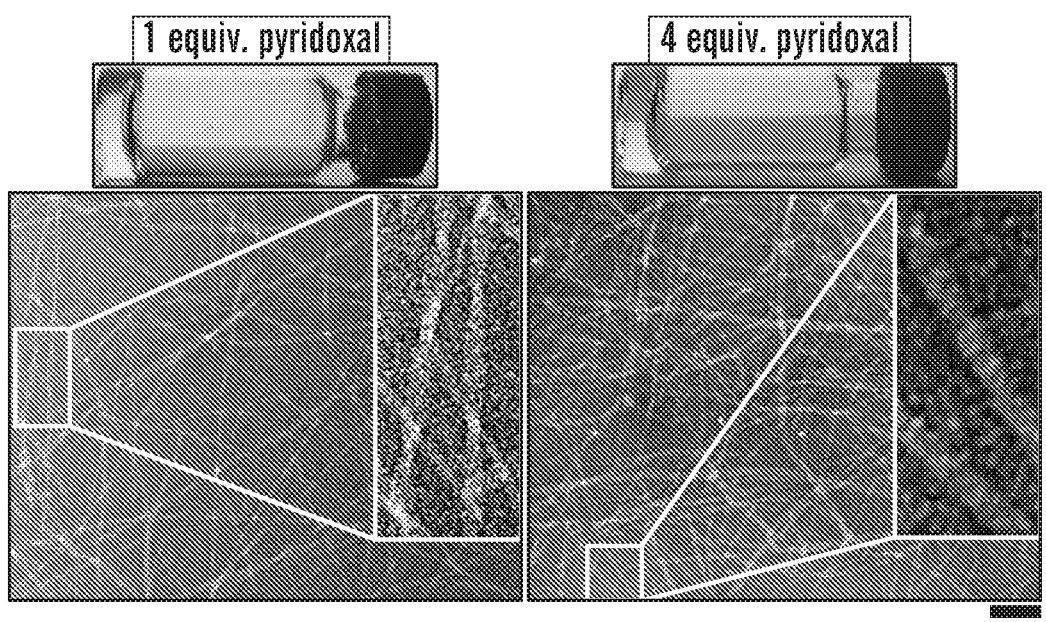
FIG. 6 illustrates optical and TEM images of 1 at the concentration of 0.4 wt % in the presence of 1 or 4 equivalents pyridoxal in aqueous solution (pH=7.4). Scale bar for the two TEM images is the same: 100 nm.

To verify the hypotheses that bioactive molecules having an aldehyde or phosphate active group could trigger the hydrogelation of 1, pyridoxal was evaluated for its ability of to mediate gelation of 1. Pyridoxal is a small molecule precursor for making P5P containing a single aldehyde group. FIG. 3A shows that the phase transition of sol-gel occurs after 190 seconds in the presence of 1 equivalent pyridoxal. Rheology experiments also indicated that the cross point of G' and G" was 77 seconds, while the addition of 4 equivalents pyridoxal resulted in much quicker gelation (within 19 seconds). TEM images revealed that more equivalents of pyridoxal result in higher density of the nanofiber network, while exhibiting similar diameters of nanofibers (one and four equivalents of pyridoxal resulting in nanofibrils of 9±2 and 10±2 nm, respectively, (FIGS. 3A, 4A, and 6). Rheological experiments also suggested that 4 equivalents pyridoxal result in a mechanically stronger hydrogel, the G' of which is 18 times (980 Pa) of that of the hydrogel formed by adding 1 equivalent pyridoxal (G' is 55 Pa, FIG. 3B).

Taken together, these results suggest that Schiff-base formation is not only a key factor for the rapid hydrogelation of 1, but also can tune the mechanical properties of the hydrogels themselves.

Example 5—Hydrogelation of Peptide 1 in the Presence of Folinic Acid

Figure 7:
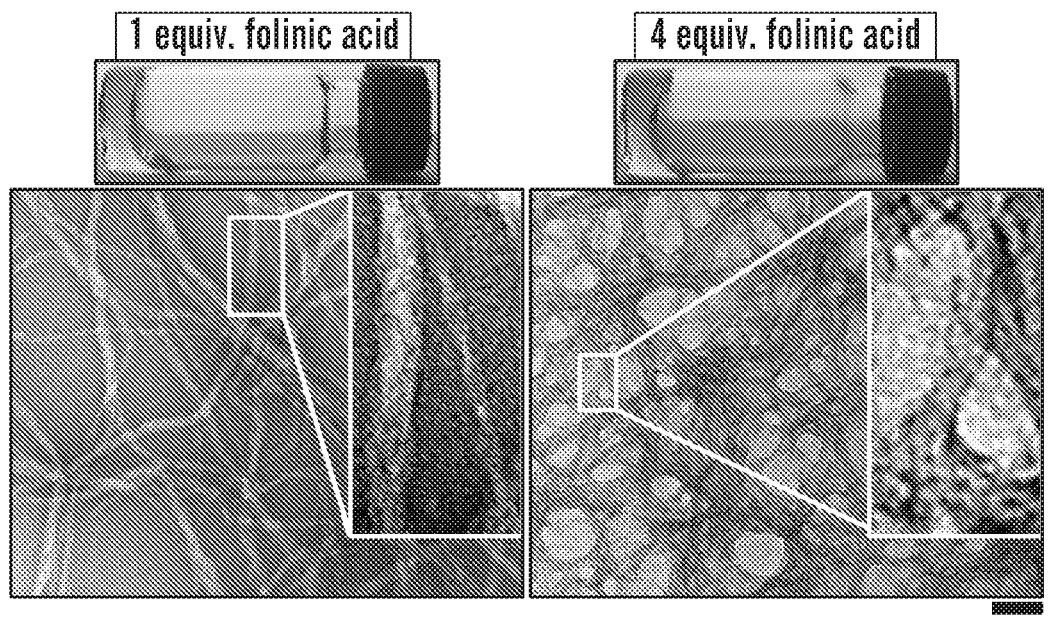
FIG. 7 illustrates optical and TEM images of 1 at the concentration of 0.4 wt % in the presence of 1 or 4 equivalents folinic acid in aqueous solution (pH=7.4). Scale bar for the two TEM images is the same: 100 nm.

To further investigate whether additional bioactive molecules having an aldehyde group could influence the hydrogelation of 1, folinic acid, a vitamer for folic acid with an aldehyde group, was used. Surprisingly, the gelation time of an aqueous solution of 1 in the presence of folinic acid was much faster than that observed following the addition of pyridoxal, which is about 8 (1 equivalent) and 7 seconds (4 equivalents) (FIG. 3A). TEM images indicated that the diameters of nanofibrils formed by addition of 1 or 4 equivalents of folinic acid was 16±2 nm or 12±2 nm, respectively, which was wider than the nanofibrils of 1 alone (FIGS. 3A, 4A, 7). These results also agree with their corresponding storage moduli, 64 and 78 Pa, resulted from 1 and 4 equivalents folinic acid, respectively. The difference between the addition of pyridoxal and folinic acid likely originates from the carboxylate group and intermolecular hydrogen bonding of folinic acid (Ciuchi et al., *J. Am. Chem. Soc.* 116(16):7064-71 (1994), which is hereby incorporated by reference in its entirety), which provide driving forces for fast hydrogelation. LC-MS results confirm that the addition of P5P or pyridoxal in the solution of 1 results in imine bond, while folinic acid fails to form imine bond with 1.

Example 6—Characterization of the Intramolecular Interactions of 1 in the Presence and Absence of Small Bioactive Molecules To further investigate the molecular interactions of 1 in solution and in hydrogel states, ATP and AMP, which only have phosphate groups, were used to assess their electrostatic interactions on hydrogelation (Li et al., *J. Am. Chem. Soc.* 138:3579-3586 (2016); Childers et al., *Angew. Chem., Int. Ed.* 49:4104-4107 (2010); Schoonbeek et al., *Angew.*

Figure 3B:
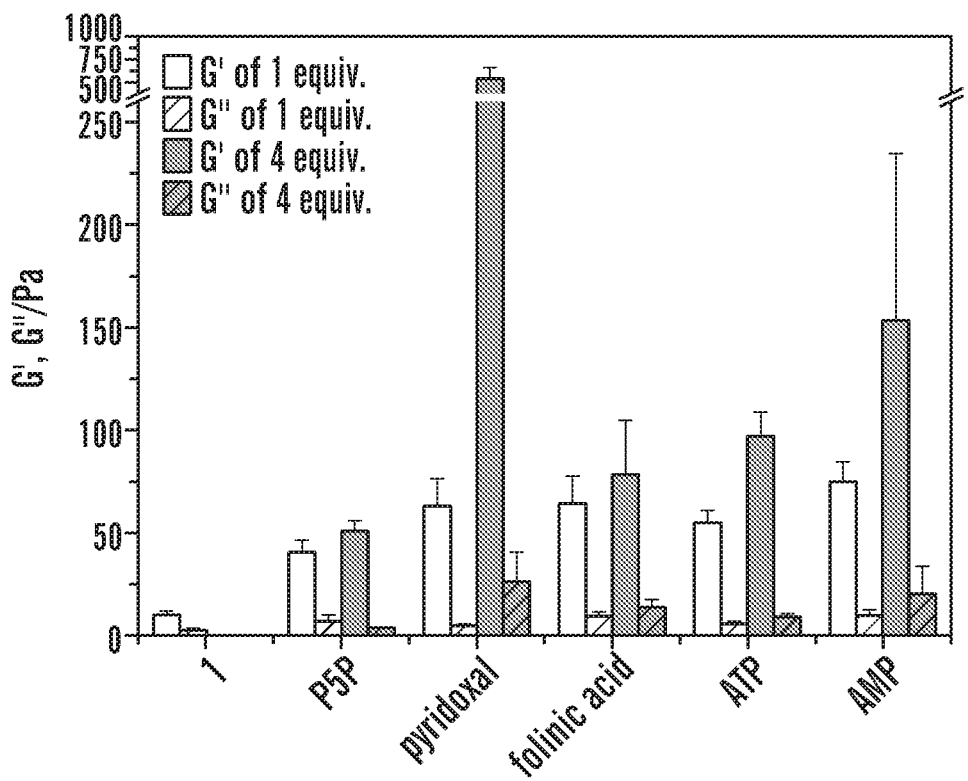
Figure 8:
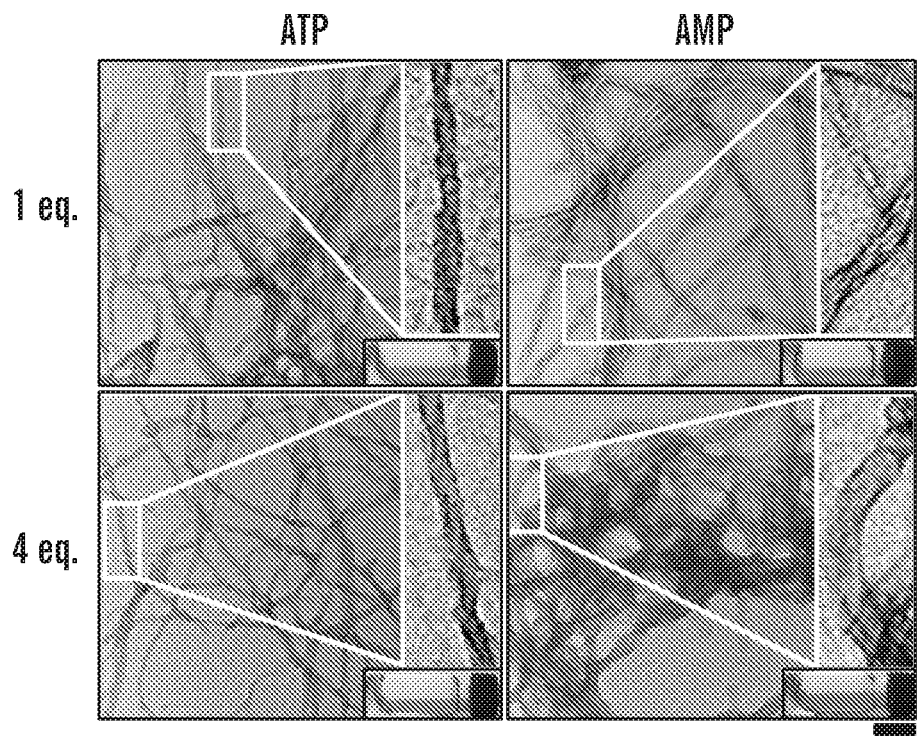
FIG. 8 illustrates optical and TEM images of 1 at the concentration of 0.4 wt % in the presence of 1 or 4 equivalents ATP or AMP in aqueous solution (pH=7.4). Scale bar for the four TEM images is the same: 100 nm.

Chem., Int. Ed. 38:1393-1397 (1999), each of which is hereby incorporated by reference in its entirety). As shown in FIG. 3A, upon addition of 1 or 4 equivalents ATP, the gelation time is same with that of adding P5P, which is about 7 seconds. However, it is a little different in the presence of AMP, forming gels in 11 seconds (1 equivalent AMP) or 5 seconds (4 equivalents AMP). TEM images reveal that ATP or AMP changes the twisted nanofibers formed by 1 to random coils (FIGS. 4A, 8). The diameters of nanofibers are about twice of that of 1 alone. That is, 1 or 4 equivalents ATP (AMP) results in nanofibrils with diameters about 17±2 nm or 16±2 nm (14±2 nm or 23±2 nm), respectively (FIG. 3A, 8). On the other hand, the mechanical properties change little in the presence of ATP or AMP (FIG. 3B). These results indicate that the electrostatic interactions between lysine side chains and phosphate groups are the major factor that contributes to the rapid hydrogelation (Hu et al., *ACS Nano* 10:880-888 (2015), which is hereby incorporated by reference in its entirety).

Figure 4C:
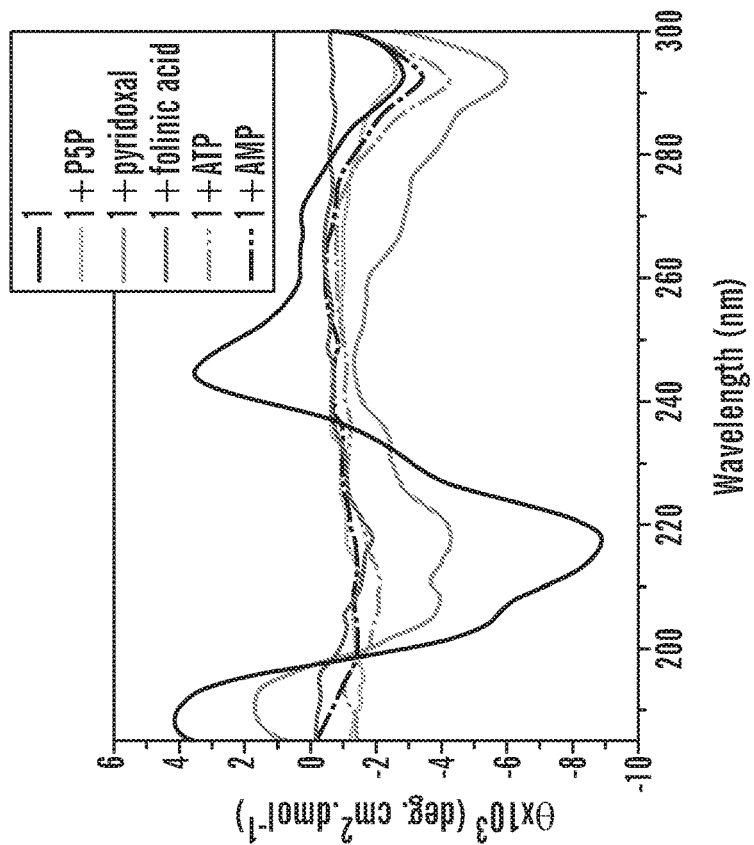
FIGS. 4B-C are graphs illustrating the fluorescent spectrum (λex=272 nm) and CD spectrum, respectively, of 1 without or with the addition of 1 equivalent (molar ratio) P5P, pyridoxal, folinic acid, ATP, or AMP.
Figure 4B:
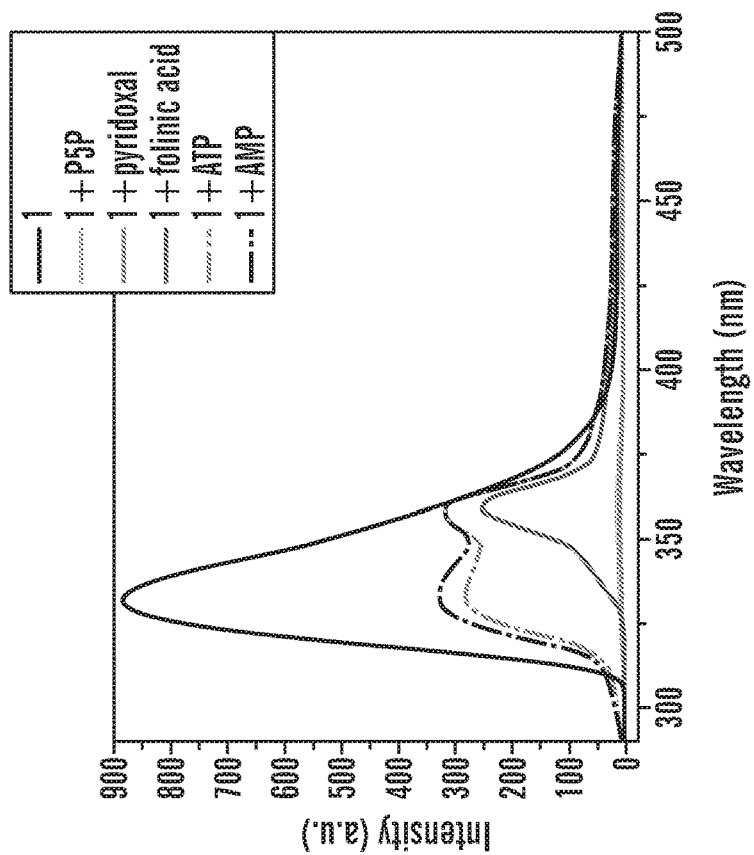

To further investigate the molecular interactions of 1 in solution and in hydrogel states, fluorescence spectroscopy was used to evaluate emission spectra of 1 without or with the addition of the small molecules. The emission spectra of 1 consists of sharp bands at 332 nm in the region of 300 to 400 nm (FIG. 4B). These results agree with the $^1L_b \leftarrow ^1A$ transition (Dutta et al., *Opt. Mater.* 4(5):609-16 (1995), which is hereby incorporated by reference in its entirety). In the presence of P5P or pyridoxal, the emissions decrease to almost no signal, likely due to the efficient energy transfer from the monomeric to the excimeric naphthyl groups, suggesting that aggregation suppresses most fluorescence. These results agree with the observation of hydrogelation and strong interactions between 1 and P5P or pyridoxal. Similar phenomenon were also observed in the presence of folinic acid, ATP, and AMP, their emission spectra also decrease in comparison with the fluorescence intensity of the monomers. The emission spectra also show a strong redshift in 1 of about 27 nm (from 332 nm to 358 nm) in the presence of folinic acid, ATP, and AMP (FIG. 4B). This shift indicates the presence of strong intermolecular interactions of 1 and the formation of aggregates.

Circular dichroism ("CD") was also used to investigate the secondary structure of 1 in the presence or absence of small bioactive molecules. As shown in FIG. 4C, 1 exhibits a predominantly α-helical conformation, bearing two negative bands at 206 nm and 218 nm, as well as a positive band at about 190 nm. In addition, the FT-IR peak around 1652 cm-1 in the amide region confirm the presence of a-helix. This observation agrees with the structure of ASC (Lu et al., *Cell* 156(6):1193-206 (2014), which is hereby incorporated by reference in its entirety). In contrast, the addition of 1 or 4 equivalents of P5P, folinic acid, ATP or AMP results in the decrease of the CD signals, likely due to the negatively charged small molecules interacting with the pre-exist fibers of 1, which reduce the CD signals. This notion is consistent with the observation that the addition of 1 equivalent pyridoxal (a neutral molecule) preserves the CD signal of the α-helical assemblies of 1, agreeing with the calculation of CD signals. These results are consistent with their corresponding TEM images and mechanical property, indicating that 4 equivalents of small molecules generally result in tighter interaction between nanofibers with higher mechanical strength.

Example 7—Use of the Hydrogel as a Drug Release Platform

Next, use of the hydrogel as a controlled drug release platform was explored. The advantage of this system is that the amount of small bioactive molecules is able to tailor the release kinetics of the drug. This was exemplified using doxorubicin (Dox) as an example.

Figure 9A:
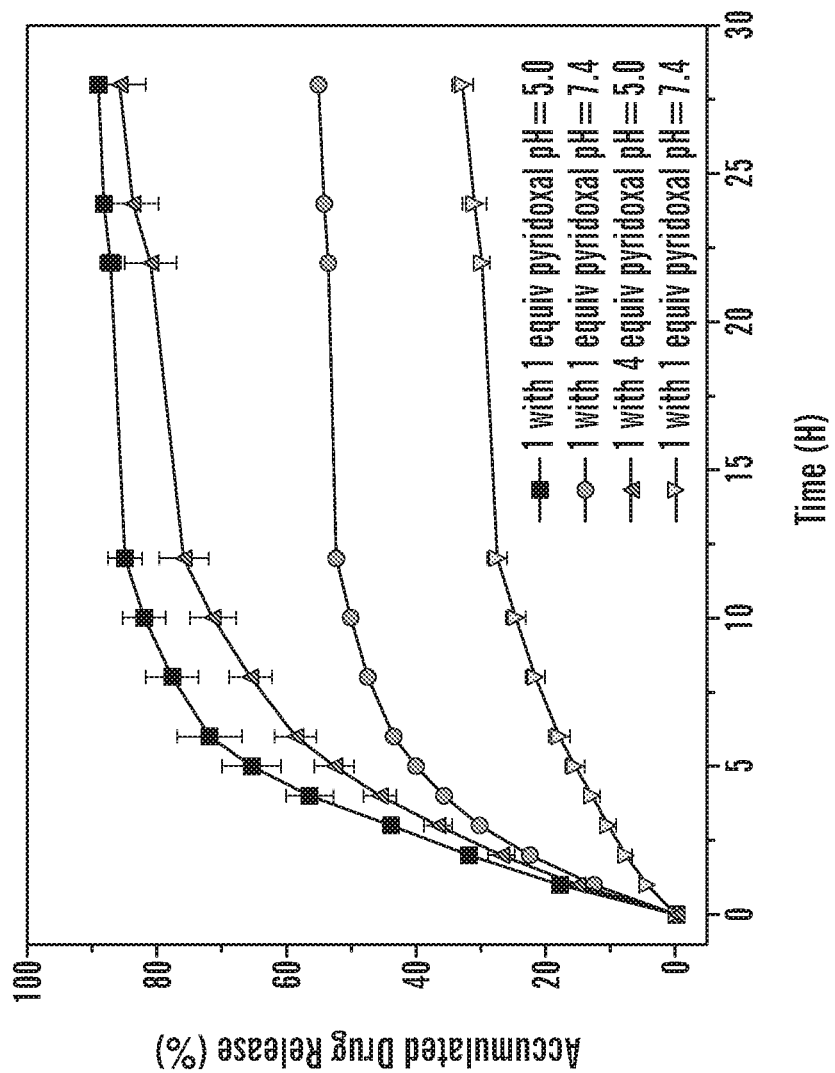
FIGS. 9A-B are graphs showing drug release profiles of the hydrogels formed by 1 using 1 or 4 equivalents (molar) pyridoxal and drug release at pH 5.0 or pH 7.4 (FIG. 9A), or 1 or 4 equivalents ATP and drug release at pH 7.4 (FIG. 9B). The volume of each hydrogel for drug delivery is 250 μL. The experiments were repeated three times for each hydrogel.
Figure 9B:
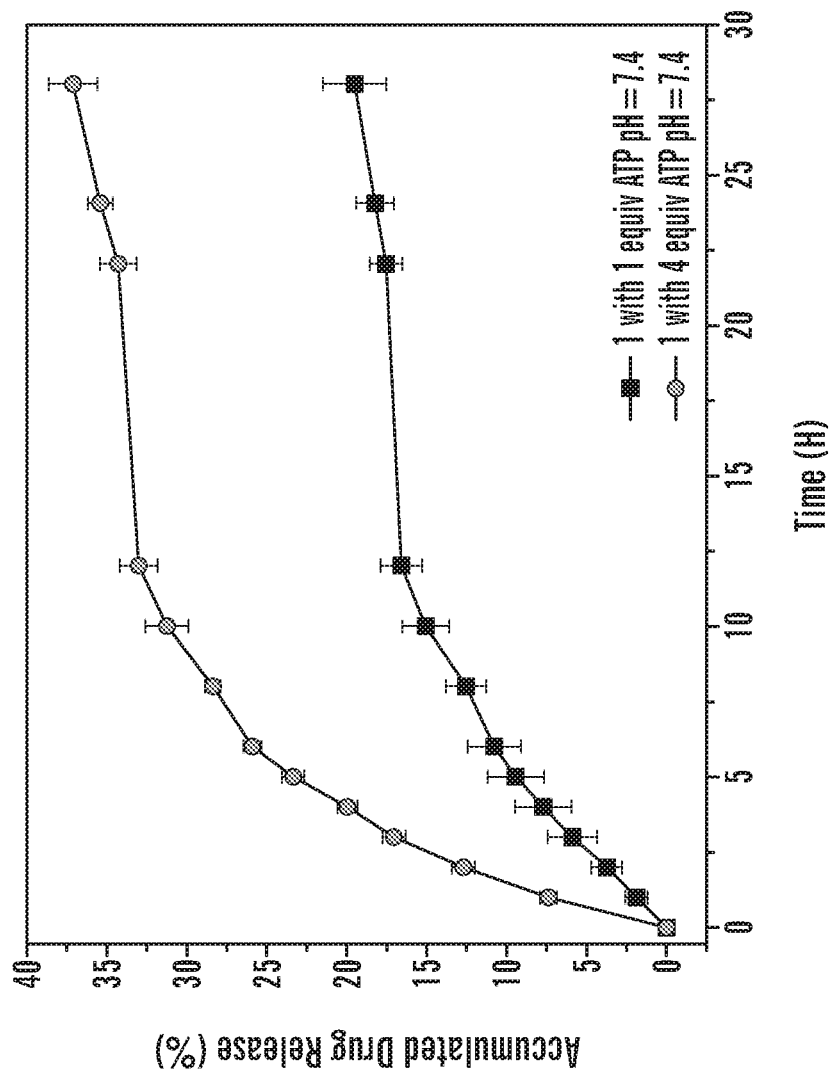

To load the drug, a solution of Dox (1 mg/mL) was added during the gelling process. After the hydrogel formed by addition of pyridoxal or ATP (final concentration of 1 is 0.4 wt % and doxorubicin was 200 μg/mL). 0.25 mL of PBS (0.1 M phosphate-buffered saline (PBS, pH 7.4) or 0.1 M acetate buffer solution (pH 5.0)) was added onto the surface of the hydrogels, 0.2 mL of solution was taken out at the desired time point and 0.2 mL of PBS was added back. For the following time points, 0.2 mL of PBS was taken out and 0.2 mL of PBS was added back at each point. Using this process, the release of Dox was monitored by measuring the absorbance of Dox at wavelength of 480 nm, and its release profile calculated. The experiment was performed at 37° C. in triplicate. The results are shown in FIGS. 9A-B. As expected, the hydrogel releases the Dox according to the type of small bioactive molecules and pH.

Discussion of Examples 1-7

The Examples of the present application demonstrate the design of supramolecular nanostructures (hydrogels) based on peptide epitopes known to be essential for the self-assembly of proteins. A variety of applications can be envisioned using these hydrogels or formed nanostructures. As an example, the potential application of the hydrogel as a controlled drug release platform was explored (FIGS. 9A-B). The results not only indicated that the amount of small molecules is able to tailor the release kinetics of the encapsulated drugs, but also revealed that the hydrogel formed by imine bond is an environment responsive material, which releases about 85% of doxorubicin at pH 5.0 (12 h, 1 equivalent pyridoxal), while only 50% of doxorubicin at pH 7.4. To take advantage of these hydrogels and their good biocompatability, other biomedical applications such as supporting cell culture and wound healing are also expected.

The use of bond formation and ionic interactions simultaneously for triggering hydrogelation also opens up a new venue for rational design peptides for constructing adaptive nanomaterial rather than screening by computational tools (Frederix et al., *Nat. Chem.* 7(1):30-7 (2015), which is hereby incorporated by reference in its entirety). The very recent report of interaction between vitamin B6 and NLRP3 inflammasome at cell level, (Zhang et al., *J. Biol. Chem.* 291(47):24517-27 (2016), which is hereby incorporated by reference in its entirety) in fact, coincides with the design of the peptides of the present invention.

Comparing with other strategies for instant gelation (e.g., the use of $KIO_4$ (Anirudhan et al., *RSC Advances* 4:12109-12118 (2014), which is hereby incorporated by reference in its entirety), changing pH (Petka et al, *Science* 281:389-392 (1998), which is hereby incorporated by reference in its entirety), or enzymatic reactions (Hu et al., *J. Am. Chem. Soc.* 125:14298-14299 (2003); Chen et al., *Biomaterials* 24:2831-2841 (2003), each of which is hereby incorporated by reference in its entirety), the use of small molecules would be more biocompatible and/or much faster. Although, due to the complex cellular milieu, the small molecules may interact with proteins differently in vivo (Chen et al., *J. Am. Chem. Soc.* 130:16496-16497 (2008), which is hereby incorporated by reference in its entirety) than with peptides in vitro, the preceding Examples provide an efficient strategy to design short peptides that adopt conformations (α-helical, random-coil, etc.) other than the most reported β-sheet conformation formed by hydrogelators (Banwell et al., *Nat.*

Mater. 8(7):596-600 (2009); Mondal et al., *ChemNanoMat* 2(5):323-32 (2016); and Du et al., *Chem. Rev.* 115(24): 13165-13307 (2015), each of which is hereby incorporated by reference in its entirety). Most importantly, endogenous small molecules can serve as a cell compatible trigger for crosslinking the pre-exist nanofibers of other peptides (Du et al., *Chem. Rev.* 115(24):13165-13307 (2015), which is hereby incorporated by reference in its entirety) or drugs (Liu et al., *Adv. Mater.* 28(31):6680-6686 (2016), which is hereby incorporated by reference in its entirety), to form instant hydrogel. This instant gelation system also promises many applications (Micklitsch et al., *Angewandte Chemie* 123:1615-1617 (2011); Nagy et al., 1 *Am. Chem. Soc.* 133:14975-14977 (2011); Hirst et al., *Angew. Chem., Int. Ed.* 47:8002-8018 (2008), each of which is hereby incorporated by reference in its entirety), such as wound healing, drug delivery (Lin et al., *ACS Nano* 8:12690-12700 (2014), which is hereby incorporated by reference in its entirety), and ophthalmic disease (Shin et al., *Nat. Mater.* 16(1):147-52 (2016), which is hereby incorporated by reference in its entirety).

Example 8—Design and Characterization of Nucleopeptide NP1

Figure 10A:
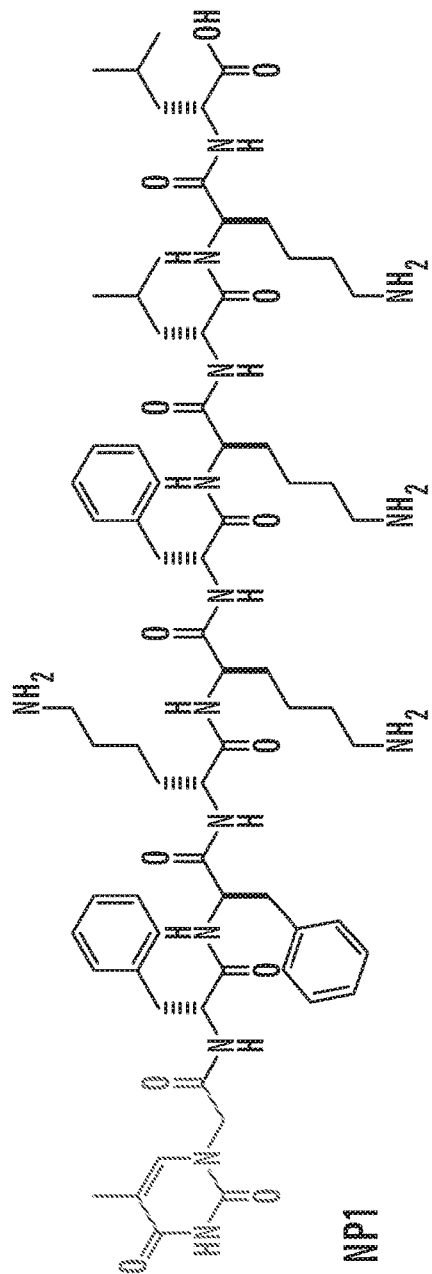
FIGS. 10A-C illustrate nucleopeptide NP1.
Figure 11A:
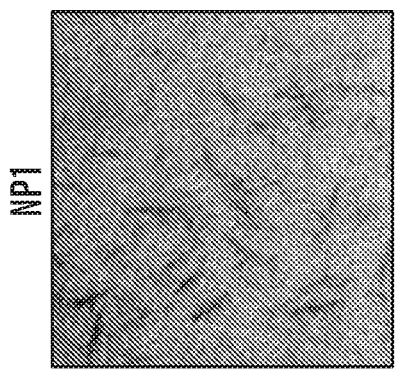
FIGS. 11A-E are TEM images and CD spectra of NP1.
Figure 11B:
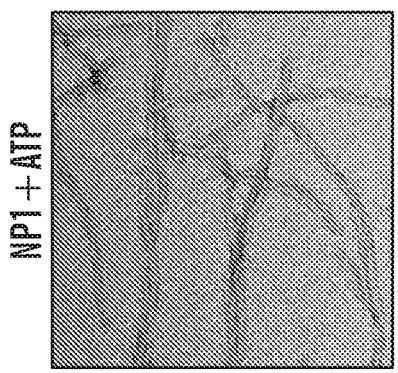
Figure 11C:
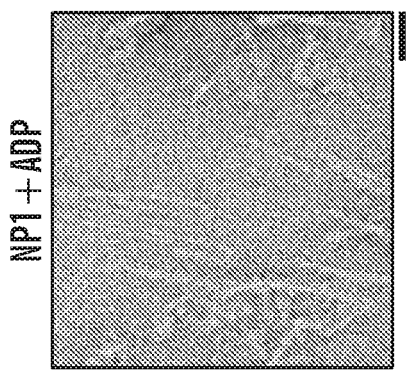

Nucleopeptide NP1 (FIG. 10A) was designed as follows: 1) a D-nonapeptide, ffkkfklkl (f=D-phenylalanine, k=D-lysine, and l=D-leucine), consisting of ff for increasing self-assembly ability, kkfklkl for interacting with the phosphate group of ATP (Wang et al., *Angew. Chem. Int.* 56(26): 7579-7583 (2017), which is hereby incorporated by reference in its entirety), and D-amino acids for proteolytic resistance; 2) thymine, capping the N-terminal of the nonapeptide, which ensures affinity to the adenosine of ATP. After obtaining NP1 by solid-phase peptide synthesis ("SPPS") (Fields et al., *Chem. Biol. Drug Des.* 35:161-214 (1990), which is hereby incorporated by reference in its entirety), the ability of NP1 for differentiating between ATP and ADP was first examined in PBS buffer. NP1 forms a clear solution, which forms a precipitate after the addition of ATP (FIGS. 11A-B). However, NP1 remains as a transparent solution in the presence of ADP (FIG. 11C). As revealed by TEM, NP1 forms short nanofibers with a length of 40±5 nm and width of 4±2 nm, which, in the presence of ATP, turn into uniform nanofibers with several hundred nanometers in length and 7±2 nm in width, which likely further aggregates to form the precipitate (FIGS. 11A-B). ADP interacting with NP1 only results in short nanofibers with diameters of 5±2 nm, which remains soluble (FIG. 11C). Moreover, NP1 differentiates between ATP and ADP in human serum (that is, ATP interacts with NP1 to form precipitates in serum, but NP1 remains soluble in serum upon the addition of ADP, suggesting that the designed nucleopeptides should function under complex physiological conditions.

Figure 10B:
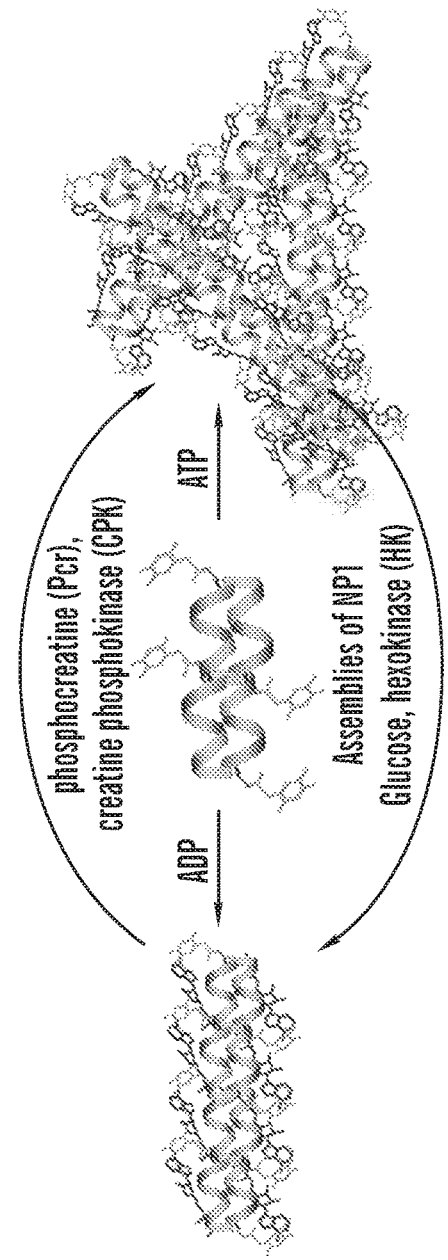
Figure 10C:
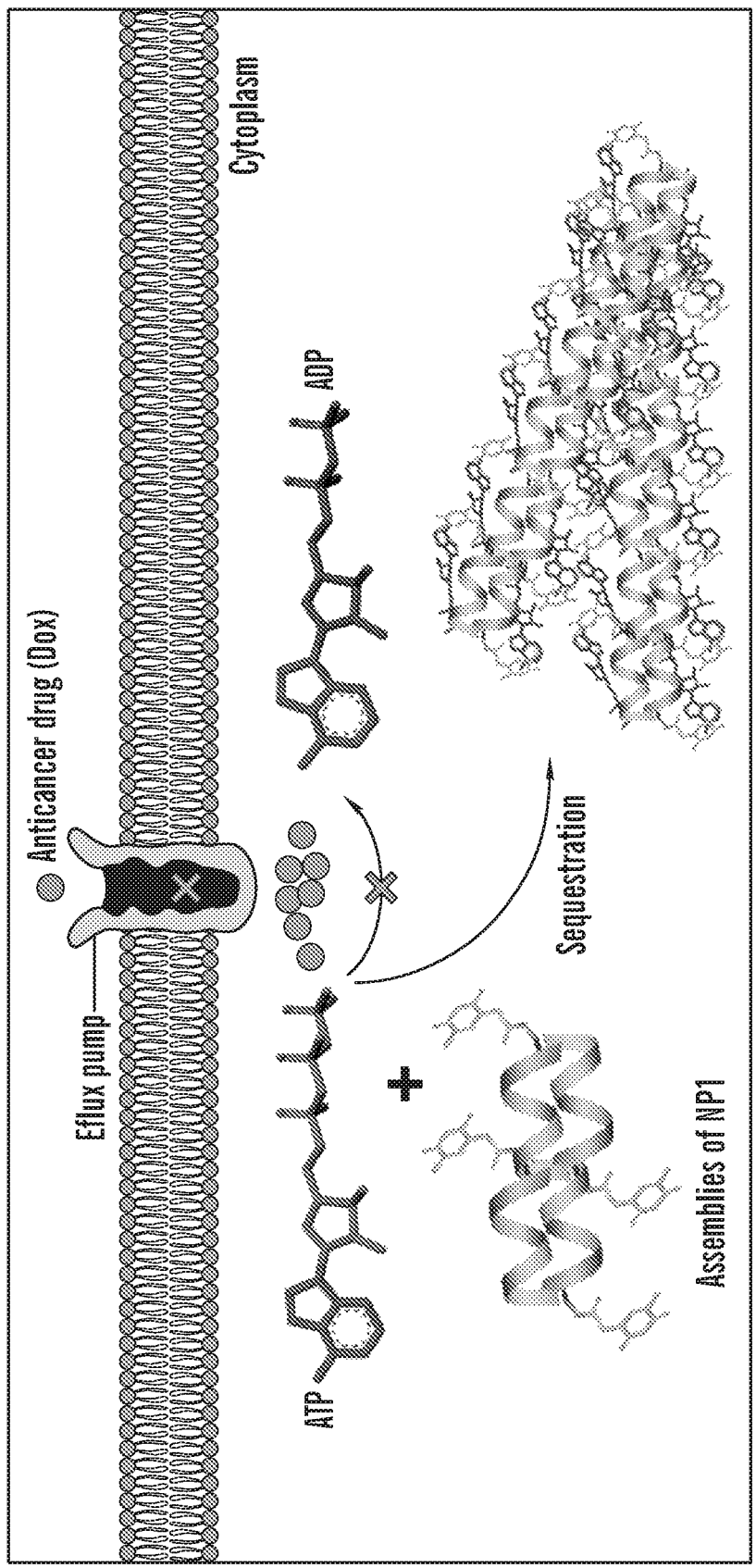
Figure 11D:
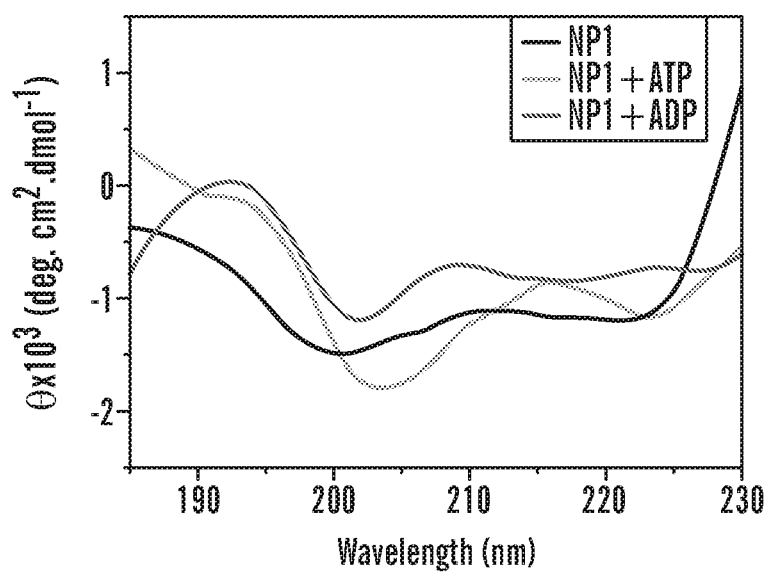
Figure 11E:
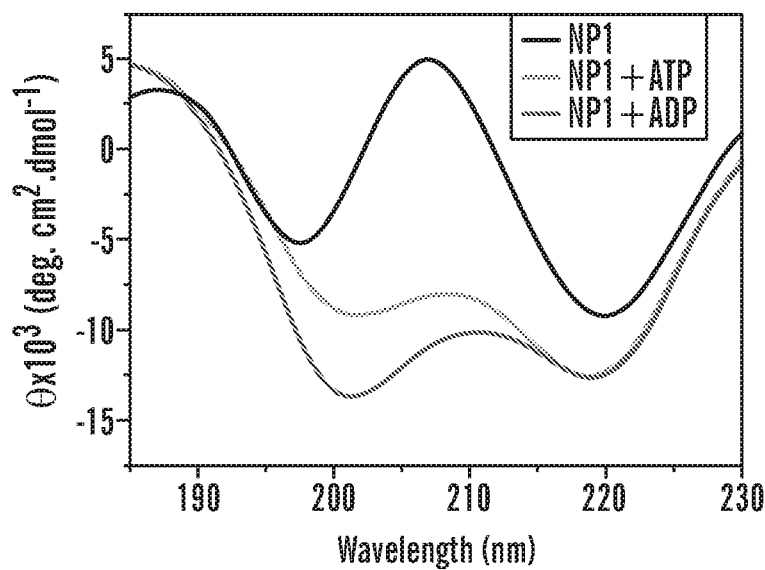

As revealed by the circular dichroism (CD) spectra and their analysis by DichroWeb (Whitmore et al., "*Nucleic Acids Res.* 32:W668-W673 (2004), which is hereby incorporated by reference in its entirety), NP1, at 0.4 wt %, presents predominantly in an α-helical conformation (45%) with 28% of β-sheet and 19% of unordered structures (FIG. 11D). Adding ATP slightly increases the α-helix conformation content of NP1 to 50%, and adding ADP slightly decreases the α-helix of NP1 to 40%. The red shift of two negative peaks of 200 nm and 223 nm in the presence of ATP (or ADP) is in agreement with enhancement of the NP1 assembly by ATP or ADP. Increasing the molar ratio of ATP (or ADP) results in a decrease of CD signal. Increasing the molar equivalents of ATP added causes a greater decrease of the CD signals than ADP, indicating that assemblies of the nucleopeptide interact strongly with ATP. This is also in accordance with the increasing precipitation with increasing added ATP. The slight changes of NP1 conformation after addition of ATP and ADP suggest that stable assemblies of NP1 play a crucial role for sequestering ATP. At 0.05 wt %, NP1 (FIG. 11E) exhibits dominantly unordered structures (55%). The presence of ATP or ADP slightly decreases the proportion of unordered structures but significantly increases the percentage of α-helix from 0% to 9.5% and 15.0%, respectively. While the CD spectra of NP1 and the mixture of NP1 and ADP indicate a slight contribution of linear dichroism, little linear dichroism contributes to the CD spectrum of the mixture of NP1 and ATP. These results agree with the strong interaction of NP1 and ATP. Static light scattering (SLS) of NP1 hardly changes until the concentration of NP1 is above 0.2 wt %, suggesting that NP1 starts to form detectable nanofibers at concentrations higher than 0.2 wt %. These results indicate that the assemblies of NP1 interact more strongly with ATP or ADP than the monomer of NP1, and that ATP or ADP affects the secondary structure of NP1, thus resulting in different assemblies (FIG. 10B-C). Most importantly, these results confirm that NP1 interacts with ATP and ADP differently in PBS buffer.

Example 9—NP1 Sequesters ATP Produced by Cellular Metabolism

To further examine the ability of NP1 to differentiate between ATP and ADP in the presence of other biological molecules (for example, metabolites and enzymes), a pair of counteracting enzymes was employed to interconvert ATP and ADP for controlling the self-assembly of NP1. The enzymes are hexokinase (HK), which phosphorylates hexoses and generates ADP by transferring the phosphate group from ATP to glucose, and creatine phosphokinase (CPK), which catalyzes the generation of ATP from ADP in the presence of phosphocreatine (Pcr). With glucose, NP1 plus ATP forms a precipitate, though TEM reveals more bundles of nanofibers with the fibril diameters of 8±2 nm (FIG. 12A). Adding HK hydrolyzes ATP to ADP, which turns the precipitates into a clear solution and the long nanofibers into short (20-100 nm) and thin (4±2 nm) fibers (FIG. 12B). With Pcr, NP1 plus ADP remains as a clear solution, which contains short nanofibers of 3±2 nm in width (FIG. 12C). The addition of CPK to the solution turns ADP into ATP and forms a precipitate, which consists of long nanofibers with the diameters of 11±2 nm (FIG. 12D). These results indicate that NP1 is able to sequester ATP produced by cellular metabolism.

Figure 13A:
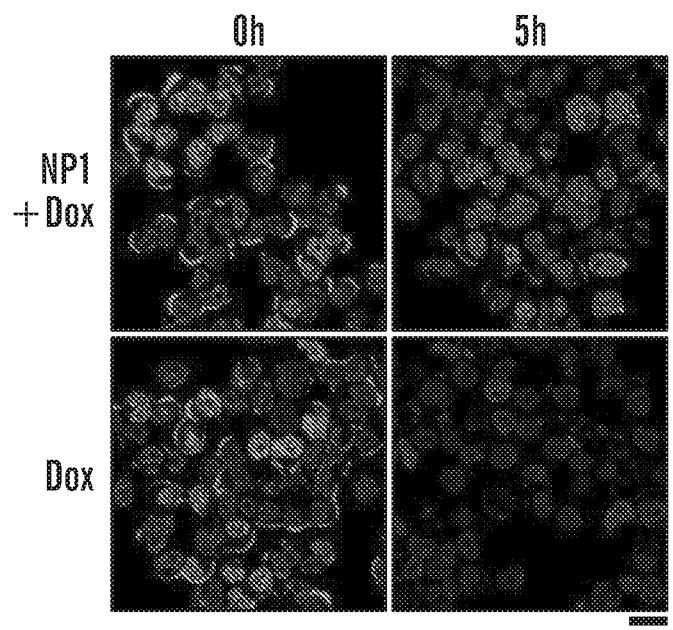
FIGS. 13A-B show the effects of NP1 on Dox treatment in cells.

Example 10—NP1 Exhibits a Dose-Dependent Enhancement of the Anticancer Efficiency of Dox in Vitro Expression of ATP-dependent efflux pumps in cancer cells plays a crucial role in multiple-drug resistance (MDR) (Gottesman et al., *Nat. Rev. Cancer* 2(1):48-58 (2002), which is hereby incorporated by reference in its entirety). Moreover, the concentration of ATP is usually several millimolar in human cells (Gorman et al., *Clin. Chem.* 53(2): 318-25 (2007), which is hereby incorporated by reference in its entirety). $^{31}$P NMR spectra indicated that NP1 can slow down the hydrolysis rate of ATP by ALP. Therefore, the ability of NP1 to sequester ATP in MDR cancer cells was tested. After confirming that NP1 selectively sequesters ATP in a buffer containing major cellular components (for example, various proteins and glycans), MES-SA/dx5 cells (Greer et al., *Biochim. Biophys. Acta.* 1770(9):1275-82 (2007), which is hereby incorporated by reference in its entirety) were treated with NP1 in the presence of Dox. Five hours after changing the medium from one with to one without Dox, most of Dox remains inside the MES-SA/dx5 cells treated with NP1. In contrast, there is little Dox in the MES-SA/dx5 cells without NP1 treatment (FIG. 13A). These results suggest that the assemblies of NP1 likely sequester ATP inside cells, thus preventing the efflux of Dox by the efflux pump driven by ATP. It is possible that the assemblies of NP1 interact with molecules other than ATP to contribute to the retention of Dox inside the cells.

Figure 13B:
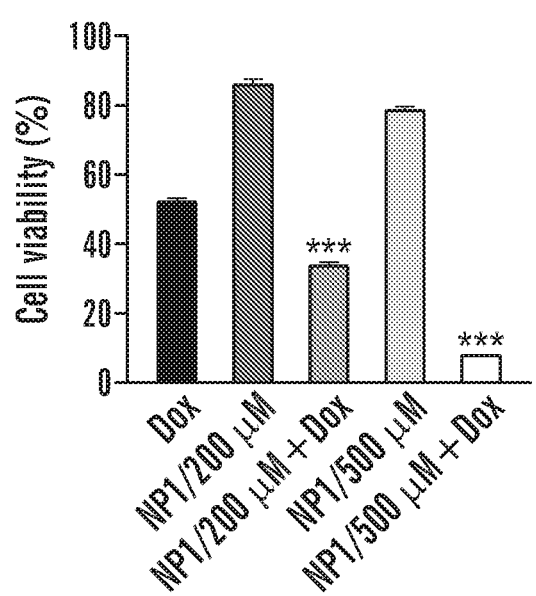

The anti-proliferation efficiency of Dox in combination with NP1 against MES-SA/dx5 cells was further evaluated. Exhibiting little cytotoxicity by itself, NP1 significantly increases the cytotoxicity of Dox against MES-SA/dx5 cells in a dose-dependent manner (FIG. 13B). Specifically, the addition of 500 μm (or 200 μm) NP1 increases cell death caused by Dox from 46% to 92% (or 67%) (FIG. 13B). Moreover, NP1 exhibits a dose-dependent enhancement of the anticancer efficiency of Dox, in agreement with the sequestration of ATP by assemblies of NP1 in vitro.

Figure 14A:
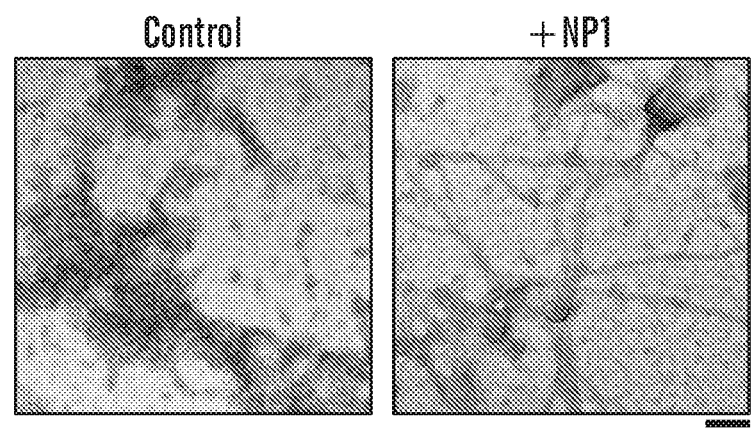
FIGS. 14A-C show the effect of NP1 in live cells.
Figure 14B:
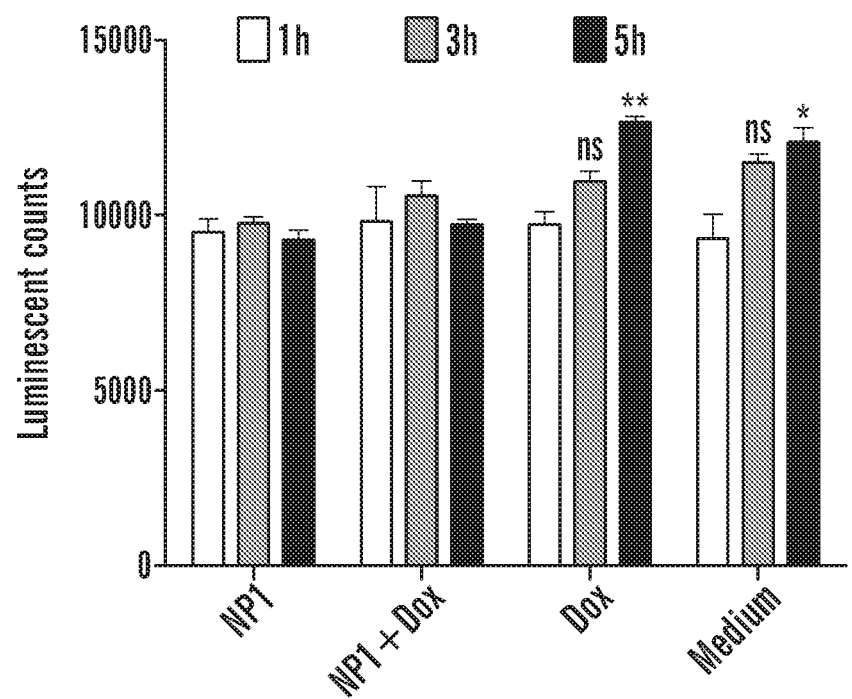
Figure 14C:
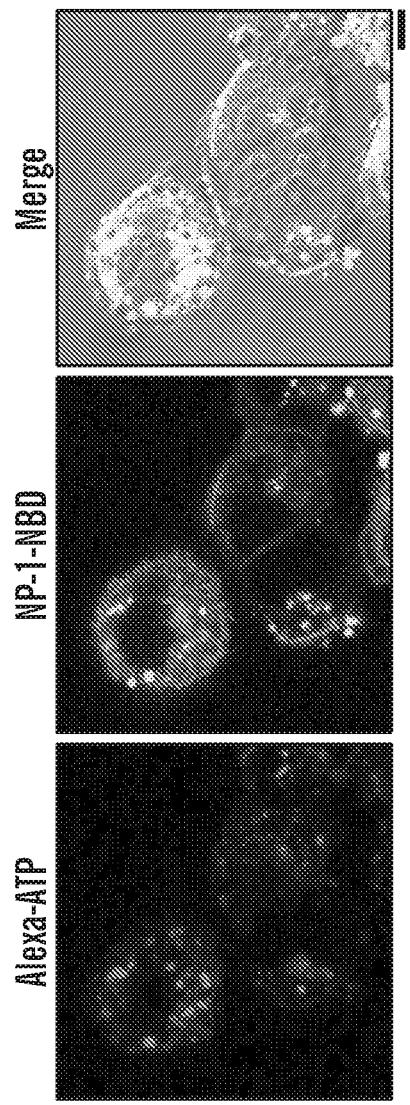
Figure 15:
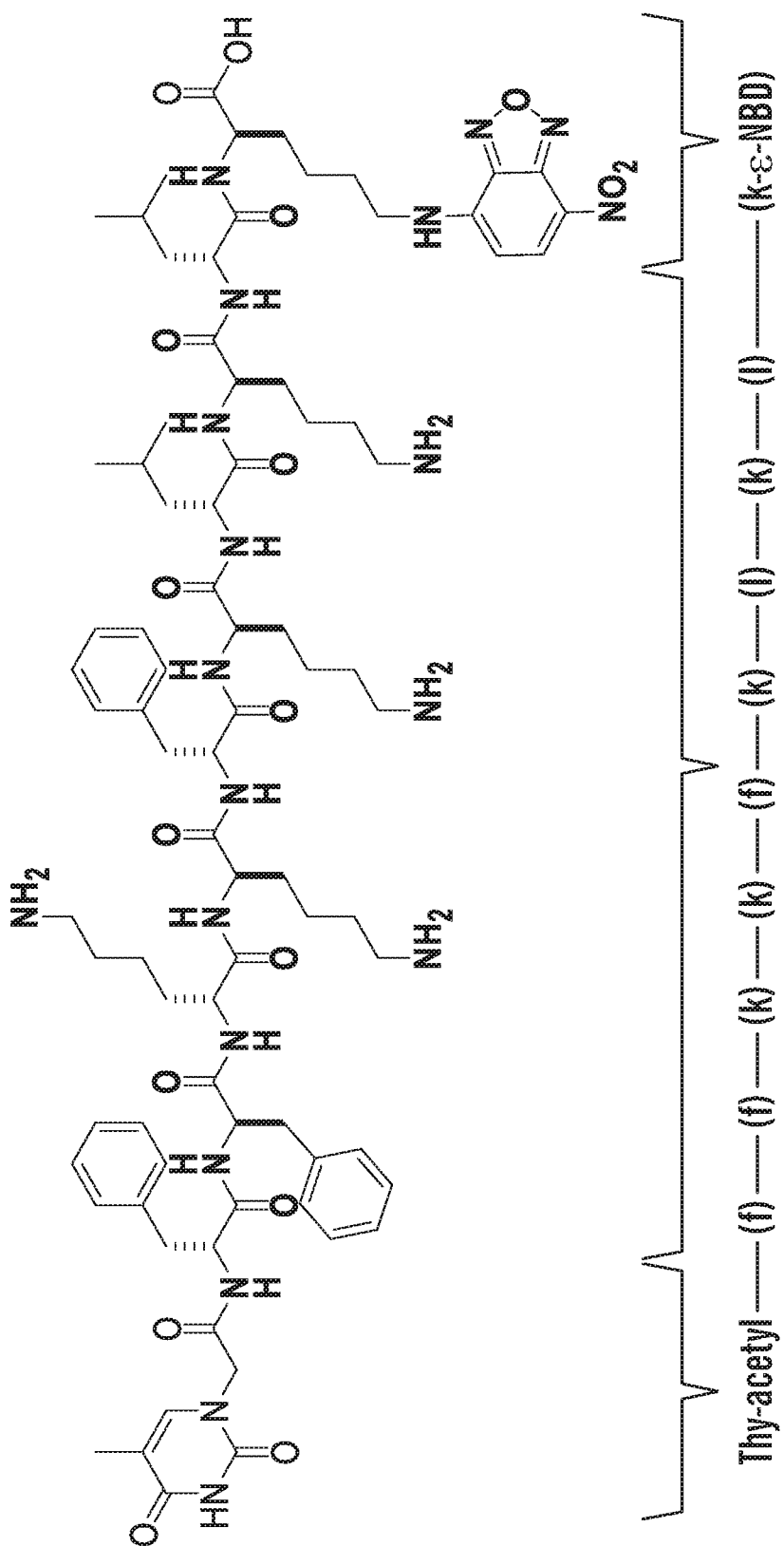
FIG. 15 illustrates the structure of the NP1 variant designated as NP1-NBD. NP1-NBD includes an additional D-Lys residue at its C-terminus, to which the fluorophore NBD is ε-linked.

TEM images of cells incubated without or with NP1 showed that cells incubated with NP1 exhibit nanofibrous structures having diameters of 7±2 nm, which are similar to those of the cell free experiment (FIG. 14A). To test the influence of NP1 on the ATP metabolism in live cells, 10 μm Dox was used to treat MES-SA/dx5 cells to increase the measurable signal without immediately causing cell death. Then, the cellular ATP levels in untreated or Dox-treated conditions in the presence of NP1 were measured. The cells maintain ATP levels after the treatment with NP1 within 5 hours, while the control cells show an increase in ATP levels (FIG. 14B). Because NP1 exhibits little cytotoxicity, this result suggests that NP1 affects the metabolic processes of ATP. To further demonstrate the interaction between NP1 and ATP inside cells, NBD-labelled NP1 (NP1-NBD, FIG. 15) was synthesized as a structural analogue of NP1, which retained the ability to sequester ATP. Confocal laser scanning microscopy (CLSM) images (FIG. 14C) indicate that almost all ATP overlapped with NP1-NBD, and the fluorescence of ATP hardly changes with time. These results further confirm that the designed nucleopeptide selectively sequesters ATP to boost anticancer drug activity in MDR cells.

Example 11—Evaluation of NP1 Analogues

Figure 16:
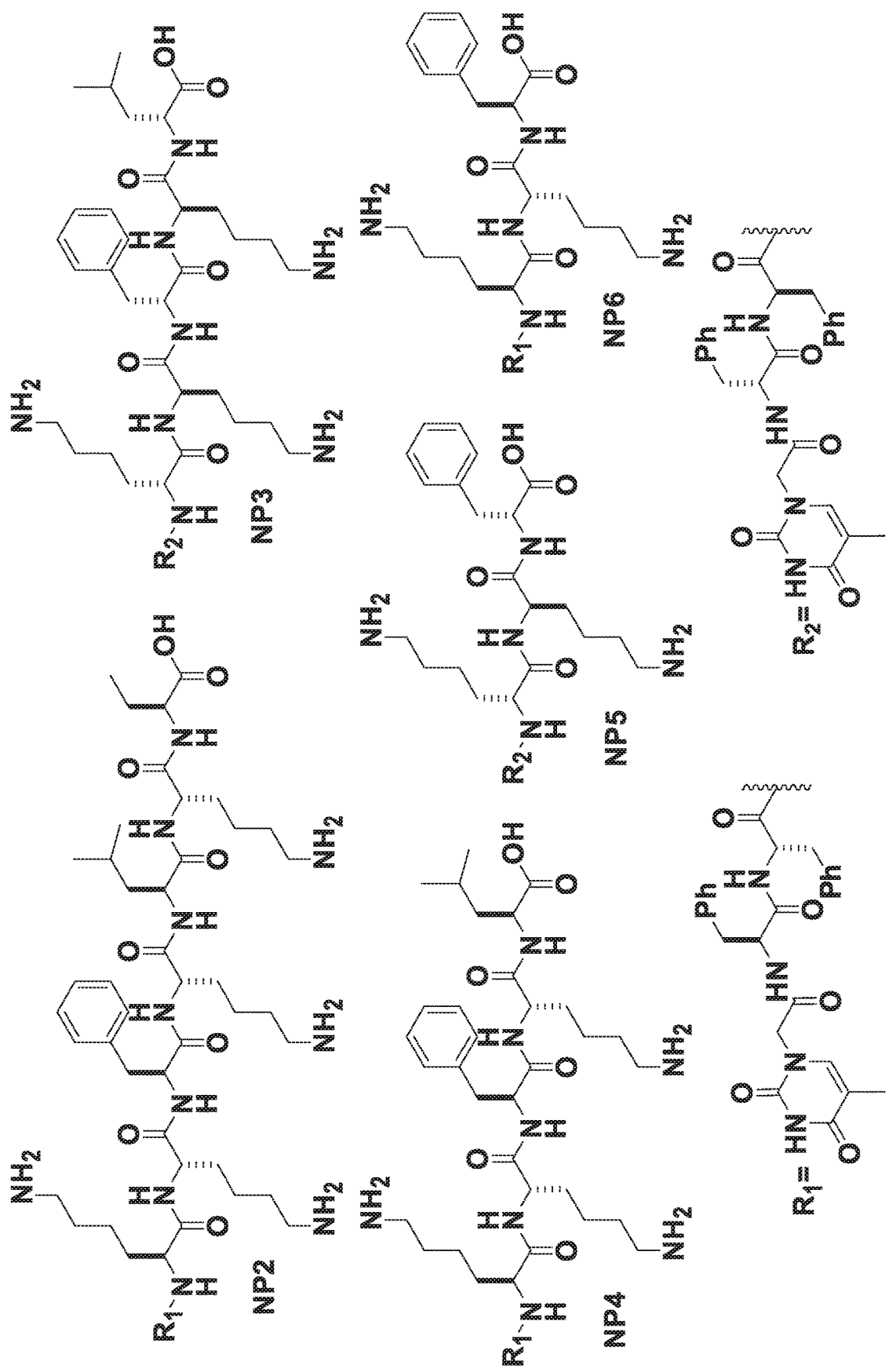
FIG. 16 illustrates molecular structures of NP1 analogs that are able to sequester ATP. $R_1$ represents thyminylacetyl-FF, whereas $R_2$ represents thyminylacetyl-ff. Thus, NP2 is thyminylacetyl-FFKKFKLKL (SEQ ID NO: 74), NP3 is thyminylacetyl-ffkkfkl, NP4 is thyminylacetyl-FFKKFKL (SEQ ID NO:75), NP5 is thyminylacetyl-fllckf, and NP6 is thyminylacetyl-FFKKF (SEQ ID NO: 76). Six other NP1 analogs (not shown) were also prepared and demonstrated to be unable to sequester ATP, including thyminylacetyl-FFKKFKLK (SEQ ID NO: 77, NP7), thyminylacetyl-FFKKFK (SEQ ID NO: 78, NP8), thyminylacetyl-FFKK (SEQ ID NO: 79, NP9), thyminylacetyl-FFK (NP10), thyminylacetyl-FF (NP11), and thyminylacetyl-KKFKLKL (SEQ ID NO: 80, NP12).

To correlate the structures of the nucleopeptides with their ability to sequester ATP, 11 analogues of NP1 were synthesized and their phase transitions in the presence of ATP or ADP were investigated (FIG. 16). NP2, an L-enantiomer of NP1, precipitates after the addition of ATP but remains as a transparent solution in the presence of ADP. TEM reveals that the amorphous nanostructures formed by NP2 transform into spherical structures with a width of 29±2 nm after the addition of ATP, which further interact with each other to form a 3D network and precipitate from the solution. In contrast, ADP interacts with NP2 to form nanofibrous structures with width of 10±2 nm. The different morphologies of the nanostructures that resulted from the solutions of NP1 and NP2 likely originate from their chiralities, which minimally affect their ability to differentiate ATP and ADP, evidenced by the macroscopic phase transition during the ATP/ADP cycle and cellular experiments. Systematically decreasing the lengths of NP1 or NP2 results in four more nucleopeptides (NP3 to NP6, FIG. 16) that differentiate between ATP and ADP through either precipitation or gelation. Further truncation of the NP2 peptide eliminated ATP binding activity. Mutation of D-lysine in NP1 to D-aspartic acid completely removes the ability of the nucleopeptide to sequester ATP or ADP, whereas mutating the D-lysine to D-arginine slightly changes the sequestering ability. These results indicate that the efficacy of the assemblies of nucleopeptides for sequestering ATP depends more on the length than on the chirality and more on self-assembly ability than on the number of charges of the nucleopeptides.

Discussion of Examples 8-11

Adenosine triphosphate (ATP), one of the most important biological anions, plays crucial roles in many cellular processes, including cellular respiration (Warburg, *Science* 123 (3191):309-14 (1956), which is hereby incorporated by reference in its entirety), energy transduction (Lipmann et al., *Adv. Enzymol. Relat. Areas Mol. Biol.* 1:99-162 (1941), which is hereby incorporated by reference in its entirety), enzyme catalysis (DeLange et al., *J. Biol. Chem.* 243:2200-2208 (1968), which is hereby incorporated by reference in its entirety), and signaling (Leist et al., *Exp. Med.* 185(8): 1481-1486 (1997); Bours et. al., *Pharmacol. Ther.* 112(2): 358-404(2006), each of which is hereby incorporated by reference in its entirety). Therefore, selective binding or sequestration of these polyphosphate species under biological conditions would help elucidate their roles in relevant physiological events and provide a powerful way to control cellular processes. Much effort has focused on developing specific receptors, such as synthetic host-guest receptors (Yan et al., *Chem. Sci.* 6:4343-4349 (2015); Yu et al., *Chem. Sci.* 7:4073-4078 (2016); Mo et al., *Nat. Commun.* 5:3364 (2014); Tobey et al., *J. Am. Chem. Soc.* 125(14):4026-4027 (2003); and Busschaert et al., *Chem. Rev.* 115:8038-8155 (2015), each of which is hereby incorporated by reference in its entirety), DNA (Huizenga et al., *Biochemistry* 34(2):656-665 (1995), which is hereby incorporated by reference in its entirety) and RNA-aptamers (Dieckmann et al., *RNA* 2(7): 628-640 (1996); Mo et al., *Angew. Chem. Int. Ed.* 53(23): 5815-5820 (2014); and Sassanfar et al., *Nature* 364:550 (1993), each of which is hereby incorporated by reference in its entirety), bis-Zn-based artificial receptors (Dhiman et al., *Angew. Chem. Int. Ed.* 56(5):1329-1333 (2017) and Ojida et al., *Angew. Chem. Int. Ed.* 45(33):5518-5521 (2006), each of which is hereby incorporated by reference in its entirety), recombinant proteins, and synthetic peptides (Korch et al., *ACS Chem. Biol.* 8(2):451-463 (2013); Ishii et al., *Nature* 423(6940):628-632 (2003); and Butterfield et al., *J. Am. Chem. Soc.* 125(32):9580-9581 (2003), each of which is hereby incorporated by reference in its entirety) for recognizing ATP. Among these strategies, protein engineering or peptide fragment mimetics is a direct approach for ATP recognition or sequestration (Korch et al., *ACS Chem. Biol.* 8(2):451-463 (2013) and Ishii et al., *Nature* 423(6940):628-632 (2003), each of which is hereby incorporated by reference in its entirety). Although some of them exhibit high affinity toward ATP in water (Butterfield et al., *J. Am. Chem. Soc.* 125(32):9580-9581 (2003); Rhee et al., *J. Am. Chem. Soc.* 129(15):4524-4525 (2007); Li et al., *Angew. Chem. Int. Ed.* 44(39):6371-6374 (2005); and Lee et al., *Angew. Chem. Int. Ed.* 43(36):4777-4780 (2004), each of which is hereby incorporated by reference in its entirety) or phosphate-free buffers (for example, HEPES (Dhiman et al., *Angew. Chem. Int. Ed.* 56(5):1329-1333 (2017); Kurishita et al., *J. Am. Chem. Soc.* 132(38):13290-13299 (2010); and Ojida et al.,

*Tetrahedron Lett.* 43(35):6193-6195 (2002), each of which is hereby incorporated by reference in its entirety)), these synthetic molecules are largely ineffective for recognizing ATP in complex physiological conditions (that is, PBS, human serum, and mammalian cells). Therefore, the development of molecules for selectively sequestering ATP in complex media is still limited, and their applications in cells remain unexplored.

The results of Examples 9-12 illustrate the use of assemblies of nucleopeptides for selectively sequestering ATP in complex conditions, and their utility for enhancing drug retention inside cancer cells. These Examples illustrate a novel approach to modulate the function of ATP in cells, confirming that locally increasing the concentration of small molecules (Tiller, *Angew. Chem. Int. Ed.* 42(27):3072-5 (2003) and Bieser et al., *Chem. Commun.* 31:3942-3944 (2005), each of which are hereby incorporated by reference in their entirety) could be a powerful strategy for modulating biological processes. In essence, the use of the interconversion of ATP to ADP to control the dynamics and filaments of NP1 mimics the formation of actin filaments, in which ATP activates G-actin polymerization and hydrolysis of ATP to ADP destabilizes the actin filament (Pollard et al., *Cell* 112(4):453-465 (2003) and Goldschmidt-Clermont et al., *Mol. Biol. Cell* 3(9):1015-1024 (1992), which is hereby incorporated by reference in its entirety). Thus, the reversible morphology transition of the nucleopeptide during the ATP/ADP cycle, which is controlled by counteracting enzymes, may act as a starting point for mimicking the self-assembly/disassembly process of actin. These findings not only provide an alternative strategy for potentially targeting the metabolism of cancer cells with assemblies of small molecules, but also extend the supramolecular assemblies, of which there are many owing to the development of gelators (Mallia et al., *J. Am. Chem. Soc.* 133(38):15045-15054 (2011); Weiss, *J. Am. Chem. Soc.* 136(21):7519-7530 (2014); Sun et al., *J. Am. Chem. Soc.* 135(36):13379-13386 (2013); Tamaru et al., *Angew. Chem. Int. Ed.* 41(5):853-856 (2002); Mukhopadhyay et al., *Chem. Int. Ed.* 49(36):6338-6342 (2010); and Mytnyk et al., *Angew. Chem. Int. Ed.* 56(47):14923-14927 (2017), each of which is hereby incorporated by reference in its entirety), as effective entities for recognizing cellular bioactive molecules.

Figure 17:
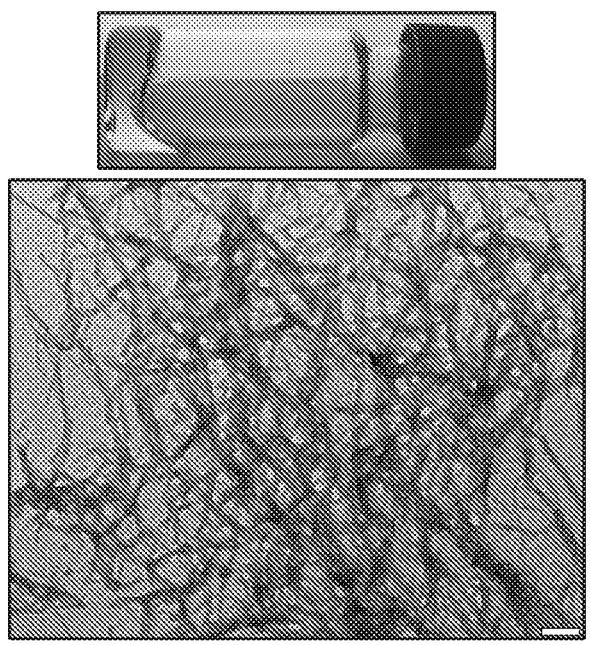
FIG. 17 illustrates optical and TEM images of 1 at the concentration of 0.4 wt % in the presence of 2 molar ratio dexamethasone sodium phosphate. Scale bar is 100 nm.

Example 12—Use of the Hydrogel as a Drug Release Platform and Treatment of Experimental Autoimmune Uveitis To load dexamethasone sodium phosphate, 2 molar excess of dexamethasone sodium phosphate was added to a solution containing 0.4 wt % of Peptide 1 (see Example 2 above). Optical and TEM images of the resulting hydrogel are shown in FIG. 17.

Experimental autoimmune uveitis (EAU) is an animal disease model of human endogenous uveitis and can be induced in susceptible animals by immunization with retinal antigens. EAU resembles the key immunological characteristics of uveitis in humans as both are T-cell mediated diseases (Th1) targeting the neural retina and related tissues. EAU is induced by immunization with preparation of purified retinal Ags or their fragments, such as retinal soluble antigen, arrestin; inter-photoreceptor retinoid-binding protein ("IRBP"); rhodopsin and its illuminated form-opsin; recoverin; and phosducin.

Lewis rats were immunized by subcutaneous injection of 100 µL of IRBP peptide emulsified with complete Freund's adjuvant containing *Mycobacterium Tuberculosis* H37Ra (Difco Laboratories, Detroit, Mich.). The rats were monitored daily by a slit-lamp for clinical signs of EAU, and the severity was graded from 0 to 4 according to the previous study. Grade 0: no inflammation; grade 1: mild iris vessel engorgement and minimal retinal vasculitis; grade 2: mild retinal vasculitis and anterior chamber cells; grade 3: fibrous exudates at the pupil margin and moderate retinal vasculitis; and grade 4: severe retinal vasculitis and retroiridal hypopyon. After 10 days post injection, the rats were separately treated with different groups via retrobulbar injection were treated with either PBS comprising dexamethasone (15 µg), dexamethasone-loaded hydrogel 1 (15 µg dexamethasone), or PBS (control).

Dexamethasone loaded hydrogel was prepared as follows: Peptide 1 (5.0 mg) dissolved in 1 mL of aqueous buffer (sodium hydroxide was used to adjust the final pH to 7.4), the hydrogels formed after the addition of different equivalent of small molecule (initial concentration is 100 mM) of dexamethasone sodium phosphate. The final concentration of peptide was 0.4 wt %.

Figure 18:
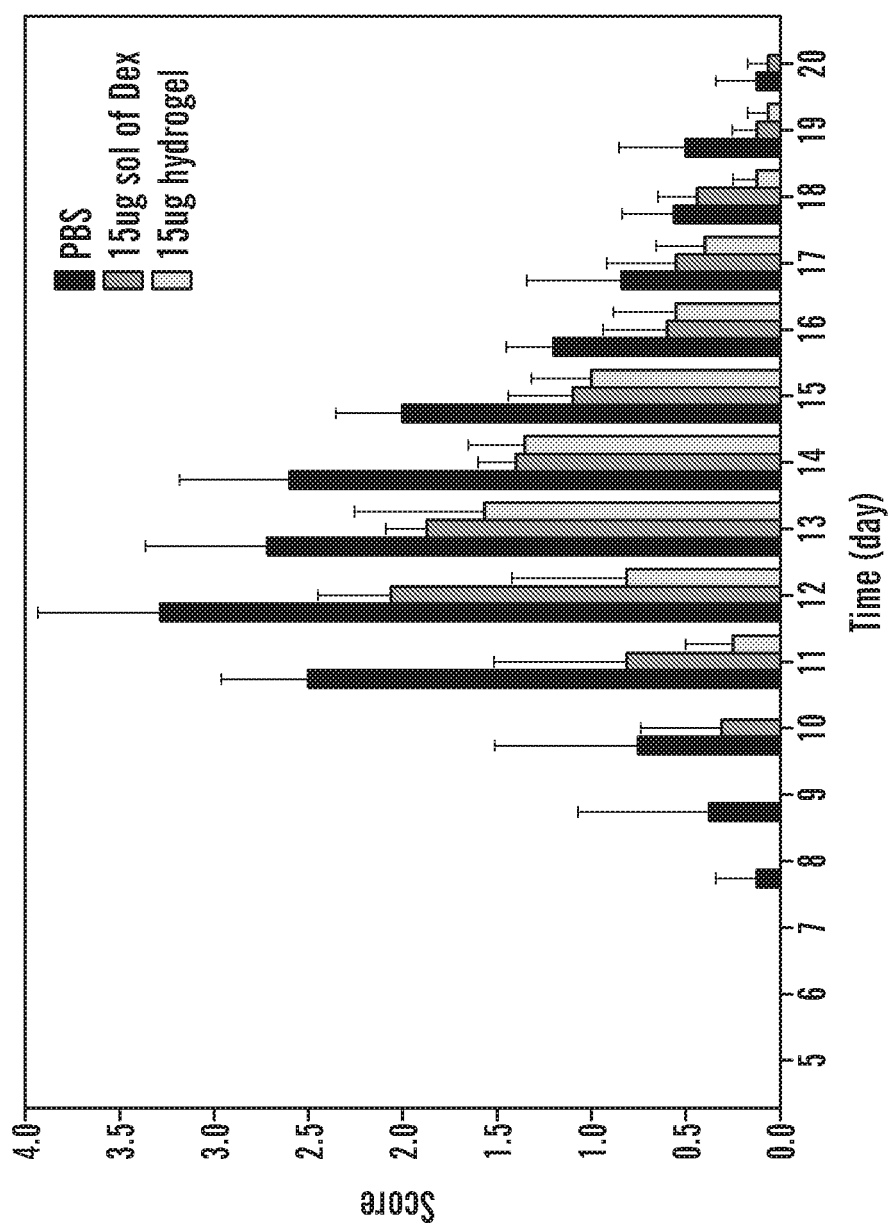
FIG. 18 is a graph depicting the clinical score of rats with EAU (data expressed as mean±SD).
Figure 19:
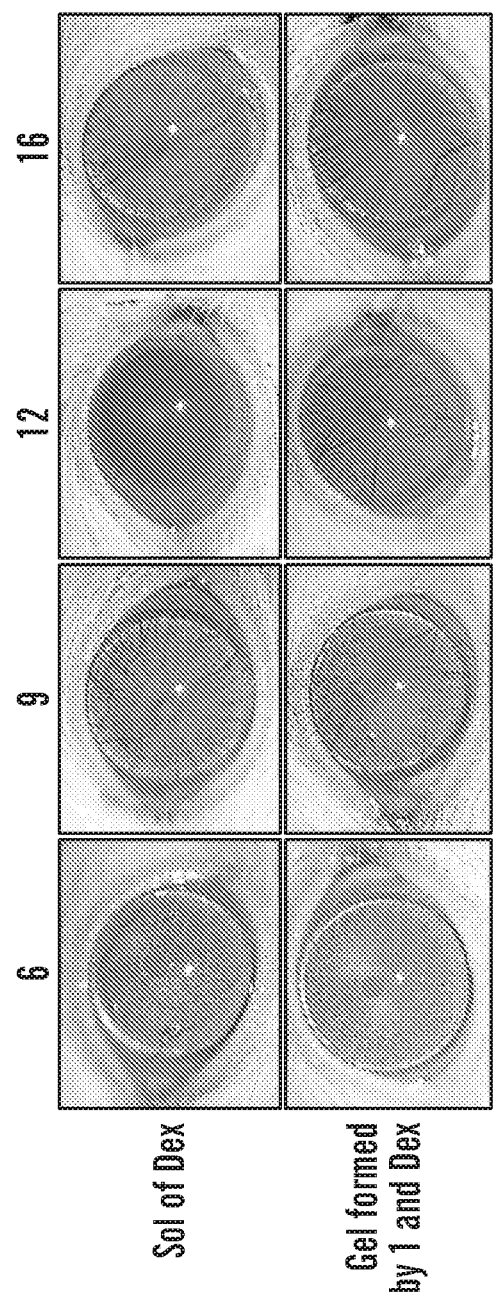
FIG. 19 is a panel of images illustrating the severity of experiment autoimmune uveitis (EAU) at days 6, 9, 12 and 16 treated with 15 μg of dexamethasone sodium phosphate or hydrogel 1 loaded with dexamethasone sodium phosphate (15 μg).

The results are shown in FIGS. 18-19. While dexamethasone reduced the severity and duration of EAU symptoms relative to PBS alone, dexamethasone-loaded hydrogel 1 further reduced the severity and duration of EAU. A large amount of pus exudate for the control rats that were administrated the solution of dexamethasone sodium phosphate was observed at the day 12 and 16 time point, while fewer amounts of pus exudates were observed for rats administrated with hydrogel group. These observations suggest that hydrogel 1 has potential for improved treatment of eye diseases. One explanation for the improved result is that the hydrogel releases the drug over a prolonged period of time.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

SEQUENCE LISTING

The Sequence Listing is being submitted electronically in txt format and is hereby incorporated by reference in its entirety. Said txt copy, created on Sep. 26, 2022, is named 147376_000372.ST25.txt and is 31,589 bytes in size. No new matter is being introduced.

What is claimed is:

1. A peptide capable of induced self-assembly by a bioactive molecule, the peptide comprising (i) a hydrogelation-promoting amino acid sequence comprising an aryl or heteroaryl capping moiety and a plurality of aromatic amino acids, and (ii) an oligomerization sequence comprising the amino acid sequence of (Z/E/R)-(Z/T/R)-(F/L)-(Z/Q/R)-X-(Z/H/Y)-L (SEQ ID NO: 99), where X is any amino acid and Z is either K or a lysine residue whose sidechain is conjugated to a therapeutic agent;

wherein the hydrogelation-promoting amino acid sequence is fused to an N-terminal end of the oligomerization sequence.

2. The peptide according to claim 1, wherein the aromatic amino acids are selected from the group consisting of phenylalanine, phenylalanine derivatives, naphthylalanine, naphthylalanine derivative, tyrosine, tyrosine derivatives, tryptophan, and tryptophan derivatives.

3. The peptide according to claim 1, wherein the hydrogelation-promoting amino acid sequence comprises naphthylacetyl-F-F, naphthylacetyl-F-F-K, naphthylacetyl-f-f, naphthylacetyl-f-f-k, naphthylacetyl-F-F-K-F, naphthylacetyl-f-f-k-f, thyminylacetyl-F-F, thyminylacetyl-F-F-K, thyminylacetyl-f-f, thyminylacetyl-f-f-k, thyminylacetyl-F-F-K-F, thyminylacetyl-f-f-k-f, uracilylacetyl-F-F, uracilylacetyl-F-F-K, uracilylacetyl-f-f, uracilylacetyl-f-f-k, uracilylacetyl-F-F-K-F, uracilylacetyl-f-f-k-f, cytosinylacetyl-F-F, cytosinylacetyl-F-F-K, cytosinylacetyl-f-f, cytosinylacetyl-f-f-k, cytosinylacetyl-F-F-K-F, cytosinylacetyl-f-f-k-f, adeninylacetyl-F-F, adeninylacetyl-F-F-K, adeninylacetyl-f-f, adeninylacetyl-f-f-k, adeninylacetyl-F-F-K-F, adeninylacetyl-f-f-k-f, guaninylacetyl-F-F, guaninylacetyl-F-F-K, guaninylacetyl-f-f, guaninylacetyl-f-f-k, guaninylacetyl-F-F-K-F, or guaninylacetyl-f-f-k-f.

4. The peptide according to claim 1, wherein the oligomerization sequence comprises:

(L/F)-(K/E/R)-(K/T/R)-(F/L)-(K/Q/R)-X-(K/H/Y)-L or (K/E/R)-(K/T/R)-(F/L)-(K/Q/R)-X-(K/H/Y)-L, where X is any amino acid.

5. The peptide according to claim 1, wherein oligomerization sequence is selected from the group consisting of:

(human ASC, chain A)  
KKFKLKL (SEQ ID NO: 2)

(human ASC, chain A)  
LKKFKLKL (SEQ ID NO: 3)

(human ASC, chain Q)  
KKFKMKL (SEQ ID NO: 4)

(human ASC, chain Q)  
LKKFKMKL (SEQ ID NO: 5)

(zebrafish, ASC-like protein)  
RKFKSKL (SEQ ID NO: 6)

(zebrafish, ASC-like protein)  
LRKFKSKL (SEQ ID NO: 7)

(Xenopus, ASC-like protein)  
KKFKGKL (SEQ ID NO: 8)

(Xenopus, ASC-like protein)  
FKKFKGKL (SEQ ID NO: 9)

(Human Pyrin iso1)  
EKFKFKL (SEQ ID NO: 10)

(Human Pyrin iso1)  
FEKFKFKL (SEQ ID NO: 11)

(human Nalp10)  
KKLKFYL (SEQ ID NO: 12)

(human Nalp10)  
FKKLKFYL (SEQ ID NO: 13)

```
                    (mouse Nalp10)
                                    (SEQ ID NO: 14)
    KTLKFHL (mouse Nalp10)
                                    (SEQ ID NO: 15)
    FKTLKFHL (human Nlrp6)
                                    (SEQ ID NO: 16)
    KRFRHKL (human Nlrp6)
                                    (SEQ ID NO: 17)
    LKRFRHKL (zebrafish Nlrc3-like protein)
                                    (SEQ ID NO: 18)
    KKFQWHL (zebrafish Nlrc3-like protein)
                                    (SEQ ID NO: 19)
    LKKFQWHL.
```

6. The peptide according to claim 1, wherein the aryl or heteroaryl capping moiety is selected from the group comprising a fluorophore, a chemotherapeutic agent, an antiangiogenic agent, an immunomodulating agent, or an antigen.

7. The peptide according to claim 1, wherein the aryl or heteroaryl capping moiety is an arylacyl selected from 2-naphthylacetyl, phenylacetyl, fluorenyl-9-methoxycarbonyl, pyrenylbutanoyl, cinnamoyl, 3-((7-nitrobenzo(c)-1,2,5-oxadiazol-4-yl)amino)proprionyl, or an acylated nucleobase, wherein the nucleobase is selected from thyminyl, uracilyl, cytosinyl, adeninyl, and guaninyl.

8. The peptide according to claim 1, wherein said peptide is between 9 to 15 amino acids.

9. The peptide according to claim 1, wherein the peptide is selected from the group consisting of:

```
                                    (SEQ ID NO: 1)
    naphthylacetyl-FFKKFKLKL, (SEQ ID NO: 21)
    naphthylacetyl-FFLKKFKLKL, (SEQ ID NO: 22)
    naphthylacetyl-FFKKFKMKL, (SEQ ID NO: 23)
    naphthylacetyl-FFLKKFKMKL, (SEQ ID NO: 24)
    naphthylacetyl-FFRKFKSKL, (SEQ ID NO: 25)
    naphthylacetyl-FFLRKFKSKL, (SEQ ID NO: 26)
    naphthylacetyl-FFKKFKGKL, (SEQ ID NO: 27)
    naphthylacetyl-FFFKKFKGKL, (SEQ ID NO: 28)
    naphthylacetyl-FFEKFKFKL, (SEQ ID NO: 29)
    naphthylacetyl-FFFEKFKFKL, (SEQ ID NO: 30)
    naphthylacetyl-FFKKLKFYL, (SEQ ID NO: 31)
    naphthylacetyl-FFFKKLKFYL, (SEQ ID NO: 32)
    naphthylacetyl-FFKTLKFHL, (SEQ ID NO: 33)
    naphthylacetyl-FFFKTLKFHL, (SEQ ID NO: 34)
    naphthylacetyl-FFKRFRHKL, (SEQ ID NO: 35)
    naphthylacetyl-FFLKRFRHKL, (SEQ ID NO: 36)
    naphthylacetyl-FFKKFQWHL, (SEQ ID NO: 37)
    naphthylacetyl-FFLKKFQWHL, (SEQ ID NO: 38)
    naphthylacetyl-FFKKKFKLKL, (SEQ ID NO: 39)
    naphthylacetyl-FFKLKKFKLKL, (SEQ ID NO: 40)
    naphthylacetyl-FFKKKFKMKL, (SEQ ID NO: 41)
    naphthylacetyl-FFKLKKFKMKL, (SEQ ID NO: 42)
    naphthylacetyl-FFKRKFKSKL, (SEQ ID NO: 43)
    naphthylacetyl-FFKLRKFKSKL, (SEQ ID NO: 44)
    naphthylacetyl-FFKKKFKGKL, (SEQ ID NO: 45)
    naphthylacetyl-FFKFKKFKGKL, (SEQ ID NO: 46)
    naphthylacetyl-FFKEKFKFKL, (SEQ ID NO: 47)
    naphthylacetyl-FFKFEKFKFKL, (SEQ ID NO: 48)
    naphthylacetyl-FFKKKLKFYL, (SEQ ID NO: 49)
    naphthylacetyl-FFKFKKLKFYL, (SEQ ID NO: 50)
    naphthylacetyl-FFKKTLKFHL, (SEQ ID NO: 51)
    naphthylacetyl-FFKFKTLKFHL, (SEQ ID NO: 52)
    naphthylacetyl-FFKKRFRHKL, (SEQ ID NO: 53)
    naphthylacetyl-FFKLKRFRHKL, (SEQ ID NO: 54)
    naphthylacetyl-FFKKKFQWHL, (SEQ ID NO: 55)
    naphthylacetyl-FFKLKKFQWHL, (SEQ ID NO: 56)
    naphthylacetyl-FFKFKKFKLKL, (SEQ ID NO: 57)
    naphthylacetyl-FFKFLKKFKLKL, (SEQ ID NO: 58)
    naphthylacetyl-FFKFKKFKMKL,
```

-continued naphthylacetyl-FFKFLKKFKMKL, (SEQ ID NO: 59)

naphthylacetyl-FFKFRKFKSKL, (SEQ ID NO: 60)

naphthylacetyl-FFKFLRKFKSKL, (SEQ ID NO: 61)

naphthylacetyl-FFKFKKFKGKL, (SEQ ID NO: 62)

naphthylacetyl-FFKFFKKFKGKL, (SEQ ID NO: 63)

naphthylacetyl-FFKFEKFKFKL, (SEQ ID NO: 64)

naphthylacetyl-FFKFFEKFKFKL, (SEQ ID NO: 65)

naphthylacetyl-FFKFKKLKFYL, (SEQ ID NO: 66)

naphthylacetyl-FFKFFKKLKFYL, (SEQ ID NO: 67)

naphthylacetyl-FFKFKTLKFHL, (SEQ ID NO: 68)

naphthylacetyl-FFKFFKTLKFHL, (SEQ ID NO: 69)

naphthylacetyl-FFKFKRFRHKL, (SEQ ID NO: 70)

naphthylacetyl-FFKFLKRFRHKL, (SEQ ID NO: 71)

naphthylacetyl-FFKFKKFQWHL, (SEQ ID NO: 72)

naphthylacetyl-FFKFLKKFQWHL, (SEQ ID NO: 73)

naphthylacetyl-ffKKFKLKL, naphthylacetyl-ffLKKFKLKL, naphthylacetyl-ffKKFKMKL, naphthylacetyl-ffLKKFKMKL, naphthylacetyl-ffRKFKSKL, naphthylacetyl-ffLRKFKSKL, naphthylacetyl-ffKKFKGKL, naphthylacetyl-ffFKKFKGKL, naphthylacetyl-ffEKFKFKL, naphthylacetyl-ffFEKFKFKL, naphthylacetyl-ffKKLKFYL, naphthylacetyl-ffFKKLKFYL, naphthylacetyl-ffKTLKFHL, naphthylacetyl-ffFKTLKFHL, naphthylacetyl-ffKRFRHKL, naphthylacetyl-ffLKRFRHKL, naphthylacetyl-ffKKFQWHL, naphthylacetyl-ffLKKFQWHL, naphthylacetyl-ffkKKFKLKL, naphthylacetyl-ffkLKKFKLKL, naphthylacetyl-ffkKKFKMKL, naphthylacetyl-ffkLKKFKMKL, naphthylacetyl-ffkRKFKSKL, naphthylacetyl-ffkLRKFKSKL, naphthylacetyl-ffkKKFKGKL, naphthylacetyl-ffkFKKFKGKL, naphthylacetyl-ffkEKFKFKL, naphthylacetyl-ffkFEKFKFKL, naphthylacetyl-ffkKKLKFYL, naphthylacetyl-ffkFKKLKFYL, naphthylacetyl-ffkKTLKFHL, naphthylacetyl-ffkFKTLKFHL, naphthylacetyl-ffkKRFRHKL, naphthylacetyl-ffkLKRFRHKL, naphthylacetyl-ffkKKFQWHL, naphthylacetyl-ffkLKKFQWHL, naphthylacetyl-ffkKKFKLKL, naphthylacetyl-ffkLKKFKLKL, naphthylacetyl-ffkfKKFKMKL, naphthylacetyl-ffkfLKKFKNIKL, naphthylacetyl-ffkfRKFKSKL, naphthylacetyl-ffkfLRKFKSKL, naphthylacetyl-ffkfKKFKGKL, naphthylacetyl-ffkfFKKFKGKL, naphthylacetyl-ffkfEKFKFKL, naphthylacetyl-ffkfFEKFKFKL, naphthylacetyl-ffkfKKLKFYL, naphthylacetyl-ffkfFKKLKFYL, naphthylacetyl-ffkfKTLKFHL, naphthylacetyl-ffkfFKTLKFHL, naphthylacetyl-ffkfKRFRHKL, naphthylacetyl-ffkfLKRFREKL, naphthylacetyl-ffkfKKFQWHL, naphthylacetyl-ffkfLKKFQWHL, thyminylacetyl-ffkkfklkl (NP1), thyminylacetyl-FFKKFKLKL, (NP2, SEQ ID NO: 74)

thyminylacetyl-ffkkfkl (NP3),

-continued thyminylacetyl-FFKKFKL, (NP4, SEQ ID NO: 75)

thyminylacetyl-ffkkf (NP5), thyminylacetyl-FFKKF, (NP6, SEQ ID NO: 76)

thyminylacetyl-ffrrfrlrl (NP1/r), thyminylacetyl-FFRRFRLRL, (SEQ ID NO: 81)

uracilylacetyl-ffkkfklkl, uracilylacetyl-FFKKFKLKL, (SEQ ID NO: 82)

uracilylacetyl-ffkkfkl, uracilylacetyl-FFKKFKL, (SEQ ID NO: 83)

uracilylacetyl-ffkkf, uracilylacetyl-FFKKF, (SEQ ID NO: 84)

uracilylacetyl-ffrrfrlrl, uracilylacetyl-FFRRFRLRL, (SEQ ID NO: 85)

cytosinylacetyl-ffkkfklkl, cytosinylacetyl-FFKKFKLKL, (SEQ ID NO: 86)

cytosinylacetyl-ffkkfkl, cytosinylacetyl-FFKKFKL, (SEQ ID NO: 87)

cytosinylacetyl-ffkkf, cytosinylacetyl-FFKKF, (SEQ ID NO: 88)

cytosinylacetyl-ffrrfrlrl, cytosinylacetyl-FFRRFRLRL, (SEQ ID NO: 89)

adeninylacetyl-ffkkfklkl, adeninylacetyl-FFKKFKLKL, (SEQ ID NO: 90)

adeninylacetyl-ffkkfkl, adeninylacetyl-FFKKFKL, (SEQ ID NO: 91)

adeninylacetyl-ffkkf, adeninylacetyl-FFKKF, (SEQ ID NO: 92)

adeninylacetyl-ffrrfrlrl, adeninylacetyl-FFRRFRLRL, (SEQ ID NO: 93)

guaninylacetyl-ffkkfklkl, guaninylacetyl-FFKKFKLKL, (SEQ ID NO: 94)

guaninylacetyl-ffkkfkl, guaninylacetyl-FFKKFKL, (SEQ ID NO: 95)

guaninylacetyl-ffkkf, guaninylacetyl-FFKKF, (SEQ ID NO: 96)

guaninylacetyl-ffrrfrlrl,
and guaninylacetyl-FFRRFRLRL. (SEQ ID NO: 97)

10. A product formed by exposing the peptide of claim 1 to a bioactive molecule that induces oligomerization and hydrogelation.

11. An oligomerized product comprising two or more peptides according to claim 1 in activated form having a random structure.

12. The oligomerized product of claim 11 further comprising a therapeutic agent retained within the structure of the oligomerized product.

13. The oligomerized product of claim 12, wherein the therapeutic agent is selected from the group consisting of antigens, enzymes, antibiotics or antimicrobials, antineoplastic agents, local anesthetics, hormones, angiogenic agents, anti-angiogenic agents, growth factors, antibodies, neurotransmitters, psychoactive drugs, anticancer drugs, chemotherapeutic drugs, drugs affecting reproductive organs, recombinant DNA or vectors containing recombinant DNA, anti-inflammatory drugs, analgesics, anti-proliferatives, anti-fibrotics, and oligonucleotides.

14. A supramolecular hydrogel formed upon self-assembly of the oligomerized product of claim 11 in an aqueous medium.

15. A pharmaceutical composition comprising a pharmaceutically acceptable carrier and a peptide according to claim 1.

16. The pharmaceutical composition according to claim 15 further comprising a therapeutic agent, wherein the therapeutic agent is selected from the group consisting of antigens, enzymes, antibiotics or antimicrobials, antineoplastic agents, local anesthetics, hormones, angiogenic agents, anti-angiogenic agents, growth factors, antibodies, neurotransmitters, psychoactive drugs, anticancer drugs, chemotherapeutic drugs, drugs affecting reproductive organs, recombinant DNA or vectors containing recombinant DNA, anti-inflammatory drugs, analgesics, anti-proliferatives, anti-fibrotics, and oligonucleotides.

17. A method of delivering a therapeutic agent to an individual, the method comprising:
    administering an oligomerized product according to claim 12 to the individual, whereby the therapeutic agent is released from the oligomerized product to the body of the individual after said administering.

18. A method of delivering a therapeutic agent to an individual, the method comprising:
    administering a pharmaceutical composition according to claim 16 to the individual; and
    administering a bioactive activator to the site where the pharmaceutical composition is administered to induce in situ oligomerization and hydrogelation of the peptide,
    whereby the therapeutic agent is subsequently released from the in situ formed hydrogel to the body of the individual.

19. A method of promoting wound healing comprising:
administering to a wound of a subject a therapeutically effective amount of two or more peptides according to claim 1, wherein said administering is effective to activate the two or more peptides and induce oligomerization of the activated two or more peptides.

20. A method of promoting wound healing comprising:
administering to a wound of a subject a therapeutically effective amount of a product according to claim 10.

21. A method of promoting an immune response in an individual, the method comprising:
administering to an individual a therapeutically effective amount of the pharmaceutical composition according to claim 15, wherein the pharmaceutical composition further comprises an antigen and wherein said administering is effective to activate the peptide and induce oligomerization of the activated peptide and to induce an immune response against the antigen in the pharmaceutical composition.

22. A method of promoting an immune response in an individual, the method comprising:
administering to an individual a therapeutically effective amount of the oligomerized product of claim 10, wherein the oligomerized product further comprises an antigen and wherein said administering is effective to induce an immune response against the antigen in the oligomerized product.

23. A method of causing oligomerization and/or hydrogelation of two or more peptides, the method comprising contacting two or more peptides according to claim 1 with a bioactive activator sufficient to induce oligomerization and hydrogelation.

24. A method of selectively sequestering ATP, the method comprising:
contacting ATP, in an aqueous environment, with a peptide according to claim 7, whereby said contacting is effective to cause ATP binding to the peptide.

25. A method of inhibiting cancer cell efflux of an antineoplastic agent, anticancer drug, or chemotherapeutic drug, the method comprising:
contacting a cancer cell with a solution comprising two or more peptides according to claim 7 and any one of an antineoplastic agent, an anticancer drug, or a chemotherapeutic drug,
wherein said contacting allows the cancer cell to take up the two or more peptides and the antineoplastic agent, anticancer drug, or chemotherapeutic drug, and the peptide inhibits efflux of the antineoplastic agent, anticancer drug, or chemotherapeutic drug from the contacted cancer cell.

26. A method of treating a patient having cancer, the method comprising:
administering to the patient an antineoplastic agent, an anticancer drug, or a chemotherapeutic drug; and
administering to the patient a solution comprising two or more peptides according to claim 7, wherein said administering steps allows cancer cells to take up the two or more peptides, or an oligomerization product formed by said two or more peptides, and the antineoplastic agent, anticancer drug, or chemotherapeutic drug, and wherein the peptide or oligomerization product inhibits efflux of the antineoplastic agent, anticancer drug, or chemotherapeutic drug from cancer cells.

27. A method of treating a patient having cancer, the method comprising:
administering to the patient the oligomerized product of claim 13 that comprises any one of an antineoplastic agent, an anticancer drug, or a chemotherapeutic drug retained within the structure of the oligomerized product, wherein said administering allows cancer cells to take up the oligomerized product, and the antineoplastic agent, anticancer drug, or chemotherapeutic drug, and wherein the oligomerized product inhibits efflux of the antineoplastic agent, anticancer drug, or chemotherapeutic drug from cancer cells.

\* \* \* \* \*

UNITED STATES PATENT AND TRADEMARK OFFICE
CERTIFICATE OF CORRECTION

PATENT NO. : 11,839,661 B2
APPLICATION NO. : 16/639467
DATED : December 12, 2023
INVENTOR(S) : Xu et al.

It is certified that error appears in the above-identified patent and that said Letters Patent is hereby corrected as shown below:

In the Claims

In Claim 9, Column 84, Line 37, delete "naphthylacetyl-ffkfLKKFKNIKL" and insert --naphthylacetyl-ffkfLKKFKMKL--.

In Claim 9, Column 84, Line 57, delete "naphthylacetyl-ffkfLKRFREKL" and insert --naphthylacetyl-ffkfLKRFRHKL--.

In Claim 9, Column 85, Line 65, delete "guaninylacetyl-ffkkfld" and insert --guaninylacetyl-ffkkfl--.

Signed and Sealed this
Fourteenth Day of May, 2024

Katherine Kelly Vidal
*Director of the United States Patent and Trademark Office*